United States Patent [19]

Weston et al.

[11] Patent Number: 5,466,710
[45] Date of Patent: * Nov. 14, 1995

[54] HETEROBICYCLOALKANES AS PESTICIDAL COMPOUNDS

[75] Inventors: John B. Weston; John P. Larkin; Ian H. Smith, all of Berkhamsted, England

[73] Assignee: Roussel Uclaf, France

[*] Notice: The portion of the term of this patent subsequent to Jun. 25, 2008, has been disclaimed.

[21] Appl. No.: 132,488

[22] Filed: Oct. 6, 1993

Related U.S. Application Data

[60] Continuation of Ser. No. 843,195, Feb. 28, 1992, abandoned, which is a division of Ser. No. 222,405, Jul. 21, 1988, Pat. No. 5,116,862, which is a continuation-in-part of Ser. No. 171,311, Mar. 21, 1988, abandoned.

[51] Int. Cl.$^6$ .................. A01N 43/32; C07D 323/04; C07D 339/08; A61K 31/655; A61K 31/335
[52] U.S. Cl. .................................................. 514/452
[58] Field of Search .................. 549/15, 16, 363, 549/360, 214, 215, 332, 337; 514/436, 452, 336, 363, 214, 149

[56] References Cited

U.S. PATENT DOCUMENTS

| | | | |
|---|---|---|---|
| 3,686,224 | 8/1972 | Deffner | 260/340.7 |
| 4,425,473 | 1/1984 | Mizutani et al. | 549/363 |
| 4,526,949 | 7/1985 | Hall et al. | 549/363 |
| 4,772,624 | 9/1988 | Palmer et al. | 549/363 X |
| 4,942,173 | 7/1990 | Casida et al. | 549/363 X |
| 4,965,257 | 10/1990 | Casida et al. | 549/363 X |
| 5,026,874 | 6/1991 | Larkin et al. | 549/15 |
| 5,057,508 | 10/1991 | Casida et al. | 549/363 X |
| 5,116,862 | 5/1992 | Weston et al. | 514/436 |

FOREIGN PATENT DOCUMENTS

| | | | |
|---|---|---|---|
| 0152229A2 | 8/1985 | European Pat. Off. | A01N 43/90 |
| 0211598A2 | 2/1987 | European Pat. Off. | A01N 43/90 |
| 0216625A2 | 4/1987 | European Pat. Off. | A01N 43/90 |
| 0216624A2 | 4/1987 | European Pat. Off. | A01N 43/90 |
| 0235979A1 | 9/1987 | European Pat. Off. | A01N 53/00 |
| 3103779 | 1/1982 | Germany | 549/363 |
| 56-108793 | 8/1981 | Japan | 549/363 |
| 57-159788 | 10/1982 | Japan | 549/363 |
| 60-208983 | 10/1985 | Japan | 549/363 |

OTHER PUBLICATIONS

*J. Agric. Food Chem*, 1985, 33, 976–980, Palmer et al "1,4–Disubstituted 2,6,7-Trioxabicyclo . . . ".
U.S. Chemical Abstracts, vol. 108, 1988, 177378.
U.S. Chemical Abstracts, vol. 108, 1988 177379e.
U.S. Chemical Abstracts, vol. 108, 1988, 132461j.
U.S. Chemical Abstracts, vol. 104, 1986, 149601v.
U.S. Chemical Abstracts, vol. 104, 1986, 109658n.
U.S. Chemical Abstracts, vol. 104, 1986, 88566p.
U.S. Chemical Abstracts, vol. 103, 1985, 155776b.
U.S. Chemical Abstracts, vol. 103, 1985, 216347m.
U.S. Chemical Abstracts, vol. 100, 1984, 197826m.
U.S. Chemical Abstracts, vol. 92, 1980, 174215p.
U.S. Chemical Abstracts, vol. 91, 1979, 69413h.
U.S. Chemical Abstracts, vol. 90, 1979, 80705e.
U.S. Chemical Abstracts, vol. 89, 1978, 36467j.
U.S. Chemical Abstracts, vol. 85, 1976, 73049.
GB Journal of Medicinal Chemistry, 1970, vol. 13, No. 6, pp. 1212–1215.

*Primary Examiner*—Floyd D. Higel
*Attorney, Agent, or Firm*—Nixon & Vanderhye

[57] ABSTRACT

The present invention provides a class of substituted bicyclooctanes of formula

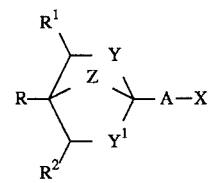

wherein R is a $C_{2-10}$ non-aromatic hydrocarbyl optionally substituted by cyano, halo, $C_{1-4}$ alkoxy, $C_{1-4}$ haloalkoxy or $S(O)_m R^3$; $R^1$ and $r^2$ are independently hydrogen, halo, a $C_{1-3}$ aliphatic group optionally substituted, $S(O)_m R^4$, or $R^1$ and $R^2$ and the carbon atoms to which they are attached form a $C_{5-7}$ carbocyclic ring optionally substituted by halo, or a $C_{1-3}$ aliphatic or alkoxy group;

A-X is a group:
  (i) A'C≡CX in which A' is a $C_{3-6}$ alkyl, alkenyl or alkynyl or a $C_{3-10}$ cycloalkyl or cycloalkenyl group all optionally containing one to three hetero atoms.
  (ii) BX in which B is a group $(CH_2)_2O$ or $(CH_2)_2S(O)_n$ or a $C_{2-6}$ aliphatic chain optionally containing one or two oxygen or sulphur atoms and/or double bonds and optionally further substituted;

X is hydrogen, halo, $SiR^5R^6R^7$ or $SnR^5R^6R^7$ or $CR^8R^9R^{10}$; Y and $Y^1$ are independentaly oxygen or $S(O)_{n'}$ and Z is $CH_2S(O)_{n''}$ provided that when A does not contain a C≡C fragment, X is a group $CR^8R^9R^{10}$.

The compounds have valuable pesticidal activity, particularly against arthropods and helminths. Pesticidal formulations containing the compounds of formula (I), their use in the control of pests and methods for their preparation are also disclosed.

14 Claims, No Drawings

HETEROBICYCLOALKANES AS PESTICIDAL COMPOUNDS

This application is a continuation of application Ser. No. 07/843,195, filed Feb. 28,1992, now abandoned, which in turn is a division of application Ser. No. 07/222,405 filed Jul. 21, 1988 now U.S. Pat. No. 5,116,862, which is a continuation-in-part of Ser. No. 07/171,311, filed Mar. 21, 1988, abandoned.

The present invention relates to novel chemical compounds having pesticidal activity, to methods for their preparation, to compositions containing them and to their use in the control of pests. More particularly the invention relates to a class of heterobicycloalkanes.

The use of certain 2,6,7-trioxabicyclo[2.2.2]octanes is disclosed in European Patent Applications Nos. 152229, 211598, 216625 and 216624. It has now been discovered that derivatives of these compounds have interesting pesticidal activity.

Accordingly, the present invention provides a compound of the formula (I):

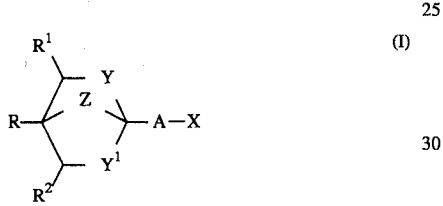

wherein R is a $C_{2-10}$ non-aromatic hydrocarbyl group optionally substituted by, or methyl substituted by cyano, halo, $C_{1-4}$ alkoxy optionally substituted by halo, or a group $S(O)_m R^3$ where $R^3$ is $C_{1-4}$ alkyl optionally substituted by halo and m is 0, 1 or 2, or R is phenyl optionally substituted by $C_{1-4}$ alkoxy, $C_{1-3}$ alkyl, $C_{2-4}$ alkynyl, halo, $C_{1-4}$ haloalkyl, cyano or a group $S(O)_m R^3$ as defined hereinbefore;

$R^1$ and $R^2$ may be the same or different, and each is hydrogen, halo, or a $C_{1-3}$ aliphatic group optionally substituted by halo, cyano, $C_{1-5}$ carbalkoxy, $C_{1-4}$ alkoxy, or a group $S(O)_{m'} R^4$ wherein m' is 0, 1 or 2 and $R^4$ is $C_{1-4}$ alkyl; cyano, gem dimethyl, or $C_{1-5}$ carbalkoxy, or $R^1$ and R and the carbon atoms to which they are attached form a $C_{5-7}$ carbocyclic ring optionally substituted by halo, or a $C_{1-3}$ aliphatic or alkoxy group;

A-X contains between 3 and 20 carbon atoms wherein A is a $C_{2-12}$ non-aromatic hydrocarbyl group which optionally contains one to six hetero atoms which are the same or different and are each selected from oxygen, sulphur, nitrogen, fluoro or chloro and is optionally substituted by one or two hydroxy groups or A is a $CH_2O$ or $CH_2S(O)_n$ group wherein n is 0, 1 or 2;

X is hydrogen, halo, a group Si $R^5$, $R^6$, $R^7$ or Sn $R^5$, $R^6$, $R^7$ wherein $R^5$, $R^6$ and $R^7$ are the same or different and are each a hydrocarbyl group containing up to 8 carbon atoms optionally substituted by one to three halo, $C_{1-6}$ alkoxy, $C_{1-6}$ alkyl thio, $C_{1-6}$ alkylsulphinyl, $C_{1-6}$ alkylsulphonyl, cyano, $C_{1-6}$ acyloxy or $C_{1-6}$ carbalkoxy groups or, when one or more of $R^5$ to $R^7$ is alkynyl, this is optionally substituted by silyl substituted by three $C_{1-4}$ alkyl groups, or X is a group

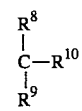

wherein $R^8$ and $R^9$ are the same or different and are each independently selected from hydrogen, halo, cyano, $C_{1-5}$ carbalkoxy, $C_{1-4}$ alkyl optionally substituted by one to three halo atoms, cyano, $C_{1-4}$ carbalkoxy, $C_{1-4}$ alkoxy or a group $S(O)_{m''} R^{11}$ wherein m'' is 0, 1 or 2 and $R^{11}$ is $C_{1-4}$ alkyl; $C_{1-4}$ alkoxy or $S(O)_{m'''} R^{12}$ wherein m''' is 0, 1 or 2 and $R^{12}$ is $C_{1-4}$ alkyl optionally substituted by one to three fluoro atom, or $R^8$ and $R^9$ and the carbon atom to which they are attached form a $C_{3-6}$ cycloalkyl ring, and $R^{10}$ is hydrogen, halo, hydroxy, cyano, $C_{1-4}$ alkoxy, $C_{1-4}$ acyloxy $C_{1-5}$ carbalkoxy or a $C_{1-9}$ hydrocarbyl group optionally substituted by hydroxy, cyano, $C_{1-4}$ alkoxy, $C_{1-4}$ acyloxy, $C_{1-4}$ carbalkoxy, one to three halo atoms or a group $S(O)_{m''''} R^{13}$ wherein m'''' is 0, 1 or 2 and $R^{13}$ is $C_{1-4}$ alkyl, or $R^{10}$ is a group $S(O)_{m'''''} R^{14}$ wherein m''''' is 0, 1 or 2 and $R^{14}$ is $C_{1-4}$ alkyl optionally substituted by one to three fluoro atoms;

Y and $Y^1$ are the same or different and are each selected from oxygen and $S(O)_{n'}$, where n' is 0, 1 or 2; and Z is $CH_2CH_2$, $CH_2O$ or $CH_2S(O)_{n''}$, wherein n'' is 0, 1 or 2; provided that when A does not contain a C≡C fragment X is a group

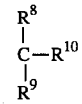

wherein $R^8$, $R^9$ and $R^{10}$ are as hereinbefore defined except that $R^8$ and $R^9$ are not hydrogen.

In the definition of Z, the first mentioned atom is adjacent to the 4-position of the bicyclic ring system.

When R is an alkyl, alkenyl or alkynyl, cycloalkyl or cycloalkenyl group this preferably contains up to 6 carbon atoms. Conveniently, when R is substituted there are up to seven substituents when the substituent is fluoro, three substituents when the substituents are chloro or bromo or one substituent when this is other than halo.

Suitably, R is an aliphatic or alicyclic group containing between 2 and 8 carbon atoms or phenyl each optionally substituted by cyano, one to seven halo atoms, $C_{1-4}$ alkoxy or a group $S(O)_m R^4$ as hereinbefore defined. Most suitably R is propyl, butyl, pentyl, $C_{2-5}$ alkenyl or alkynyl, cyclopropylmethyl, $C_{3-7}$ cycloalkyl or phenyl each optionally substituted by fluoro, chloro or bromo, for example, n-propyl,n-butyl, i-butyl, sec-butyl, t-butyl, prop-2-enyl, 2-methylprop-2-enyl, but-3-enyl, phenyl, cyclopentyl or cyclohexyl. Preferably R is n-propyl, n-butyl, i-butyl, t-butyl or phenyl.

Suitably $R^1$ is hydrogen, halo, cyano, methyl or ethyl each optionally substituted by cyano, methoxy, methylthio, chloro, bromo or fluoro. Most suitably $R^1$ is hydrogen, methyl, cyano, trifluoromethyl or ethyl. Preferably $R^1$ is hydrogen, methyl, cyano or trifluoromethyl.

Suitably $R^2$ is hydrogen, cyano, methyl or trifluoromethyl. Most suitably $R^2$ is hydrogen or methyl. Preferably $R^2$ is hydrogen.

Preferably Z is $CH_2S$ or $CH_2O$.

Suitably Y and y1 are both selected from oxygen or sulphur.

Suitably A is a $C_{2-8}$ non-aromatic hydrocarbyl group which optionally contains one to three hetero atoms as defined hereinbefore. In one preferred embodiment, A is a $C_{5-8}$ non-aromatic hydrocarbyl group which optionally contains one hetero atom and terminates in a —C≡C— fragment adjacent to X. Preferably A is a —(CH$_2$)$_4$ C≡C— group, a

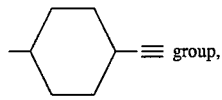 group, a —CH=CH(CH$_2$)$_2$C≡C— group, a CH$_2$O(CH$_2$)$_2$C≡C— group, a —(CH$_2$)$_3$CH(CH$_3$)C≡C— group, a —(CH$_2$)$_2$CH(CH$_3$)CH$_2$C≡C— group a —CH CH(CH$_3$)(CH$_2$) $_2$C≡C— group a —(CH$_2$)$_2$CH=CHC≡C— group or a —(CH$_2$)$_3$ C≡C— group and X is hydrogen or $C_{1-4}$ alkyl optionally substituted by an hydroxy, $C_{1-4}$ alkoxy or $C_{1-4}$ acyloxy group or one to three halo atoms. In a second preferred embodiment A is a —CH$_2$CH$_2$—, —CH=CH— or —C≡C— group and X is a group

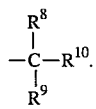

Suitably $R^8$, $R^9$ and R10 are each selected from chloro, bromo, methoxy or methyl optionally substituted by methoxy or fluoro.

The compounds of the formula (I) may exist in a number of isomeric forms. The present invention provides individual isomers of compounds of the formula (I) and mixtures thereof. The present invention also encompasses compounds of the formula (I) containing radioisotopes, particuarly those in which one carbon atom is $C^{14}$ or one to three hydrogen atoms are replaced by tritium.

One preferred group of compounds of the present invention is that of the formula (IA):

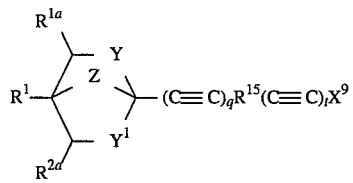 (IA)

wherein $R^a$ is $C_{2-10}$ alkyl, alkenyl or alkynyl, each optionally substituted by, or methyl substituted by, cyano, halo, $C_{3-4}$ cycloalkyl optionally substituted by halo, $C_{1-4}$ alkoxy optionally substituted by halo, or a group $S(O)_mR^3$ as defined hereinbefore or $R^a$ is $C_{3-10}$ cycloalkyl, $C_{4-10}$ cycloalkenyl or phenyl, each optionally susubstituted by $C_{1-4}$ alkoxy, $C_{1-3}$ alkyl optionally substituted by up to 3 halo atoms, $C_{2-4}$ alkynyl, halo, cyano or a group $S(O)_m$ $R^3$ as defined hereinbefore;

$R^{1a}$ and $R^{2a}$ may be the same or different, and each is hydrogen, halo, or an aliphatic group containing up to 3 carbon atoms optionally substituted by halo, cyano, $C_{1-4}$ alkoxy or a group $S(O)_m$, $R^4$ as defined hereinbefore; alkyl carbalkoxy containing up to 6 carbon atoms, or alkynyl substituted by tri-$C_{1-4}$ alkylsilyl, or $R^{1a}$ is COO—$C_{1-4}$-alkyl, cyano, gem dimethyl, or $R^{1a}$ and $R^a$ and the carbon atoms to which they are attached form a $C_{5-7}$ carbocyclic ring optionally substituted by halo, $C_{1-3}$ alkyl or alkoxy or $C_{2-3}$ alkenyl;

or $R^{15}$ is a single bond, a group $R^{15'}$ wherein $R^{15'}$ is a group

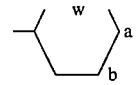

optionally substituted by one to five methyl groups or halo atoms wherein w is oxygen, a group $S(O)_p$ wherein p is 0, 1 or 2 or (CH$_2$)$_r$, wherein r is 1, 2 or 3 and the fragment (C≡C)$_t X^a$ is attached to the a or b position of the ring or $R^{15'}$ is a aliphatic chain containing between 1 and 8 carbon atoms in which one or two heteroatoms may be interspersed, the chain and $R^{15'}$ being optionally substituted by one to four substituents which may be the same or different and are, each independently selected from hydroxy, oxo, halo, $C_{1-4}$ alkyl or $C_{1-4}$ alkoxy, each optionally substituted by up to 3 halo atoms, $C_{1-4}$ acyloxy, epoxy, a $C_{1-4}$ alkylidene group, a $C_{1-6}$ carbalkoxy group, cyano, or a group $S(O)_{p'}$, $R^{4a}$ wherein p' is 0, 1 or 2 and $R^{4a}$ is $C_{1-4}$ alkyl, $X^a$ is selected from hydrogen, halo, C1-10 hydrocarbyl optionally substituted by an hydroxy, $C_{1-4}$ alkoxy or $C_{1-4}$ acyloxy group or one to three halo atoms, or $X^a$ is a group Si $R^{5a}R^{6a}R^{7a}$ or Sn $R^{5a}$ $R^{6a}$ $R^{7a}$ wherein $R^{5a}$, $R^{6a}$ and $R^{7a}$ are the same or different and are each a hydrocarbyl group containing up to 6 carbon atoms optionally substituted by one to three halo, cyano, alkoxy, alkylthio, acyloxy or carbalkoxy groups containing up to 6 carbon atoms or $X^a$ is a group $R^{16}$ OCO wherein $R^{16}$ is $C_{1-4}$ alkyl;

q is 0 or 1 and t is 1 or 2; provided that the sum of q and t is not greater than 2;

Y and $Y^1$ are the same or different and are each selected from oxygen and s(O)$_{n'}$ where n' is 0, 1 or 2; Z is CH$_2$O or CH$_2$S(O)$_{n''}$ wherein n" is 0, 1 or 2, except that $X^a$ cannot be hydrogen when q is 0. t is 1 and $R^{15}$ is a single bond.

Suitable heteroatoms for interspersion in the alkylene chain include oxygen, nitrogen and sulphur, the sulphur being optionally oxidised as the sulphoxide or sulphone. Oxygen and nitrogen atoms may be adjacent to each other in which case they may form an oxime group.

Suitable and preferred values for the groups $R^a$, $R^{1a}$, $R^{2a}$, Y, Z and $Y^1$ are as defined hereinbefore for the groups R, $R^1$, $R^2$, Y, Z and $Y^1$ respectively. Suitably $R^{15}$ is a single bond, a 1,4-cyclohexyl group, or an aliphatic chain as hereinbefore defined having between 2 and 6 carbon atoms optionally interspersed by an oxygen or sulphur atom. Suitably $X^a$ is hydrogen, $C_{1-3}$ alkoxymethyl or a group, Si $R^{17}R^{18}R^{19}$, wherein $R^{17}$, $R^{18}$ and $R^{19}$ are the same or different and each is $C_{1-4}$ alkyl. Preferably n is 0.

One preferred group of compounds of the formula (I) of the present invention is that of the formula (IB):

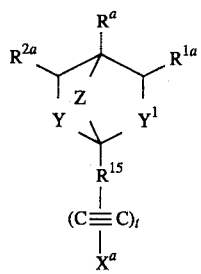

(IB)

wherein $R^a$, $R^{1a}$, $R^{2a}$, $X^a$, Y, $Y^1$, Z and t are as hereinbefore defined and $R^{15a}$ is a single bond or a group $R^{15'}$ as hereinbefore defined.

Suitably $R^{15a}$ is 1,4-cyclohexyl, t is 1 and $X^a$ is hydrogen or $C_{1-4}$ alkyl optionally substituted by an hydroxy, $C_{1-4}$ alkoxy or $C_{1-4}$ acyloxy group or one to three halo atoms or R15a is a single bond, t is 1 and $X^a$ is $C_{1-4}$ alkyl optionally substituted by an hydroxy, $C_{1-4}$ alkoxy or $C_{1-4}$ acyloxy group or one to three halo atoms. $X^a$ is preferably a tertiary group. Preferably $R^{15a}$ is cyclohexyl and $X^a$ is hydrogen or $R^{15a}$ is a single bond and $X^a$ is tertiary butyl.

A further preferred group of compounds of the present invention provides is that of the formula (IC)

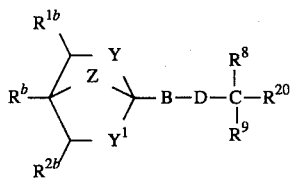

(IC)

wherein $R^b$ is a $C_{2-10}$ non-aromatic hydrocarbyl group optionally substituted by cyano, halo, $C_{1-4}$ alkoxy or a group $S(O)_m bR^{3b}$ where $R^{3b}$ is $C_{1-4}$ alkyl and $m^b$ is 0, 1 or 2, or $R^b$ is phenyl optionally substituted by $C_{1-4}$ alkoxy, $C_{1-3}$ alkyl, $C_{2-4}$ alkynyl halo $C_{1-4}$ haloalkyl, cyano or a group $S(O)_m bR^{3b}$ as defined hereinbefore;

$R^{1b}$ and $R^{2b}$ may be the same or different, and each is hydrogen, halo, or a $C_{1-3}$ aliphatic group optionally substituted by halo, cyano, $C_{1-5}$ carbalkoxy, or $C_{1-4}$ alkoxy; a group $S(O)_{m'}R^4$ wherein m' is 0, 1 or 2 and $R^4$ is $C_{1-4}$ alkyl; $C_{2-3}$ alkynyl, cyano, gem dimethyl, or $C_{1-5}$ carbalkoxy, or $R_{1b}$ and $R^b$ and the carbom atoms to which they are attached form a $C_{5-7}$ carbocyclic ring optionally substituted by halo, $C_{1-3}$ alkyl or alkoxy or $C_{2-3}$ alkenyl; $R^8$, $R^9$ are as defined hereinbefore and $R^{20}$ is a group $R^8$ as defined hereinbefore;

B is a single bond, methylene or a $C_{2-6}$ aliphatic chain which may contain one or two heteroatoms and/or double bonds but not triple bonds interspersed in the chain and which may be substituted by one to four substituents which may be the same or different and are each independently selected from hydroxy, oxo, halo, $C_{1-4}$ alkyl, $C_{1-4}$ alkoxy, $C_{1-4}$ acyloxy, epoxy, a $C_{1-4}$ alkylidene group, a $C_{1-6}$ carbalkoxy group, $C_{1-4}$ haloalkyl or cyano;

D is a single bond or a group $CH_2O$, $CH_2S(O)_n$ wherein n is 0,1 or 2,or D is a 1,2 cyclopropyl group;

Y and $Y^1$ and Z are as defined hereinbefore provided that B cannot be a single bond or methylene group when D is a single bond.

Suitably $R^b$ is propyl, butyl, pentyl, $C_{2-5}$ alkenyl or alkynyl, $C_{5-7}$cycloalkyl or phenyl each optionally substituted by fluoro, chloro or bromo. Most suitably $R^b$ is n-propyl,n-butyl, i-butyl, sec-butyl, t-butyl, phenyl, cyclopentyl or cyclohexyl and preferably $R^b$ is n-propyl, n-butyl, i-butyl, or t-butyl.

Suitably $R^{1b}$ is hydrogen, cyano, methyl or ethyl each optionally substituted by cyano, methoxy, methylthio, chloro, bromo or fluoro. Most suitably $R^{1b}$ is hydrogen, methyl, cyano, trifluoromethyl or ethyl. Preferably $R^{1b}$ is hydrogen, methyl, cyano or trifluoromethyl.

Suitable heteroatoms for inclusion in B include oxygen, nitrogen and sulphur, the sulphur being optionally oxidised as the sulphoxide or sulphone.

Suitably $R^8$, $R^{20}$ and $R^9$ are each selected from chloro bromo methoxy or methyl optionally substituted by methoxy or fluoro.

Suitably B is a group $(CH_2)_2$ or —CH=CH—.

Suitably D is a single bond.

Suitable and preferred values for the groups $R^{2b}$, Z, Y and Y' are as defined hereinbefore for the groups $R^2$,Z,Y and Y' respectively.

Preferred compounds of the present invention include:
1-(Hex-5-ynyl)-4-propyl-2,6,7-trioxabicyclo[2.2.2]octane
1-(Pent-4-ynyl)-4-propyl-3-trifluoromethyl-2,6,7-trioxabicyclo[2.2.2]octane
1-(Hex-5-ynyl)-4-propyl-3-trifluoromethyl-2,6,7-trioxabicyclo[2.2.2]octane
1-(Pent-4-ynyl)-4-propyl-2,6,7-trioxabicyclo[2.2.2]octane-3-carbonitrile
1-(Hex-5-ynyl)-4-propyl-2,6,7-trioxabicyclo[2.2.2]octane-3-carbonitrile
4-(Cyclohexyl)-1-(pent-4-ynyl)-2,6,7-trioxabicyclo[2.2.2]octane
4-(Cyclohexyl)-1-(hex-5-ynyl)-2,6,7-trioxabicyclo[2.2.2]octane
4-t-Butyl-1-(hex-5-ynyl)-2,6,7-trioxabicyclo[2.2.2]octane
4-t-Butyl-1-(6-trimethylsilylhex-5-ynyl)-2,6,7-trioxabicyclo[2.2.2]octane
1-(4-Ethynylcyclohexyl)-4-propyl-2,6,7-trioxabicyclo[2.2.2]octane
4-t-Butyl-1-(4-ethynylcyclohexyl)-2,6,7-trioxabicyclo[2.2.2]octane (cis and trans isomers)
4-t-Butyl-1-(3,3-dimethylbut-1-ynyl)-2,6,7-trioxabicyclo[2.2.2]octane.
1-(3,3-Dimethylbut-1-ynyl)-4-propyl-2,6,7-trioxabicyclo[2.2.2]octane-3-carbonitrile
4-t-Butyl-1-(hex-5-ynyl)-2,6-dioxa-7-thiabicyclo[2.2.2]octane
1-(Hex-5-ynyl)-4-propyl-2-oxa-6,7-dithiabicyclo[2.2.2]octane
1-(Hex-5-ynyl)-4-propyl-2,6,7-trithiabicyclo[2.2.2]octane
4-t-Butyl-1-[2-(prop-2-ynylthio)ethyl]-2,6,7-trioxabicyclo[2.2.21]octane
4-Propyl-1-[2-(prop-2-ynylthio)ethyl]-2,6,7-trioxabicyclo[2.2.2]octane
4-t-Butyl-1-[2-(prop-2-ynyloxy)ethyl]-2,6,7-trioxabicyclo[2.2.2]octane
4-Propyl-1-[2-(prop-2-ynyloxy)ethyl]-2,6,7-trioxabicyclo[2.2.2]octane-3-carbonitrile
1-(But-3-ynyloxymethyl)-4-propyl-2,6,7-trioxabicyclo[2.2.2]octane
4-t-Butyl-1-(but-3-ynyloxymethyl)-2,6,7-trioxabicyclo[2.2.2]octane
1-(But-3-ynyloxymethyl)-4-propyl-2,6,7-trioxabicyclo[2.2.2]octane-3-carbonitrile
4-t-Butyl-1-(hept-6-ynyl)-2,6,7-trioxabicyclo[2.2.2]octane
1-(Hept-6-ynyl)-4-propyl-2,6,7-trioxabicyclo[2.2.2]octane
4-Butyl-1-(hex-5-ynyl)-2,6,7-trioxabicyclo[2.2.2]octane-3-carbonitrile 1-(Hex-5-ynyl)-4-(2-methylprop-2-enyl)-2,6,7-trioxabi-
cyclo[2.2.2]octane-3-carbonitrile
1-(Hex-5-ynyl)-4-(prop-2-enyl)-2,6,7-trioxabicyclo[2.2.2]
octane-3-carbonitrile
1-(But-3-ynyloxymethyl)-4-(prop-2-enyl)-2,6,7-trioxabi-
cyclo[2.2.2]octane-3-carbonitrile
4-(But-3-enyl)-1-(hex-5-ynyl)-2,6,7-trioxabicyclo[2.2.2]oc-
tane-3-carbonitrile
4-t-Butyl-1-(4-methylhex-5-ynyl)-2,6,7-trioxabicyclo
[2.2.2]octane
1-[2-(But-3-ynyloxy)ethyl]-4-propyl-2,6,7-trioxabicyclo
[2.2.2]octane
1-[1-(But-3-ynyloxy)ethyl]-4-propyl-2,6,7-trioxabicyclo
[2.2.2]octane
1-(But-3-ynylthiomethyl)-4-propyl-2,6,7-trioxabicyclo
[2.2.2]octane
4-t-Butyl-1-(but-3-ynylthiomethyl)-2,6,7-trioxabicyclo
[2.2.2]octane
4-Butyl-1-(hex-5-ynyl)-2-oxa-6,7-dithiabicyclo[2.2.2]oc-
tane
4-t-Butyl-1-(hex-5-ynyl)-2-oxa-6,7-dithiabicyclo[2.2.2]oc-
tane
4-t-Butyl-1-(hex-5-ynyl)-2,6,7-trioxabicyclo[2.2.2]octane-
3-carbonitrile
1-(Hex-5-ynyl)-4-isobutyl-2,6,7-trioxabicyclo[2.2.2]oc-
tane-3-carbonitrile
4-Ethoxymethyl-1-(hex-5-ynyl)-2,6,7-trioxabicyclo[2.2.2]
octane-3-carbonitrile
1-(1-Methylhex-5-ynyl)-4-propyl-2,6,7-trioxabicyclo[2.2.2]
octane
4-t-Butyl-1-(1-methylhex-5-ynyl)-2,6,7-trioxabicyclo
[2.2.2]octane
1-(1-Methylhex-5-ynyl)-4-propyl-2,6,7-trioxabicyclo[2.2.2]
octane-3-carbonitrile
Methyl 7-(4-propyl-2,6,7-trioxabicyclo[2.2.2]oct-1-yl)hept-
2-ynoate
1-(Hex-5-ynyl)-4-phenyl-2,6,7-trioxabicyclo[2.2.2]octane
1-(Hex-5-ynyl)-4-isobutyl-2-oxa-6,7-dithiabicyclo[2.2.2]
octane
1-(Hex-5-ynyl)-3-methyl-4-propyl-2-oxa-6,7-dithiabicyclo
[2.2.2]octane
1-(3-Methylhex-5-ynyl)-4-propyl-2,6,7-trioxabicyclo[2.2.2]
octane-3-carbonitrile
1-(2-Methylhex-5-ynyl)-4-propyl-2,6,7-trioxabicyclo[2.2.2]
octane-3-carbonitrile
1-(3,3-Dimethylbut-1-ynyl)-4-isobutyl-2,6,7-trioxabicyclo
[2.2.2]octane-3-carbonitrile
1-(But-3-ynyloxymethyl)-4-propyl-2,6,7-trithiabicyclo
[2.2.2]octane
1-(trans-4(e)-ethynylcyclohexyl)-4-propyl-2,6,7-trioxabi-
cyclo[2.2.2]octane-3-carbonitrile
4-Propyl-1-[(E/Z)-6-(trimethylsilyl)hex-3-en-5-ynyl]-2,6,7-
trioxabicyclo[2.2.2] octane-3-carbonitrile
1-[(E/Z)-Hex-3-en-5-ynyl]-4-propyl-2,6,7-trioxabicyclo
[2.2.2]octane-3-carbonitrile (E:Z=1:2)
1-[(E/Z)-7-Methoxyhept-3-en-5-ynyl]-4-propyl-2,6,7-triox-
abicyclo[2.2.2]octane-3-carbonitrile (E:Z–1:2)
1-[(E/Z)-7-Hydroxyhept-3-en-5-ynyl]-4-propyl-2,6,7-triox-
abicyclo[2.2.2]octane-3-carbonitrile
4-t-Butyl-1-[(E)-hex-1-en-5-ynyl]-2,6,7-trioxabicyclo
[2.2.2]octane-3-carbonitrile
4-Propyl-2,6,7-trioxabicyclo[2.2.2]octane-1-carboxalde-
hyde oxime O-(prop-2-ynyl)ether
1-(Hex-5-ynyl)-4-isobutyl-2,6,7-trithiabicyclo[2.2.2]octane
1-(Hex-5-ynyl)-4-phenyl-2-oxa-6,7-dithiabicyclo[2.2.2]oc-
tane
4-Propyl-1-(4-methylhex-5-ynyl)-2,6,7-trioxabicyclo[2.2.2]
octane-3-carbonitrile 4-Ethyl-1-(hex-5-ynyl)-2,6,7-trithiabicyclo[2.2.2]octane
1-(Hex-5-ynyl)-4-phenyl-2,6,7-trioxabicyclo[2.2.2]octane-
3-carbonitrile
4-Cyclopropylmethyl-1-(hex-5-ynyl)-2,6,7-trioxabicyclo
[2.2.2]octane-3-carbonitrile
4-Isobutyl-1-(3-methylhex-5-ynyl)-2,6,7-trioxabicyclo
[2.2.2]octane-3-carbonitrile
1-[(s)-3-Methylhex-5-ynyl]-4-propyl-2,6,7-trioxabicyclo
[2.2.2]octane-3-carbonitrile
1-(2-Methylhex-5-ynyl)-4-(prop-2-enyl)-2,6,7-trioxabi-
cyclo[2.2.2]octane-3-carbonitrile
4-t-Butyl-1-(3,3-dimethylbutyl)-2,6,7-trioxabicyclo[2.2.2]
octane
1-[(E)-3,3-Dimethylbutyl]-4-propyl-2,6,7-trioxabicyclo
[2.2.2]octane-3-carbonitrile
1-[(E)-3,3-Dimethylbut-1-enyl]-4-propyl-2,6,7-trioxabi-
cyclo[2.2.2]octane-3-carbonitrile
1-(t-Butylthiomethyl)-4-propyl-2,6,7-trioxabicyclo[2.2.2]
octane-3-carbonitrile
1-[z)-1-Fluoro-3,3-dimethylbut-1-enyl]-4-propyl-2,6,7-tri-
oxabicyclo[2.2.2]octane-3-carbonitrile
1-(Hept-5-ynyl)-4-propyl-2,6,7-trioxabicyclo[2.2.2]octane By the term "hydrocarbyl" group is meant alkyl, alkenyl
(including cyclic alkyl and alkenyl, and alkyl and alkenyl
substituted by cyclic alkyl and alkenyl), alkynyl, aryl and
aralkyl groups. "Hydrocarbyloxy" means a hydrocarbyl
group as defined where linked to oxygen.

By the term "aliphatic" group is meant an alkyl, alkenyl
or alkynyl group.

By the term "halo" is meant fluoro, chloro, bromo or iodo.

In a further aspect, the present invention provides a
process for the preparation of a compound of the formula (I).
The process for the preparation of a compound of the
formula (I) may be any method known in the art for
preparing analogous compounds, for example:

(i) when Y and $Y^1$ are oxygen and Z is $CH_2O$:

a) by the cyclisation of a compound of the formula (II):

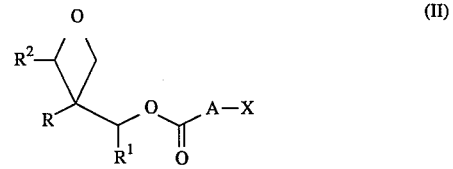

wherein R to $R^2$, A and X are as hereinbefore
defined, in the presence of an acid catalyst. Boron
trifluoride etherate is a particularly preferred acid
catalyst for this cyclisation which will normally be
carried out in an inert solvent, such as a halogenated
hydrocarbon, conveniently dichloromethane, at or
below ambient temperature, for example between
–100° and 50° C. and conveniently between –70°
and –25° C.

The compounds of the formula (II) may be prepared by
the reaction of compounds of the formulae (III) and (IV):

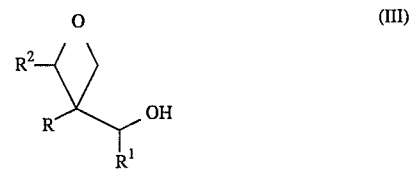

-continued

 (IV)

where R to $R^2$, A and X are as hereinbefore defined and L is a leaving group such as halo or hydroxy. This reaction conveniently takes place under conditions well known to those skilled in the art, for example when L is halo in an inert solvent in the presence of base at a non-extreme temperature and when L is hydroxy in an inert solvent in the presence of a condensing agent at a non extreme temperature. When L is halo, halogenated hydrocarbons, such as dichloromethane, are particularly suitable inert solvents and pyridine is a preferred base; when L is hydroxy, dimethylformamide is a suitable solvent, dicyclohexylcarbodiimide is a preferred condensing agent; and the reaction will conveniently be carried out at between –50° and 100° C., preferably between 0° and 25° C.

The compounds of the formula III may be prepared as described in copending European Patent Applications Nos. 211598 and 216624. The compounds of the formula (IV) may be prepared by methods well known to those skilled in the art, the synthesis of $XA\text{-}CO_2H$ ($XA$=4-ethynylcyclohexyl) is described in Appendix 1.

b) when A contains a terminal C≡C fragment
  (bi) by the reaction of a compound HC≡C—X with a compound of the formula (V):

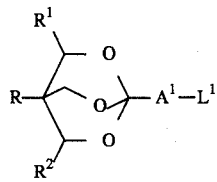 (V)

wherein R to $R^2$ are as hereinbefore defined, $A^1C\equiv C$ forms the group A and $L^1$ is a leaving group. Suitable leaving groups include halides such as bromo. The reaction is conveniently carried out in a strong base such as butyllithium, lithamide or sodamide at or below ambient temperature, for example between –70° and 30° C. in an inert solvent, conveniently tetrahydrofuran or diethyl ether. Liquid ammonia is a suitable solvent when the strong base is lithamide.

The compounds of formula (V) may be prepared by the cyclisation of the corresponding compounds of the formula (VI):

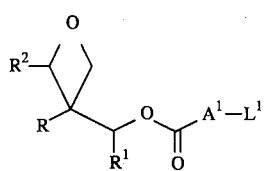 (VI)

The compounds of the formula (VI) may be prepared and cyclised under analogous conditions used for preparing and cyclising compounds of the formula (II).

(bii) when A contains a terminal C≡C fragment and X is hydrogen, by the reaction of a strong base with a compound of the formula (VII):

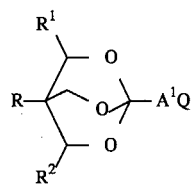 (VII)

wherein R to $R^2$ $A^1$, Y, $Y^1$ and Z are as hereinbefore defined and Q is a group capable of conversion into an ethynyl group, for example a group CH=C(hal)$_2$, (hal)CH=CH$_2$ or

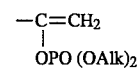

wherein hal is chloro or bromo, Alk is $C_{1\text{-}4}$ alkyl.

The reaction is conveniently carried out by methods well known to those skilled in the art, for example when Q is a group —CH=C(hal)$_2$ at about or below room temperature, for example between –70° C. and 25° C., in an inert solvent, conveniently an ether such as tetrahydrofuran.

Butyl lithium is a convenient strong base for use in this reaction. The starting material of the formula (VII) may be prepared by the reaction of a compound of the formula (VIII)

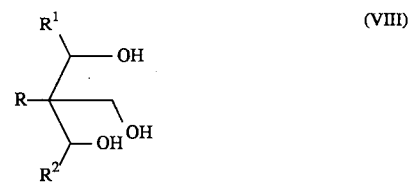 (VIII)

with a compound of the formula (AlkO)$_3$C-$A^1$CH=C(hal)$_2$ or by the cyclisation of a compound analogous to that of the formula (VI) wherein $L^1$ is a group Q.

(biii) when it is required to prepare a compound of the formula (I) wherein —AX contains a —CH=CH—C≡C—X linkage by reaction of the corresponding compound of the formula (IX)

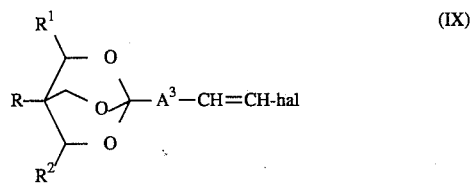 (IX)

with HC≡C—X wherein R, $R^1$, $R^2$, X and hal are as defined hereinbefore and $A^3$—CH=CH—C≡C—X is a group AX as defined hereinbefore. This reaction is carried out in the presence of a suitable palladium catalyst well known to those skilled in the art for this type of reaction, for example bis-triphenylphosphine palladium dichloride, and a catalytic amount of a cuprous halide, such as cuprous iodide. The reaction will normally be carried out in the presence of basic solvent such as diethylamine or triethylamine at a non-extreme temperature, for example between –50° and 100° C. and conveniently at 25° C. where hal is iodo or bromo.

(c) when A contains a —CONH— group, by the reaction of a compound of the formula (X):

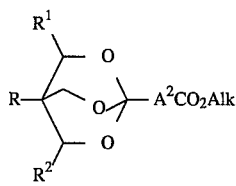
(X)

with a compound $NH_2CH_2 A^3—X$ wherein R, $R^1$, $R^2$ X are as defined hereinbefore, Alk is a group $C_{1-4}$ alkyl and $A^2CONHCH_2 A^3—X$ is a group A—X as defined hereinbefore. This reaction takes place in an inert solvent suitably an alkanol such as methanol at a non-extreme temperature, for example between 0° and 100° and preferably between 20° and 70° C., preferably in the presence of a catalyst such as sodium cyanide. The compounds of the formula (X) may be prepared by methods well known to those skilled in the art, for example as described for analogous compounds in European Patent Applications 152229 and 211598.

(d) when A contains a —COO— group, by the reaction of a compound of the formula (XI)

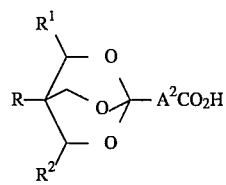
(XI)

or an alkali metal salt thereof, with a compound $X A^3 CH_2$ Hal wherein R, $R^1$, $R^2$ and X are as hereinbefore defined, hal is halogen, for example bromine or chlorine, and $A^2CO_2CH_2A^3—X$ is a group A—X as defined hereinbefore. This reaction takes place in an inert solvent suitably a dipolar aprotic solvent such as dimethylformamide at a non-extreme temperature, for example between 0° and 180° and conveniently between 0° and 30°.

(e) when A contains a —CH=NO— group, by the reaction of a compound of the formula (XII):

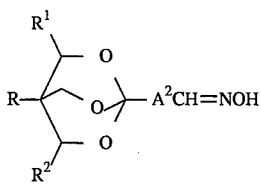
(XII)

with a compound of the formula $XC\equiv CCH_2$—hal, wherein R, $R^1$, $R^2$, X and hal are as hereinbefore defined and $A^2C=NOCH_2A^3—X$ is a group AX as defined hereinbefore. This reaction takes place in an inert solvent, suitably an alkanol such as methanol, in the presence of a base, for example an alkali metal alkoxide such as sodium methoxide, at a non-extreme temperature, for example between 0° and 80° C. and conveniently between 20° and 30° C. The compounds of the formula (XII) may be prepared by methods well known to those skilled in the art, for example as illustrated in Appendix 4.

(f) when A contains a group —OCO— by the reaction of a compound of the formula (XIII):

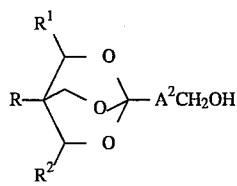
(XIII)

with a compound of the formula $XA^3CO_2H$, wherein R, $R^1$, $R^2$ and X are as defined hereinbefore and $A^2CH_2OCOA^2—X$ is a group AX as defined hereinbefore. This reaction takes place in an inert solvent, conveniently a halogenated hydrocarbon such as dichloromethane, at a non-extreme temperature, for example between 0° and 100° C. and conveniently between 20° and 30° C. The reaction preferably takes place in the presence of a coupling agent, such as carbodimide for example dicyclohexylcarbodiimide, and in the presence of a catalyst such as 4-dimethylaminopyridine. The compounds of the formula (XIII) may be prepared by methods well known to those skilled in the art, for example as described for analogous compounds in European Patent Applications 152229 and 211598.

(ii) when n is 0

$Y^1$=O or S

Y=O or S

Z=$CH_2S$ or $CH_2O$ by the reaction of a compound of the formula (XIV) with a compound of the formula $(AlkO)_3CAX$,

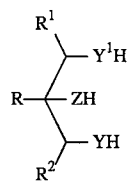
(XIV)

wherein R, $R^1$, $R^2$, A, X, Y, $Y^1$ and Z are as hereinbefore defined and Alk is a $C_{1-4}$ alkyl group. The condensation takes place in the presence of an acid catalyst for example a mineral acid such as concentrated hydrochloric acid or boron trifluoride etherate and/or p-toluenesulphonic. The reaction is conveniently carried out without a solvent, but an inert solvent, conveniently a chlorinated hydrocarbon such as dichloromethane may be added. The reaction can also be carried out in methanol containing hydrogen chloride. The reaction is conveniently carried out at a non-extreme temperature, for example between −70° C. and 150° C. and normally between −10° C. and 150° C. The compounds of the formula (XIV) may be prepared as described in European Patent Application No 216624, or as described in appendix 2. Compounds of the formula (XIV) wherein Y=$Y^1$=S, Z=$CH_2S$ and $R^1$=$R^2$=H may also be prepared by the method described by G. R. Franzen and G. Binsch, *J.Amer.Chem.Soc.*, 1973, 95, 175 and D. J. Martin and C. R. Creco, *J.Org.Chem.*, 1968, 33, 1275. The compounds of the formula $(AlkO)_3CAX$ may be prepared by a general procedure for the synthesis of orthoesters and is described by S. M. McElvain and R. E. Stam, *J.Amer.Chem.Soc.*, 1955, 77, 4571:

(iii) when Z=$CH_2S$ or $CH_2O$ and Y and $Y^1$ are sulphur by reaction of a compound of the formula (XV)

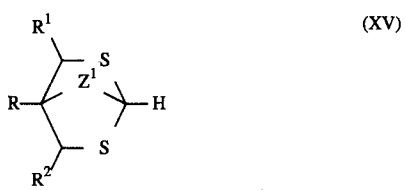

(XV)

with a compound $L^2AX$ wherein R to $R^2A$, and X are as hereinbefore defined, $Z^1$ is $CH_2S$ or $CH_2O$ and $L^2$ is a leaving group eg. halo. The reaction is suitably carried out in the presence of a strong base, such as butyllithium, in an inert solvent, such as an ether and conveniently tetrahydrofuran at a non-extreme temperature, such as between $-70°$ and $30°$ C. The compound of the formula (XV) can be prepared by the reaction of an analogous compound of the formula (XIV) with $HC(OAlk)_3$ under the conditions described for reaction (ii) above.

(iv) when Y is O and $Y^1$ is O and Z is $CH_2CH_2$ by the reaction of a compound of the formula (XVI) with acid

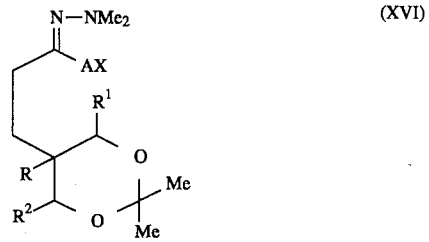

(XVI)

wherein R, $R^1$, $R^2$, A and X are as hereinbefore defined

The reaction is carried out in acidic conditions, conveniently silica gel, followed by dilute hydrochloric acid at a non-extreme temperature, i.e. between $0°$ and $100°$ and conveniently ambient temperature i.e. between $20°$ and $30°$. The compounds of the formula (XVI) may be prepared as illustrated in Appendix 3 herein.

(v) By the interconversion of compounds of the formula (I), for example a) when it is desired to prepare a compound of the formula (I) wherein A contains a terminal $C≡C$ fragment and X is other than hydrogen by the reaction of the corresponding compound wherein X is hydrogen with a compound $X^1$ Hal wherein hal is halogen and $X^1$ is other than hydrogen. This reaction is particularly suitable for the preparation of those compounds wherein X is a $C_{1-4}$ alkyl group or a group $COR^{21}$ wherein $R^{21}$ is a $C_{1-6}$ alkoxy group; or X is a substituted silyl or tin group. The reaction is normally carried out in the presence of a strong base, such as an alkyllithium conveniently butyllithium in an inert solvent, such as an ether, for example tetrahydrofuran, at a non-extreme temperature, for example between $-50°$ and $50°$ C. and conveniently between $-10°$ and $30°$ C. The starting material, i.e. the unsubstituted alkynylalkyl bicycloalkane may be prepared as described above.

(b) when it is required to prepare a compound of the formula (I) wherein A is saturated or contains a double bond by the reduction of the corresponding compound containing a double or triple bond respectively. This reaction conveniently takes place by hydrogenation in the presence of a catalyst, for example palladium on charcoal, or, when a triple bond is being reduced and it is required to stop the reduction once a double bond is formed and not proceed to the fully saturated compound, in the presence of such a catalyst poisoned by, for example, barium sulphate. The reaction is conveniently carried out in a suitable solvent for hydrogenation experiments such as methanol or ethyl acetate. The reaction is usually carried out at a non-extreme temperature, for example between $5°$ and $50°$ C. and normally at $25°$ C.

(c) when A contains a terminal $C≡C$ fragment and X is hydrogen by desilylation of a compound of the formula (XVII)

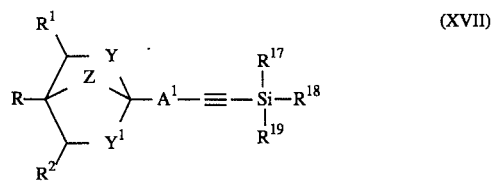

(XVII)

wherein R, $R^1$, $R^2$, $R^{17}$, $R^{18}$, $R^{19}$, Y, $Y^1$, Z and $A^1$ are as defined. This reaction may be carried out by methods well known to those skilled in the art, for example by reaction with tetrabutylammonium fluoride in an ether, such as tetrahydrofuran, at a non-extreme temperature, for example between $0°$ and $70°$ C. and conveniently at $25°$ C.

Novel chemical intermediates also form an important aspect of the present invention. Preferred intermediates include those of the formula (II), (V), (VII), (XIV) and (XV).

The compounds of formula (I) may be used to control pests such as arthropods e.g. insect and acarine pests, and helminths, i.e. nematodes. Thus, the present invention provides a method for the control of arthropods and/or helminths which comprises administering to the arthropod and/or helminth or to their environment an arthropodically effective amount of a compound of the formula (I). The present invention also provides a method for the control and/or eradication of arthropod and/or helminth infestations of animals (including humans) and/or of plants, (including trees) and/or stored products which comprises administering to the animal or locus an effective amount of a compound of the formula (I). The present invention further provides for the compounds of the formula (I) for use in human and veterinary medicine, in public health control and in agriculture for the control of arthropod and/or helminth pests.

The compounds of formula (I) are of particular value in the protection of field, forage, plantation, glasshouse, orchard and vineyard crops, of ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula I are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately 35×22×3 mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20 ppm. Space sprays may be applied to give an average initial concentration of 0.001 to 1 mg of compound of formula (I) per cubic meter of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Myzus persicae, Tetranychus urticae, Plutella xylostella,* Culex spp. *Tribolium* castaneum, Sitophilus granarius, periplaneta amiercanaand *Blattella germanica*. The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepid, Heteronychus, Phaedon, Tribolium, Sitophilus, Diabrotica, Anthonomus or Anthrenus spp.), Lepidoptera (e.g. Ephestia, Mamestra, Earias, Pectinophora, Ostrinia, Trichoplusia, Pieris, Laphygma, Agrotis, Amathes, Wiseana, Tryporysa, Diatraea, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza and Melophagus spp.), Phthiraptera (Malophaga e.g. Damalina spp. and Anoplura e.g. Linognathus and Haematopinus spp.), Hemiptera (e.g. Aphis Bemisia, Phorodon, Aeneolamia, Empoasca, Parkinsiella, Pyrilla, Aonidiella Coccus, Pseudococus, Helopeltis, Lygus, Dysdercus, Oxycarenus, Nezara Aleurodes, Triatoma, Psylla, Mysus, Megoura, Phylloxera, Adelyes Niloparvata, Nephrotetix or Cimex spp.), Orthoptera (e.g. Locusta Gryllus, Schistocerca or Acheta spp.), Dictyoptera (e.g. Blattella Periplaneta or Blatta spp.), Hymenoptera (e.g. Athalia, Cephus, Atta, Solenopsis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.), Pscoptera (e.g. Peripsocus spp.) and Thysanoptera (e.g. *Thrips tabaci*),.

Acarine pests include ticks, e.g. members of the genera Boophilus, Ornithodorus, Rhipicsphalus, Amblyomma, Hyalomma, Ixodes, Haemaphysalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia, Eriophyes, Blaniulus, Polyphagotarsonemus, Scutigerella, and Oniscus spp.

Nematodes which attack plants and trees of importance to agriculture, forestry, horticulture either directly or by spreading bacterial, viral, mycoplasma or, fungal diseases of the plants, include root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (e.g. *R. robustus*); Helicotylenchus spp. (e.g. *H. multicinctus*); Hemicycliohora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

Compounds of the invention may be combined with one or more other pesticidally active ingredients (for example pyrethroids, carbamates and organophosphates) and/or with attractants, repellents, bacteriocides, fungicides, nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1–1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

The following Examples illustrate, in a non-limiting manner, preferred aspects of the invention. All temperatures are in degrees Celsius.

EXAMPLE I 1-(Pent-4-ynyl)-4-propyl-2,6,7-trioxabicyclo[2.2.2]octane (i) To a stirred mixture of n-valeraldehyde (172 g) and water (2 l) was added solid calcium hydroxide (112 g) and formaldehyde solution (1.4 l of 40% aqueous solution). The reaction temperature was maintained below 40° and the addition took about 45 minutes. The mixture was then maintained at 60° for 5 hours. The reaction mixture was filtered through Kieselguhr and the filtrates were evaporated in vacuo. The residue was treated with hot methanol (2 l) and the mixture was filtered through Kieselguhr. The filtrates were evaporated in vacuo. A viscous oily product was obtained (458 g) and was purified as follows:

A solution of the crude product and acetic acid (200 ml) was stirred at room temperature. Acetic anhydride (1.2 l) was added over 4 hours. The temperature rose to 65°. Stirring was continued for 12 hours. The reaction mixture was added over 3 hours to cold water (3 l) with stirring. Stirring was continued for 3 hours. The aqueous mixture was extracted with diethyl ether. The ether extracts were washed with aqueous sodium hydrogen carbonate solution and then with brine. The extracts were dried over anhydrous magnesium sulphate and then evaporated in vacuo.

Distillation gave 2-hydroxymethyl-2-n-propylpropan-1,3-diol triacetate (238 g), a colourless oil (b.pt. 120°–140°, 1.5 mm Hg).

Sodium (0.5 g) was added to a stirred solution of the above triacetate (238 g) in methanol (2.5 l). The mixture was refluxed, with stirring, for 72 hours. The mixture was evaporated in vacuo.

2-Hydroxymethyl-2-n-propylpropan-1,3-diol (87 g) was obtained as colourless crystals (m.pt. 93°).

ref. W. E. Conrad, L. A. Levasseur, R. F. Murphy, N. L. Hare and H. E. Conrad. *J. ORG. CHEM* 1962.27, 2227.

(ii) A mixture of 2-hydroxymethyl-2-n-propylpropan-1,3-diol (24.6 g), diethyl carbonate (20.1 ml), potassium hydroxide (0.3 g) and dry ethanol (2 ml) was heated to gentle reflux (oil bath 110°–120°) under a stream of nitrogen for 30 minutes. After this time the ethanol formed was removed by distillation at atmospheric pressure (oil bath 130°–140°, still head temperature 76°). The pressure was reduced to 20 mmHg and the oil bath temperature adjusted to 230°. 3-Hydroxymethyl-3-n-propyloxetane distilled as a colourless liquid (16.7 g) (head temperature 120°–126°).

ref. European Patent Application 216624.

(iii) A solution of 5-chloro-1-pentyne (Aldrich Chemical Company, 20 g) and potassium cyanide (19 g) in 20% aqueous ethanol (120 ml.) was heated under reflux for 20 hours. Water (600 ml) was then added and the resulting mixture was extracted with diethyl ether. The combined ethereal extracts were washed with water and then with brine. The extracts were dried over anhydrous magnesium sulphate and then evaporated in vacuo. Distillation gave 5-cyano-1-pentyne (9.9 g) as a colourless oil (b.p. 67°–68°, 15 mm Hg).

(iv) A mixture of 5-cyano-1-pentyne (9.9 g) and 10% aqueous potassium hydroxide solution (100 ml) was heated under reflux for 6 hours. The resulting solution was extracted with chloroform. The aqueous phase was acidified to pH 1 with concentrated hydrochloric acid and then re-extracted with dichloromethane. The dichloromethane extracts were washed with brine, dried over anhydrous magnesium sulphate and then evaporated in vacuo.

Distillation gave hex-5-ynoic acid (9.9 g) as a colourless liquid (b.p. 66°–67°, 0.6 mmHg.).

(v) A mixture of hex-5-ynoic acid (1 g) and thionyl chloride (1.95 ml) in benzene (25 ml) was heated under reflux for 3 hours. The resulting solution was cooled and then evaporated in vacuo. The acid halide thus obtained was taken up in ether (5 ml) and added, dropwise, to a stirred solution of 3-hydroxymethyl-3-n-propyloxetane (1.2 g) and pyridine (0.8 ml) in dry ether (20 ml.). The reaction mixture was stirred at room temperature for 16 hours. After this time the organic phase was washed with water, 5% hydrochloric acid, saturated sodium bicarbonate solution and brine before drying over anhydrous magnesium sulphate and then evaporation in vacuo. The residue was purified by chromatography on silica, pre-eluted with hexane containing 1% triethylamine. Elution with hexane/ether mixtures gave (3-propyloxetan-3-yl)methyl hex-5-ynoate (1.33 g) as a colourless oil.

Gas-liquid chromatography (g.l.c.): OV-17 at 175° produced one peak.

Nuclear magnetic resonance spectrum (NMR) was as follows: $^1$H (p.p.m. from TMS in $CDCl_3$, integral, number of peaks,): 4.45, 4H, s; 4.20, 2H, s; 2.8–0.8, 14H, m.

(vi) Boron trifluoride etherate (0.18 ml) was added to a stirred solution of (3-propyloxetan-3-yl)methyl hex-5-ynoate (1.33 g.) in dry dichloromethane (25 ml) at –70°. The mixture was allowed to warm to room temperature over 16 hours. Triethylamine (0.28 ml) was then added and the solvent was removed in vacuo. The residue was partitioned between diethyl ether and water. The organic phase was separated and further washed with water and brine before drying over anhydrous magnesium sulphate. The solvent was evaporated in vacuo and the residue was purified by column chromatography on alumina eluting with 1:6 dichloromethane:hexane saturated with ammonia. 1-(Pent-4-ynyl)-4-propyl-2,6,7-trioxabicyclo[2.2.2]octane was obtained as a colourless oil which crystallised on trituration (0.64 g) with hexane.

Gas-liquid chromatography (g.l.c): OV-17 at 200° produced one peak.

EXAMPLE II 1-(Hex-5-ynyl)-4-propyl-2,6,7-trioxabicyclo[2.2.2]octane.

(i) A solution of methanesulphonyl chloride (23.7 ml) in dry dichloromethane (25 ml.) was added dropwise to a solution of hex-5-yn-1-ol (Lancaster Synthesis, 25 g) and triethylamine (47.3 ml) in dichloromethane (300 ml), stirred under a nitrogen atmosphere at –70°. The resulting mixture was allowed to warm to room temperature over 16 hours. The mixture was then washed with water, dilute hydrochloric acid, saturated sodium bicarbonate solution and brine before drying over anhydrous magnesium sulphate and evaporation in vacuo.

Hex-5-ynyl methanesulphonate was obtained as an oil (43.6 g) and was used without purification.

OTHER PUBLICATIONS

Nuclear magnetic resonance spectrum (NMR) was as follows: $^1$H (p.p.m from TMS in CDCl$_3$, integral, number of peaks, $J_{Hz}$): 4.15, 2H, t, $J_{Hz}$ 6; 3.0, 3H, s; 2.4–1.4, 7H, m.

(ii) A mixture of hex-5-ynyl methanesulphonate (43.6 g) and potassium cyanide (24 g) in 20% aqueous ethanol (150 ml) was heated Under reflux for 4 hours and then stirred at room temperature overnight. Water (600 ml) was added and the mixture was extracted with diethyl ether. The organic extracts were washed with water and brine before drying over anhydrous magnesium sulphate and evaporation in vacuo.

Distillation gave 6-cyano-1-hexyne (20.1 g) as a colourless oil (b.p. 82°–95°, 15 mm Hg)

Infrared spectrum (IR) (liquid film): 3340, 2990, 2920, 2300, 2160, 1485, 1450, 1355, 670 cm$^{-1}$.

(iii) Using the method described in stage (iv) of Example I, 6-cyano-1-hexyne was converted into hept-6-ynoic acid (b.p. 78°–82°, 0.75 mm Hg).

Infrared spectrum (IR) (liquid film): 3340, 2980, 2160, 1730, 1435, 1310, 1255, 955, 660 cm$^{-1}$.

(iv) Using the methodology described in stages (v) and (vi) of Example I, 1-(Hex-5-ynyl)-4-propyl-2,6,7-trioxabicyclo[2.2.2]octane was prepared from hept-6-ynoic acid and 3-hydroxymethyl-3-n-propyl oxetane.

Gas-liquid chromatography (g.l.c): OV-17 at 175° produced one peak.

In an analogous manner the following compound was also prepared: 1-(Oct-7-ynyl)-4-propyl-2,6,7-trioxabicyclo [2.2.2]octane from oct-7-yn-1-ol (ref British patent 969,816, *Chem. Abs*, 1965, 62, 1571f).

EXAMPLE III 1-(Pent-4-ynyl)-4-propyl-3-trifluoromethyl-2,6,7-trioxabicyclo[2.2.2]octane (i) A mixture of hex-5-ynoic acid (1 g) and thionyl chloride (1.95 ml) in benzene (25 ml) was heated at reflux for 2.5 hours. The resulting solution was cooled and then evaporated in vacuo. The acid chloride thus obtained was taken up in dry diethyl ether (5 ml) and added, dropwise, to a stirred solution of 3-(1-hydroxy-2,2,2-trifluoroethyl)-3-n-propyloxetane (1.77 g) (European Patent Application No. 211598) and pyridine (0.8 ml) in ether (20 ml). The reaction mixture was allowed to stir at room temperature overnight. After washing with water, dilute hydrochloric acid, saturated sodium bicarbonate solution and brine, the organic phase was dried over anhydrous magnesium sulphate and then evaporated in vacuo. The residue was purified by chromatography on silica, pre-eluted with hexane containing 1% triethylamine. Gradient elution with hexane/ether mixtures gave 2,2,2-trifluoro-1-(3-propyloxetan-3-yl)ethyl hex-5-ynoate (1.2 g) as a colourless oil.

Gas-liquid chromatography (g.l.c): OV-17 at 175° produced one peak.

Nuclear magnetic resonance spectrum (N.M.R) was as follows $^1$H (p.p.m from TMS in CDCl$_3$, integral, number of peaks,) 4.8–4.1, 5H, m; 2.7–0.8, 14H,m.

(ii) Using the method described in stage (vi) of Example I and starting from 2,2,2-trifluoro-1-(3-propyloxetan-3-yl)ethyl hex-5-ynoate, 1-(pent-4-ynyl)-4-propyl-3-trifluoromethyl-2,6,7-trioxabicyclo[2.2.2]-octane was obtained as a white crystalline solid.

Gas-liquid chromatography (g.l.c): OV-17 at 170° produced one peak.

In an analogous manner the following compound was prepared from hept-6-ynoic acid and 3-(1-hydroxy-2,2,2-trifluoroethyl)-3-n-propyloxetane: 1-(Hex-5-ynyl)-4-propyl-3-trifluoromethyl-2,6,7-trioxabicyclo[2.2.2]octane.

EXAMPLE IV 1-(Pent-4-ynyl)-4-propyl-2.6.7-trioxabicyclo[2.2.2] octane-3-carbonitrile (i) A solution of dimethyl sulphoxide (12 ml) in dry dichloromethane (4.0 ml) was added to a solution of oxalyl chloride (7.4 ml) in dichloromethane (25 ml) stirred at −70° under nitrogen. After the addition was complete the resulting mixture was stirred for a further 5 minutes at −70° before a solution of 3-hydroxymethyl-3-n-propyl oxetane (10.0 g) in dichloromethane (25 ml) was added, dropwise, over 10 minutes. The resulting mixture was allowed to stir for a further 30 minutes when neat triethylamine (54 ml) was added over approximately 30 minutes. The reaction mixture was allowed to warm to room temperature over 3 hours when it was poured into water. The organic phase was separated and the aqueous layer was further extracted with dichloromethane. The combined organic extracts were washed with dilute hydrochloric acid, saturated sodium bicarbonate and brine. The resulting organic phase was dried over anhydrous magnesium sulphate and evaporated in vacuo to give 3-formyl-3-n-propyloxetane (10.5 g) (European Patent Application No. 216624) as a yellow oil.

(ii) A mixture of hex-5-ynoic acid (1 g) and thionyl chloride (1.95 ml) in benzene (25 ml) was heated at reflux for 3 hours. The resulting solution was allowed to cool and then evaporated in vacuo. The acid chloride thus obtained was added to a stirred solution of 3-formyl-3-n-propyloxetane (1.14 g) in ether (50 ml) followed by a solution of sodium cyanide (0.61 g) in water (1 ml). The resulting mixture was stirred briskly at room temperature for 16 hours. After this time the reaction mixture was washed with water, saturated sodium bicarbonate and brine, before drying over anhydrous magnesium sulphate. The solvent was removed in vacuo and the residue was purified by column chromatography on silica, pre-eluted with hexane containing 1% triethylamine. Gradient elution with hexane/ether mixtures gave 1-cyano-1-(3-propyloxetan-3-yl) methyl hex-5-ynoate as a colourless oil (1.2 g).

Gas-liquid chromatography (g.l.c): OV-17 at 175° produced one peak. Nuclear magnetic resonance spectrum (NMR) was as follows: $^1$H (p.p.m from TMS in CDCl$_3$, integral, number of peaks): 5.6, 1H, s; 4.75–4.4, 4H, m; 2.8–0.9, 14H, m.

(iii) Boron trifluoride etherate (0.25 ml) was added to a solution of 1-cyano-1-(3-propyloxetan-3-yl)methyl hex-5-ynoate (0.5 g) in dry dichloromethane (10 ml) stirred at −70° under a nitrogen atmosphere. The resulting solution was allowed to warm to room temperature overnight. Triethylamine (0.38 ml.) was added and the solvent was removed under vacuum. The residue was partitioned between water and diethyl ether. The organic phase was separated and washed with water and brine before drying over anhydrous magnesium sulphate and evaporation in vacuo. The residue was purified by column chromatography on alumina eluting with 1:4 dichloromethane:hexane saturated with ammonia. 1-(Pent-4-ynyl)-4-propyl-2,6,7-trioxabicyclo[2.2.2]octane-3-carbonitrile was obtained as an oil (0.25 g). Gas-liquid chromatography (g.l.c): OV-17 at 175° produced one peak.

In an analogous manner the following compounds were prepared 1-(Hex-5-Ynyl)-4-propyl-2,6,7-trioxabicyclo[2.2.2]octane-3-carbonitrile 4n-Butyl-1-(hex-5-ynyl)-2,6,7-trioxabicyclo[2.2.2]octane-3-carbonitrile 4-t-Butyl-1-(hex-5-ynyl)-2,6,7-trioxabicyclo[2.2.2]octane-3-carbonitrile (Preparation of 2-t-butyl-2-hydroxymethylpropan-1,3-diol, Y. Ozoe and M. Eto, *Agric. Biol.Chem.* 1982, 46, 411).

4-Cyclopropylmethyl-1-(hex-5-ynyl)-2,6,7-trioxabicyclo[2.2.2]octane-3-carbonitrile, 1-(hex-5-ynyl)-4-phenyl-2,6,7-trioxabicyclo[2.2.2]-octane-3-carbonitrile, 1-(hex-5-ynyl)-4-i-butyl-2,6,7-trioxabicyclo[2.2.2]octane-3-carbonitrile and 1-(hex-5-ynyl)-4-(2-methylprop-2-enyl)- 2,6,7-trioxabicyclo[2.2.2]octane-3-carbonitrile were prepared from 3-cyclopropylmethyl-3-formyloxetane, 3-formyl-3-phenyloxetane, 3-formyl-3-1-butyloxetane and 3-formyl-3-(2-methylprop-2-enyl)oxetane respectively. 3-Cyclopropylmethyl-3-formyloxetane, 3-formyl-3-phenyloxetane, 3-formyl-3-i-butyloxetane and 3-formyl-3-(2-methylprop-2-enyl)oxetane were prepared from diethyl cyclopropylmethylmalonate (J. A. Arvin and R. Adams, *J. Amer. Chem. Soc,* 1928, 50, 1985), diethyl phenylmalonata (Aldrich), diethyl i-butylmalonate (Bellstein. 2, 683) and diethyl 2-methylprop-2-enylmalonate (W. J. Doran and H. A. Shonle, *J. Amer. Chem. Soc.* 1937, 59, 1625) using methodology described in Example V [except that toluene replaced tetrahydrofuran as solvent in stage (i)]

EXAMPLE V

4-Cyclohexyl-1-(pent-4-ynyl)-2,6,7-trioxabicyclo[2,2,2]octane (i) Diethyl cyclohexylmalonate (18.7 g) (ref. Bailstein 9, 739) was added to a stirred suspension of sodium hydride (4.8 g., 50% dispersion in oil) in dry tetrahydrofuran (50 ml) under nitrogen. The mixture was refluxed, with stirring, for one hour. The mixture was cooled and benzyl chloromethyl ether (13.9 g.) (Sigma Chemical Company) in dry tetrahydrofuran (50 ml) was added and the mixture was refluxed, with stirring, for three hours. The mixture was cooled and poured into water. The aqueous mixture was extracted with ether. The ether extracts were washed with water, dried over anhydrous magnesium sulphate and evaporated in vacuo. Diethyl 2-benzyloxymethyl-2cyclohexylmalonate (30 g.) was obtained as a brown oil and was used without further purification.

(ii) Diethyl 2-benzyloxymethyl-2-cyclohexylmalonate (2 g.) was added to a suspension of lithium aluminium hydride (0.63 g.) in dry ether (30 ml), at 0° under nitrogen. The mixture was stirred at room temperature for twelve hours. Water (5 ml) was added carefully and the mixture was stirred for ten minutes. 10% sulphuric acid solution (10 ml) was added and the mixture was extracted with ether. The ether extracts were washed with water, dried over anhydrous magnesium sulphate and evaporated in vacuo. The residue was purified by chromatography on silica, eluting with 1:1 ether:hexane. 2-Benzyloxymethyl- 2-cyclohexylpropan-1,3-diol was obtained as a colourless oil (1.0 g.).

(iii) 2-Benzyloxymethyl-2-cyclohexyl-propan-1,3-diol (5.5 g.) in dry diethyl ether (50 ml.) was added to liquid ammonia (200 ml) at −70°. Sodium (2.5 g.) was added to the stirred solution. Stirring was maintained at −70° for 1 hour. The mixture was allowed to warm up to 0° and solid ammonium chloride (15 g.) was added cautiously. The ammonia was removed from the reaction mixture under a current of nitrogen. Methanol (25 ml.) was added to the stirred mixture to destroy residual sodium. Dichloromethane (400 ml) was added and the mixture was filtered. The filtrates were evaporated in vacuo. 2-Cyclohexyl-2-hydroxymethylpropan-1,3-diol was obtained as a colourless solid (3.2 g.).

(iv) A mixture of 2-cyclohexyl-2-hydroxymethylpropan-1,3-diol (3.76 g), ethyl carbonate (2.42 ml) and a solution of potassium hydroxide in ethanol (0.1 ml of a solution of 5 g in 25 ml) was refluxed for 20 minutes. The apparatus was converted to distillation. Ethanol was removed by distillation (78°–80° C. at 760 mm Hg). When all the ethanol had been removed the residue was distilled at reduced pressure. 3-Cyclohexyl-3-hydroxymethyloxetane (European Patent Application No. 216624) distilled as a colourless oil.

(v) Using the methods described in stages (v) and (vi) of Example I, 4-cyclohexyl-1-(pent-4-ynyl)-2,6,7-trioxabicyclo[2.2.2]octane was prepared from hex-5-ynoic acid and 3-cyclohexyl-3-hydroxymethyl oxetane.

Gas-liquid chromatography (g.l.c): OV-17 at 230° produced one peak.

In an analogous manner 4-cyclohexyl-1-(hex-5-ynyl)-2,6,7trioxabicyclo[2.2.2]octane, was prepared from hept-6-ynoic acid.

EXAMPLE VI 4-t-Butyl-1-(hex-5-ynyl)-2,6,7-trioxabicyclo[2.2.2]octane

Method 1

Using the procedure described in stage (vi) of Example I and starting from hept-6-ynoic acid and 3-t-butyl-3-hydroxymethyloxetane (2-t-butyl- 2-hyddroxymethylpropan-1,3-diol was prepared by the method of Y. Ozoe and M. Eto *Agric.Biol. Chem,* 1982, 46, 411), 4-t-butyl-1-(hex-5-ynyl)-2,6,7-trioxabicyclo[2.2.2]octane was prepared.

Gas-liquid chromatography (g.l.c.): OV-17 at 230° produced one peak.

Method 2

A mixture of 2-t-butyl-2-hydroxymethylpropan-1,3-diol (0.75 g) and trimethyl orthohept-6-ynoate (0.75 g) (see Example XI) was heated at 50° until homogeneous. One drop of concentrated hydrochloric acid was added and the mixture was heated at 135° under a current of nitrogen for 10 minutes. The mixture was cooled and chromatographed on alumina, eluting with 1:6 dichloromethane: hexane saturated with ammonia.

4-t-Butyl-1-(hex-5-ynyl)-2,6,7-trioxabicyclo[2.2.2]octane was obtained as colourless crystals (0.38 g, recrystallised from hexane).

In an analogous manner 1-(hex-5-ynyl)-4-phenyl-2,6,7-trioxabicyclo[2.2.2]-octane was prepared from 2-hydroxymethyl-2-phenylpropan-1,3-diol (prepared from diethyl 2-phenylmalonate using methodology described in Example V).

EXAMPLE VII

4-t-Butyl-1-(6-trimethylsilylhex-5-ynyl)-2,6,7-trioxabicyclo[2.2.2]octane n-Butyllithium (0.31 ml. of 1.6M solution, in hexane) was added to a stirred solution of 4-t-butyl-1-(hex-5-ynyl)-2,6,7-trioxabicyclo[2.2.2]octane (100mg) in dry tetrahydrofuran (4.0 ml), at 0°, under nitrogen. The reaction mixture was stirred at 0° for 15 minutes. Trimethylsilyl chloride (63 µl) was added and the mixture was allowed to warm up to 20° over a period of 2 hours. Water (0.5 ml) was added and the solvent was removed in vacuo. Water was added and the aqueous mixture was extracted with diethyl ether. The ethereal extracts were washed with brine and dried over anhydrous magnesium sulphate. The solvent was removed in vacuo. The residue was purified by chromatography on alumina (Alumina Woelm TSC) eluting with 1:6 dichloromethane:hexane saturated with ammonia.

4-t-Butyl-1-(6-trimethylsilylhex-5-ynyl)-2,6,7-trioxabicyclo[2.2.2]octane was obtained as colourless crystals (60mg) (m.p. 87°–90.5°). Gas-liquid chromatography (g.l.c.): OV-17 at 230° produced one peak.

EXAMPLE VIII

1-(4-Ethynylcyclohexyl)-4-propyl-2,6,7-trioxabicyclo[2.2.2]octane (i) To a stirred solution of dimethyl 1, 4-cyclohexanedicarboxylate (20 g, Aldrich) in methanol (50 ml) was added a solution of potassium hydroxide (7.3 g) in methanol (75 ml). The reaction mixture was refluxed for 16 hours. After cooling the solvent was removed on a rotary evaporator. The residue was taken up in ether and water and extracted to remove unreacted starting diester. The aqueous layer was acidified with dilute hydrochloric acid and re-extracted with ether.

The ether extracts were washed with brine and dried. Evaporation in vacuo gave a solid. Purification was achieved by recrystallization from ethyl acetate to yield 4-methoxycarbonylcyclohexanecarboxylic acid (6.2 g), m.pt 90.9° C.

Ref J. D. Roberts et al , J Amer. Chem. Soc., 1953, 75, 637

(ii) Thionyl chloride (3.65 ml) was added to a stirred solution of 4-methoxycarbonylcyclohexanecarboxylic acid (5.6 g) in dry benzene (50 ml). The reaction mixture was heated to gentle reflux in an oil bath for 4 hours. The resulting solution was cooled and then evaporated in vacuo. The acid halide thus obtained was redissolved in benzene and further evaporated in vacuo. This material was used in the next stage without further purification.

Infrared Spectrum (IR) (liquid film), 1790(s), 1720(s) cm$^{-1}$.

(iii) Zinc borohydride solution (67 ml of a 0.35M solution, Ref. W. J. Gensler et al J. Amer. Chem. Soc. 1960, 82, 6074) and tetramethylethylenediamine (TMEDA) were successively added to a stirred solution of 4-methoxycarbonylcyclohexylcarbonyl chloride (1.02 g) in THF (18 ml) at 0° C. The reaction mixture was stirred at 0° C. for 30 minutes. The organic phase was then washed with dilute hydrochloric acid and brine before drying over anhydrous magnesium sulphate and then evaporation in vacuo. Methyl 4-hydroxymethylcyclohexanecarboxylate was obtained as a semi-crystalline oil.

Infrared Spectrum (IR) (liquid film), 3400 (s.br), 1720 (s)cm$^{-1}$.

Gas-liquid chromatography (g.l.c); OV17 at 110° C. produced 2 peaks (cis-, trans-isomers, –1:1).

(iv) Dimethyl sulphoxide (0.65 ml) in dry dichloromethane (5 ml) was added to a solution of oxalyl chloride (0.363 ml) in dichloromethane (5 ml) at –70° C. under a stream of nitrogen. After 5 minutes stirring a solution of methyl 4-hydroxymethylcyclohexanecarboxylate (0.64 g) in dichloromethane (5 ml) was added dropwise. The reaction mixture was stirred for 30 minutes at –70° C. Triethylamine (2.60 ml) was then added and the reaction mixture allowed to warm to room temperature during a period of 3 hours. After pouring into water (100 ml) the organic phase was washed with dilute hydrochloric acid, sodium bicarbonate solution and brine before drying over magnesium sulphate. Evaporation in vacuo gave methyl 4-formylcyclohexanecarboxylate (0.58 g) as a mixture of cis- and trans-isomers.

Infrared Spectrum (IR) (liquid film), 1720 cm$^{-1}$(s).

Gas-liquid chromatography (glc); OV17 at 120° C. produced only 1 peak.

Mass Spectrum (MS), chemical ionisation : M+1 171.

(v) A solution of carbon tetrabromide (1.66 g) in dry dichloromethane (10 ml) was added to a stirred solution of triphenyl phosphine (2.62 g) in dry dichloromethane (10 ml) with cooling. To this orange solution was added a solution of methyl 4-formylcyclohexanecarboxylate (0.85 g) in dry dichloromethane (10 ml) under a current of nitrogen. The reaction mixture was stirred at room temperature overnight. The solvent was then removed in vacuo. The residue was mechanically stirred with hexane for 1 hour. Filtration gave a colourless solution. Evaporation gave a colourless oil of methyl 4-(2,2-dibromovinyl) cyclohexanecarboxylate (1.15 g) as a mixture of cis- and trans-isomers.

Infrared Spectrum (IR) (liquid film), 1722 cm$^{-1}$

Gas liquid chromatography (glc); OV17 at 155° C. produced 2 peaks (cis- and trans-isomers, –1:1).

Mass Spectrum (MS), Chemical Ionisation, (2 peaks glc/MS), both M+1, 325.

(vi) Methyl 4-(2,2-dibromovinyl) cyclohexanecarboxylate (1.15 g) was added to a stirred solution of potassium hydroxide (297 mg) in methanol (2 ml). After stirring overnight the solvent was evaporated in vacuo. The residue was partitioned between diethyl ether and water. The aqueous layer was separated and acidified with dilute hydrochloric acid. Extraction with diethyl ether gave a solution which was washed with brine and then dried over anhydrous magnesium sulphate. Evaporation in vacuo gave 4-(2,2-dibromovinyl)cyclohexanecarboxylic acid (0.86 g) as a colourless solid.

Infrared Spectrum (IR)(Nujol mull), 1690 (s), cm$^{-1}$.

(vii) Thionyl chloride (0.67 ml) was added to a stirred solution of 4-(2,2-dibromovinyl)cyclohexanecarboxylic acid (0.86 g) in dry benzene (25 ml). The reaction mixture was heated to gentle reflux in an oil bath for 4 hours. The resulting solution was cooled and then evaporated in vacuo. The acid halide thus obtained was redissolved in benzene and further evaporated en vacuo. 4-(2,2-dibromovinyl)cyclohexanecarbonyl chloride (0.91 g) was obtained as a pale yellow oil.

Infrared spectrum (IR)(liquid film), 1790(s) cm –1.

(viii) 4-(2,2-Dibromovinyl)cyclohexanecarbonyl chloride (0.91 g) in dry dichloromethane (5 ml) was added to a cooled (0° C.) solution of 3-propyl- 3-hydroxymethyloxetane (0.406 g) and pyridine (0.64 ml) in dry dichloromethane (10 ml) under a stream of nitrogen. The reaction mixture was allowed to warm to room temperature and to stir overnight.

Further dichloromethane was added. The organic phase was then washed with dilute hydrochloric acid, saturated sodium bicarbonate solution and brine before drying over anhydrous magnesium sulphate. The solvent was evaporated in vacuo and the residue was purified by column chromatography on silica gel, pre-eluted with hexane containing 1% triethylamine. Elution with hexane/ether (3:1) gave 3-propyloxetan- 3-ylmethyl 4-(2,2-dibromovinyl)cyclohexanecarboxylate (0.6 g) as a mixture of cis- and trans-isomers.

Infrared Spectrum (IR)(liquid film), 1722 (s) cm −1

Mass spectrum (MS), chemical ionisation, 2 peaks in glc/ms in a ratio of 3:1, both M+1 423.

(ix) Boron trifluoride etherate (40 μl) was added to a stirred solution of 3-propyloxetan-3-ylmethyl 4-(2,2-dibromovinyl)cyclohexanecarboxylate (0.57 g) in dry dichloromethane (10 ml) at −70° C. The mixture was allowed to warm to room temperature over 16 hours. Triethylamine (0.6 ml) was then added. The organic phase was washed with brine before drying over anhydrous magnesium sulphate. The solvent was evaporated in vacuo and the residue was purified by column chromatography on alumina eluting with 3:7 dichloromethane:hexane saturated with ammonia. 1-[4-(2,2-Dibromovinyl)cyclohexyl]-4-propyl-2,6,7-trioxabicyclo[2.2.2]octane was obtained as a colourless oil (0.34 g).

Infrared spectrum (IR)(liquid film), 1060, 1020 cm$^{-1}$

Mass spectrum (MS), chemical ionisation, 2 peaks in glc/ms in a ratio of 3:1, both M+1 423.

(x) n-Butyllithium (1.6 ml of a 1.1M solution in hexane) was added at −70° C. to a solution of 1-[4-(2,2-dibromovinyl)cyclohexyl]-4-propyl-2,6,7-trioxabicyclo[2.2.2]octane (0.25 g) in dry tetrahydrofuran (5 ml) under a stream of nitrogen. After warming to room temperature over 2 hours ether (~25 ml) was added. The ethereal solution was washed with brine and dried over anhydrous magnesium sulphate. The solvent was removed in vacuo and the residue was purified by column chromatography on alumina eluting with 3:7 dichloromethane:hexane saturated with ammonia. 1-(4-Ethynylcyclohexyl)-4-propyl-2,6,7-trioxabicyclo[2.2.2]octane was obtained as a colourless oil (0.13 g).

EXAMPLE IX 4-t-Butyl-1-(4-Ethynylcyclohexyl)-2,6,7-trioxabicyclo[2.2.2]octane

Method 1

(i) Using the method described in stage (viii) of Example VIII and starting from 4-(2,2-dibromovinyl)cyclohexanexcarbonyl chloride and 3-t-butyl-3-hydroxymethyloxetane,3-t-butyloxetan-3-ylmethyl 4-(2,2-dibromovinyl)cyclohexane carboxylate was prepared as a mixture of cis- and trans-isomers.

(ii) Using the method described in Stage (ix) of Example VIII and starting from 3-t-butyloxetan-3-ylmethyl 4-(2,2-dibromovinyl)cyclohexane carboxylate,4-t-butyl-1-[4-(2,2-dibromovinyl)cyclohexyl]-2,6,7-trioxabicyclo[2.2.2]octane was obtained as a colourless oil, as a mixture of cis- and trans-isomers.

(iii) Using the method described in Stage (x) of Example VIII and starting from 4-t-butyl-1-[4-(2,2-dibromovinyl)cyclohexyl]-2,6,7-trioxabicyclo[2.2.2]octane, 4-t-butyl-1-(4-ethynylcyclohexyl)-2,6,7-trioxabicyclo[2.2.2]octane was obtained as a colourless solid, (m.pt 125.9°–131.8° C.) as a mixture of cis and trans isomers.

Both cis and trans 4-t-butyl-1-(4-ethynylcyclohexyl)-2,6,7-trioxabicyclo[2.2.2]octane were obtained as follows:

(a) cis and trans Methyl 4-(2,2-dibromovinyl)cyclohexanecarboxylate

Chromatographic separation of a mixture of cis- and trans- isomers of methyl 4-(2,2-dibromovinyl)cyclohexanecarboxylate (Example VIII, stage (v)), on silica gel, eluting with ether (10%) in hexane gave cis and trans methyl 4-(2,2-dibromovinyl)cyclohexanecarboxylate as colourless oils.

(b) cis-4-(2,2-Dibromovinyl)cyclohexanecarboxylic acid cis-Methyl 4-(2,2-dibromovinyl)cyclohexanecarboxylate (4 g) was heated to reflux in a solution of hydrobromic acid (48%, 20 ml) and acetic acid (40 ml). After heating for 4 hours the solvent was removed under reduced pressure. Water (50 ml) was added and the mixture extracted with diethyl ether. The ether extracts were extracted with sodium bicarbonate solution. The aqueous layer was then acidified and re-extracted with ether. The ethereal layer washed with brine and dried over anhydrous magnesium sulphate. Evaporation gave cis-4-(2,2-dibromovinyl)cyclohexanecarboxylic acid (3.6 g) as a pale yellow oil.

(c) trans-4-(2,2-Dibromovinyl)cyclohexanecarboxylic acid trans-Methyl 4-(2,2-dibromovinyl)cyclohexanecarboxylate (4.2 g) was stirred in a solution of potassium hydroxide (1.09 g) in methanol (50 ml) overnight. The solvent was then removed under reduced pressure. Water (50 ml) was added and the mixture extracted with diethyl ether. The aqueous layer was then acidified with hydrochloric acid. Re-extraction with ether was followed by washing of the organic layer with brine and drying over anhydrous magnesium sulphate. Evaporation gave trans-4-(2,2-dibromovinyl)cyclohexanecarboxylic acid (3.6 g) as a pale yellow oil.

(iv) cis- and trans-4-(2,2-dibromovinyl)cyclohexanecarboxylic acids were then converted into cis- and trans-4-t-butyl-1-(4-ethynylcyclohexyl)-2,6,7-trioxabicyclo[2.2.2]octanes respectively using methods described in stages (vii), (viii), (ix) and (x) of Example VIII.

4-t-Butyl-(4-ethynylcyclohexyl)-2,6.7-trioxabicyclo[2.2.2]octane

Method 2

(i) Di-isopropylamine (44.7 ml) was dissolved in dry tetrahydrofuran (400 ml) and cooled to −78° C. under nitrogen with mechanical stirring. A solution of B-butyllithium in hexane (1.6M, 197 ml) was added. After stirring at −78° C. for 10 minutes a solution of dimethyl cyclohexane-1,4-dicarboxylate (56.6 g, Lancaster) in tetrahydrofuran (200 ml) was added. After stirring for a further 30 minutes at −78° C. a solution of acetyl chloride (22.5 ml) in tetrahydrofuran (200 ml) was added. The reaction mixture was allowed to warm up to room temperature over a period of 3 hours. Water was then added and the mixture extracted with ether. The ethereal extracts were washed with water, saturated sodium bicarbonate solution, dilute hydrochloric acid and brine, and then were dried over anhydrous magnesium sulphate. Evaporation under reduced pressure gave a colourless oil which was slowly distilled to yield dimethyl 1-acetylcyclohexane-1,4-dicarboxylate (23.3 g, b.pt. 114°–120 C. at 0.4 mmHg).

OTHER PUBLICATIONS

Infrared spectrum (IR) (liquid film) 1740, 1710 cm$^{-1}$ (ii) Dimethyl 1-acetylcyclohexane-1,4-dicarboxylate (23.3 g) was added to a solution of concentrated hydrochloric acid (253 ml) in ethanol (126 ml). After refluxing for 10 hours the reaction mixture was poured into water and then extracted with dichloromethane. The organic phase was then washed with saturate sodium bicarbonate solution and brine. After drying over anhydrous magnesium sulphate the solvent was removed under reduced pressure to give methyl 4-acetylcyclohexanecarboxylate as a colourless oil. This was purified by distillation (b.pt 138°–145° C. at 14 mmHg).

Infrared spectrum (IR) (liquid film) 1730, 1710 cm$^{-1}$.

(iii) Using the method described in Stage (ii) of Example XVIII, and starting from methyl 4-acetylcyclohexancarboxylate, methyl 4-(1-chloroethenyl) cyclohexanecarboxylate was prepared.

Infrared spectrum (IR) (liquid film), 1730cm$^{-1}$ (iv) Using the method described in Stage (iii) of Example XVIII, and starting from methyl 4-(1-chloroethenyl)cyclohexanecarboxylate, 4-(1-chloroethenyl)cyclohexylmethanol was prepared.

Infrared Spectrum (IR) (liquid film), 3400cm$^{-1}$.

(v) Using the method described in Stage (iv) of Example XVIII, and starting from 4-(1-chloroethenyl)cyclohexylmethanol, 4-ethynylcyclohexylmethanol was prepared.

Infrared Spectrum (IR) (liquid film) 3420, 3290 cm
Mass spectrum, MS, (Electron impact), M+1, 139

(vi) Using the method described in Stage (v) of Example XVIII, and starting from 4-ethynylcyclohexanemethanol, 4-ethynylcyclohexanecarboxylic acid was prepared.

Infrared Spectrum (IR) (nujol mull), 3290, 1705cm$^{-1}$.
Mass spectrum, (MS), (Electron impact), M+1, 153.

Using the method described in Example I and starting from 4-ethynylcyclohexanecarboxylic acid and 3-t-butyl-3-hydroxymethyl-oxetane, 4-t-butyl-1-(4-ethynylcyclohexyl)-2,6,7-trioxabicyclo[2.2.2]octane was prepared.

Using the methodology described in Example IV and starting from 3-formyl-3-n-propyloxetane and 4-ethynylcyclohexanecarboxylic acid, 1-(4-ethynylcyclohexyl)-4-n-propyl-2,6,7-trioxabicyclo[2.2.2]octane-3-carbonitrile was prepared.

EXAMPLE X 4-t-Butyl-1-(3,3-dimethylbut-1-ynyl)-2,6,7-trioxabicyclo[2.2.2]octane (i) Using the method described in stage (viii) of Example VIII and starting from 4,4-dimethyl-2-pentynoyl chloride (A R Katritsky et al, *J Chem. Soc., Perkin Trans 2*, 1974, 282), and 3-t-butyl-3-hydroxymethyloxetane, (3-t-butyloxetan-3-yl)methyl 4,4-dimethylpent-2-ynoate was obtained as a solid.

Gas-liquid chromatography (glc) : OV17 at 180° C. produced one peak.

(ii) Using the method described in Stage (ix) of Example VIII and starting from (3-t-butyloxetan-3-yl)methyl 4,4-dimethylpent-2-ynoate, 4-t-butyl-1-(3,3-dimethylbut-1-ynyl)-2,6,7-trioxabicyclo[2.2.2]octane was obtained as colourless crystals (m pt 204°–206° C.)

Gas-liquid chromatography (glc): OV17 at 180° produced one peak.

Using the methodology described in Example IV and starting from 3-formyl-3-n-propyloxetane and 3-i-butyl-3-formyloxetane, 1-(3,3-dimethylbut-1-ynyl)-4-n-propyl-2,6,7-trioxabicyclo[2.2.2]octane-3-carbonitrile and 4-i-butyl-1-(3,3-dimethylbut-1-ynyl)-2,6,7-trioxabicyclo[2.2.2]octane-3-carbonitrile were prepared.

Using analogous methodology [E-1-(3,3-dimethylbut-1-enyl)-4-n-propyl-2,6,7-trioxabicyclo[2.2.2]octane-3-carbonitrile and trans-1-(2-t-butylcyclopropyl)- 4-n-propyl-2,6,7-trioxabicyclo[2.2.2]octane-3-carbonitrile were prepared from [E-4,4-dimethylpent-2-enoic acid and ethyl trans-2-t-butylcyclopropane carboxylate (E. L. Foreman and S. M. McElvain *J. Amer. Chem. Soc.*, 1940, 62, 1438 and I. A. D'yakonov et al Chem. Abs. 70:78062 m respectively).

Using analogous methodology 4-t-butyl-1-(3,3-dimethylbutyl) -2,6,7-trioxabicyclo[2.2.2 ]octane and 1-( 3,3 - dimethylbutyl) -4-n-propyl-2,6,7-trioxabicyclo[2.2.2]octane-3-carbonitrile were prepared from 4,4-dimethylpentanoic acid (G. M. Whitesides et al *J. Amer. Chem. Soc.* 1967, 89, 1135).

EXAMPLE XI 1-(Hex-5ynyl)-4-n-propyl-2-oxa-6,7-dithiabicyclo[2.2.2]octane (i) A stirred solution of 6-cyanohex-1-yne (4.0 g) (Synthesis: see example II, stage ii) in dry methanol (30 ml) and dry diethyl ether (30 ml) was saturated with hydrogen chloride gas and the temperature was maintained between −10° and 0°. The solution was diluted with dry diethyl ether (120 ml) and left at −20° for 24 hours. The white crystalline solid was filtered off and dried in vacuo to give methyl iminohept-6-ynoate hydrochloride.

(ii) Dry methanol (33 ml) was added to methyl iminohept-6-ynoate hydrochloride (38.4 g), under a current of dry nitrogen. Hexane (750 ml) was added and the mixture was stirred at 20° for 6 hours. The mixture was allowed to stand overnight and the supernatant hexane solution was removed by decantation and evaporated in vacuo to give trimethyl orthohept-6-ynoate, a colourless oil (25.0 g). (iii) Using methodology described in European Patent 216625, and starting from trimethyl orthohept-6-ynoate and 2-hydroxymethyl-2-n-propyl-propan-1,3-dithiol (synthesis also described in European Patent 216625), 1-(hex-5-ynyl)-4-n-propyl-2-oxa-6,7-dithiabicyclo[2.2.2]octane was prepared.

2-Hydroxymethyl-2-t-propylpropan-1,3-dithiol was also prepared as follows:

(i) 3-n-Propyloxetan-3-ylmethyl methanesulphonate was prepared from 3-hydroxymethyl-3-n-propyloxetane and methanesulphonyl chloride using methodology outlined in stage i) of Example II.

(ii) A solution of benzyl mercaptan (25.0 ml) in dry dimethylformamide (100 ml) was stirred at 0° C., under a current of nitrogen. Sodium hydride (6.0 g., 80% dispersion in oil) was added carefully and the mixture was stirred at 0° for 1 hour. 3-n-Propyloxetan-3-ylmethyl methanesulphonate (10.0 g.) was added and the mixture was stirred at 0° C. for 1 hour. The mixture was refluxed with stirring for 6 hours. The mixture was cooled and poured into water. The aqueous mixture was extracted with diethyl ether. The ethereal extracts were washed with water, dried over anhydrous magnesium sulphate and evaporated in vacuo. The residue was chromatographed on silica, eluting with 1:4; diethyl ether: hexane. 2,2-Di-(benzylthiomethyl)pentan-1-ol was obtained as a pale yellow oil (15.6 g.)

Mass spectrum (chemical ionisation):M+1 361

(iii)2,2-Di-(benzylthiomethyl)pentan-1-ol (8.0 g.) in dry diethyl ether (150 ml) was added to liquid ammonia (500 ml) which was stirred under nitrogen at −70°. Sodium (8.0 g.) was added in small pieces and the mixture was stirred at −70° for 3 hours. The mixture was allowed to warm to 20° and solid ammonium chloride (20 g.) was added. This was followed by careful addition of methanol (100 ml) to destroy excess sodium. Water (200 ml) was added and the aqueous mixture was extracted with diethyl ether. The ethereal extracts were dried over anhydrous magnesium sulphate and evaporated in vacuo. 2-Hydroxymethyl-2-n-propylpropan-1,3-dithiol was obtained as a colourless oil (4.6 g.).

In an analogous manner 4-n-butyl-1-(hex-5-ynyl)-2-oxa-6,7-dithiabicyclo[2.2.2]octane, 4-t-butyl-1-(hex-5-ynyl)-2-oxa-6,7-dithiabicyclo[2.2.2]octane, 4-i-butyl-1-(hex-5-ynyl)-2-oxa-6,7-dithiabicyclo[2.2.2]octane, 1-(hex-5-ynyl)-4-phenyl-2-oxa-6,7-dithiabicyclo[2.2.2]octane and 4-cyclopropylmethyl-1-(hex-5-ynyl)-2-oxa-6,7-dithiabicyclo[2.2.2]octane were prepared from trimethyl orthohept-6-ynoate and 2-n-butyl-2-hydroxymethylpropan-1,3-dithiol, 2-t-butyl-2-hydroxymethylpropan-1,3-dithiol, 2-i-butyl-2-hydroxymethylpropan-1,3-dithiol, 2-hydroxy-methyl-2-phenylpropan-1,3-dithiol and 2-cyclopropylmethyl-2-hydroxymethylpropan- 1,3-dithiol respectively.

EXAMPLE XII

1-Hex-5-ynyl-4-n-propyl-2,6,7-trithiabicyclo[2.2.2]octane

Method 1

Boron trifluoride etherate (0.20 ml) was added to a stirred solution of 2-mercaptomethyl-2-n-propylpropan-1,3-dithiol (0.30 g) (Synthesis described in Example XXXI) and trimethyl orthohept-6-ynoate (0.30 g) in dry dichloromethane (10 ml) at 20° under nitrogen. The mixture was stirred at 20° for 5 hours and triethylamine (1.0 ml) was added. Water was added and the aqueous mixture was extracted with diethyl ether. The ethereal extracts were dried over anhydrous magnesium sulphate and the solvent was removed in vacuo. The residue was chromatographed on alumina, eluting with 1:10 dichloromethane: hexane saturated with ammonia. The volatile impurity (methyl hept-6-ynoate) was removed in vacuo (130°, 10 mm Hg)

Recrystallisation of the residue from hexane gave 1-(hex-5-ynyl)-4-n-propyl- 2,6,7-trithiabicyclo[2.2.2]octane as a colourless solid (10 mg).

Method 2

A solution of trimethyl orthohept-6-ynoate (6.0 g.) in dry methanol (24 ml.) was stirred at 0° C., under nitrogen. 2-Mercaptomethyl-2-n-pro-pylpropan-1,3-dithiol (3.0 g) in dry methanol (10 ml) was added and this was followed by methanol, saturated with hydrogen chloride (1.0 ml). After 20 minutes stirring, at 0° C., dry triethylamine (3.0 ml) was added. Water (100 ml) was then added and the mixture was extracted with diethyl ether. The ethereal extracts were dried over anhydrous magnesium sulphate and evaporated in vacuo. The residue was chromatographed on alumina, eluting with 1:10; dichloromethane:hexane saturated with ammonia. The volatile components were removed in vacuo (kugelrohr at 130°, 0.5 mm Hg). The residue was crystallised from hexane.

1-(Hex-5-ynyl)-4-n-propyl-2,6,7-trithiabicyclo[2.2.2]octane was obtained as colourless crystals (0.90 g.).

Using analogous methodology (Method 2) 4-ethyl-1-(hex-5-ynyl)-2,6,7-trithiabicyclo[2.2.2]octane and 4-i-butyl-1-(hex-5-ynyl)-2,6,7-trithiabicyclo[2.2.2]octane were prepared from trimethylortho-hept-6-ynoate and 2-ethyl-2-mercaptomethylpropan-1,3-dithiol and 2-i-butyl-2-mercaptomethylpropan-1,3-dithiol respectively.

EXAMPLE XIII 4-n-Propyl-1-[2-(prop-2-ynylthio)ethyl]-2,6,7-trioxabicyclo[2.2.2]octane (i) A solution of 3-mercaptopropionic acid (15 ml) in dry dimethylformamide (250 ml) was stirred at 0°, under nitrogen. Sodium hydride (10.2 g; 80% dispersion in oil) was added carefully and the mixture was stirred at 40° for 1 hour. The mixture was cooled to 0° C. and propargyl bromide (60 g; 80% in toluene) was added dropwise. The mixture was stirred at 20° for 3 hours and then at 80° for 1 hour. The mixture was cooled and poured into water. The aqueous mixture was extracted with diethyl ether, and the extracts washed with water and dried over anhydrous magnesium sulphate. The solvent was removed in vacuo. The resulting oil (30 g) (mainly prop-2-ynyl 3-(prop-2-ynylthio)propionate) was added to a solution of sodium hydroxide (8.0 g) in water (100 ml) and methanol (100 ml) and the mixture was stirred at 20° for 24 hours. The mixture was extracted with diethyl ether and the aqueous solution was acidified with hydrochloric acid. The acidic mixture was extracted with diethyl ether and the ethereal extracts were dried over anhydrous magnesium sulphate. The solvent was removed in vacuo. 3-(Prop-2-ynylthio) propionic acid was obtained as a red oil (12.0 g) and was used without further purification.

(ii) 4-n-Propyl-1-[2-(prop-2-ynylthio)ethyl]-2,6,7-trioxabicyclo[2.2.2]octane was prepared from 3-(prop-2-ynylthio)propionic acid and 3-hydroxymethyl-3-n-propyloxetane using methodology described in Example I.

4-t-Butyl-1-[2-(prop-2-ynylthio)ethyl]-2,6,7-trioxabicyclo[2.2.2]octane was prepared from 3-(prop-2-ynylthio)propionic acid and 3-t-butyl-3- hydroxymethyloxetane using methodology described in Example I.

4-n-Propyl-1-[2-(prop-2-ynylthio)ethyl]-2,6,7-trioxabicyclo[2.2.2]octane-3-carbonitrile was prepared from 3-(prop-2-ynylthio)propionic acid and 3-formyl-3-n-propyloxetane using methodology described in Example IV.

EXAMPLE XIV 4-n-Propyl-1-[2-(prop-2-ynyloxy)ethyl]-2,6,7-trioxabicyclo[2.2.2]octane (i) 3-(Prop-2-ynyloxy)propionic acid was prepared from propargyl alcohol and ethyl 3-bromopropionate using methodology analogous to that describing the synthesis of 3-(but-3-yn-1-yloxy)propionic acid (Example XIX).

(ii) 4-n-Propyl-1-[2-(prop-2-ynyloxy)ethyl]-2,6,7-trioxabicyclo[2.2.2] octane was prepared from 3-(prop-2-ynyloxy)propionic acid and 3-hydroxymethyl-3-n-propyloxetane using methodology described in Example I.

4-t-Butyl-1-[2-(prop-2-ynyloxy)ethyl]-2,6,7-trioxabicyclo[2.2.2]octane was prepared from 3-(prop-2-ynyloxy)propionic acid and 3-t-butyl-3hydroxymethyloxetane using methodology described in Example I.

4-n-Propyl-1-[2-(prop-2-ynyloxy)ethyl]-2,6,7-trioxabicyclo[2.2.2]octane-3-carbonitrile was prepared from 3-(prop-2-ynyloxy)propionic acid and 3-formyl-3-n-propyloxetane using methodology described in Example IV.

EXAMPLE XV 1-(But-3-ynyloxymethyl)-4-n-propyl-2,6,7-trioxabicyclo[2.2.2]octane (i) 2-(But-3-ynyloxy)acetic acid was prepared from but-3-yn-1-ol and ethyl bromoacetate using methodology analogous to that describing the synthesis of 3-(but-3-ynyloxy)propionic acid (Example XIX).

(ii) 1-(But-3-ynyloxymethyl)-4-n-propyl-2,6,7-trioxabicyclo[2.2.2]octane was prepared from 2-(but-3-ynyloxy)acetic acid and 3-hydroxymethyl-3-n-propyl-oxetane using methodology described in Example I 4-t-Butyl-1-(but-3-ynyloxymethyl)-2,6,7-trioxabicyclo[2.2.2]octane was prepared from 2-(but-3-ynyloxy)acetic acid and 3-t-butyl-3-hydroxymethyloxetane using methodology described in Example I 1-(But-3-ynyloxymethyl)-4-n-propyl-2,6,7-trioxabicyclo[2.2.2]octane-3-carbonitrile was prepared from 2-(but-3-ynyloxy)acetic acid and 3-formyl-3-n-propyl-oxetane using methodology described in Example IV

EXAMPLE XVI 4-t-Butyl -1-(hept-6-ynyl)-2,6,7-trioxabicyclo[2.2.2]octane
(i) Sodium (1.2 g) was dissolved in dry ethanol (200 ml). Diethyl malonate (7.8 ml) was added and the mixture was stirred for 30 minutes and hex-5-ynyl methanesulphonate (9.0 g) was added. The mixture was stirred and refluxed for 1 hour. The mixture was cooled and the volume was reduced in vacuo. The mixture was poured into water and the aqueous mixture was extracted with diethyl ether. The ethereal extracts were washed with water and dried over anhydrous magnesium sulphate. The solvent was removed in vacuo. The crude ester was added to a solution of aqueous sodium hydroxide solution (100 ml of 15% solution) and methanol (50 ml) and the mixture was stirred at 20° for 24 hours. The mixture was extracted with diethyl ether. The aqueous alkaline phase was acidified with hydrochloric acid and the mixture was extracted with diethyl ether. The ethereal extracts were dried over anhydrous magnesium sulphate. The solvent was removed in vacuo. 2-(Hex-5-ynyl)malonic acid was obtained as a colourless solid (4.5 g) and was used without further purification.

(ii) A mixture of 2-(hex-5-ynyl)malonic acid (2.2 g) and cuprous oxide (60mg) in dry acetonitrile (40 ml) was stirred and refluxed, under nitrogen, for 6 hours. The solvent was removed in vacuo. 5% Aqueous hydrochloric acid was added and the aqueous mixture was extracted with diethyl ether. The ethereal extracts were dried over anhydrous magnesium sulphate and the solvent was removed in vacuo. Oct-7-ynoic acid was obtained as an oil (1.5 g) and was used without further purification.

(iii) 4-t-Butyl-1-(hept-6-ynyl)-2,6,7-trioxabicyclo[2.2.2]octane was prepared from oct-7-ynoic acid and 3-t-butyl-3-hydroxymethyloxetane using methodology described in Example I.

1-(Hept-6-ynyl)-4-n-propyl-2,6,7-trioxabicyclo[2.2.2]octane was prepared from oct-7-ynoic acid and 3-hydroxymethyl-3-n-propyloxetane using methodology described in Example I.

EXAMPLE XVII 1-(Hex-5-ynyl)-4-(prop-2-enyl)-2.6.7-trioxabicyclo[2.2.2]octane-3-carbonitrile (i) Pent-4-enal was prepared from pent-4-en-1-ol (supplied by Aldrich) as described in Example IV, stage (i).

(ii) 2-Hydroxymethyl-2-(prop-2-enyl)propan-1,3-diol was prepared from pent-4-enal as described in Example I, stage (i)

3-Formyl-3-(prop-2-enyl)oxetane was prepared from 2-hydroxymethyl-2-(prop- 2-enyl)propan-1,3-diol as described in Examples I and IV.

1-(Hex-5-ynyl)-4-(prop-2-enyl)-2,6,7-trioxabicyclo[2.2.2]octane-3-carbonitrile was prepared from hept-6-ynoic acid and 3-formyl-3-(prop-2-enyl)oxetane as described in Example IV.

In an analogous manner, starting from 2-(but-3-ynyloxy)acetic acid (Example XV) and 3-formyl-3-(prop-2-enyl)oxetane, 1-(but-3-ynyloxy-methyl)-4-(prop-2-enyl)-2,6,7-trioxabicyclo[2.2.2]octane-3-carbonitrile was prepared.

In an analogous manner, starting from hex-5-en-1-ol (supplied by Aldrich), 4-(but-3-enyl)-1-(hex-5-ynyl)-2,6,7-trioxabicyclo[2.2.2]octane-3-carbonitrile was prepared.

The triol obtained from 2-(but-3-enyl)-2-hydroxymethyl-propan-1,3-diol triacetate by transesterification using sodium methoxide in methanol contained impurities and was purified as follows:

A mixture of crude 2-(but-3-enyl)-2-hydroxymethylpropan-1,3-diol (4.5 g), acetone (30 ml) and p-toluenesulfonic acid (0.25 g) was refluxed in a Dean and Stark apparatus for 7 hours. The mixture was cooled and washed with aqueous sodium hydrogen carbonate solution. The organic solution was dried over anhydrous magnesium sulphate and the solvent was removed in vacuo. The residue was chromatographed on silica, eluting with 1:4 diethyl ether: hexane. 5-(But-3-enyl)-2,2-dimethyl-5-hydroxymethyl-1,3-dioxane was obtained as a colourless oil (1.0 g).

Mass Spectrum (Chemical Ionisation):M+1 201

5-(But-3-enyl)-2,2-dimethyl-5-hydroxymethyl-1,3-dioxane (0.80 g) and Amberlyst "15" (0.50 g) in methanol (100 ml) containing water (1.0 ml) was refluxed, with stirring, for 6 hours. The mixture was filtered and the filtrates were evaporated in vacuo 2-(But-3-enyl)-2-hydroxymethylpropan-1,3-diol was obtained as a colourless oil (0.6 g) which solidified on standing.

3-(But-3-enyl)-3-formyloxetane was prepared from 2(but-3-enyl)-2-hydroxymethylpropan-1,3-diol as described in Examples I and IV. 4-(But-3-enyl)-1-(hex-5-ynyl)-2,6,7-trioxabicyclo[2.2.2]octane-3-carbonitrile was prepared from hept-6-ynoic acid and 3-(but-3-enyl)-3-formyloxetane as described in Example IV.

EXAMPLE XVIII 4-t-Butyl-1-(4-methylhex-5-ynyl)-2,6,7-trioxabicyclo[2.2.2]octane (i) A mixture of diethyl 2-acetyl-2-methylhexane-1,6-dioate (16.0 g), (Chem. Ber. 1980, 113,451), hydrochloric acid (100 ml) and ethanol was refluxed for 4 hours. The mixture was cooled, diluted with water and basified with sodium hydrogen carbonate solution. The aqueous mixture was extracted with diethyl ether. The ethereal extracts were washed with water, dried over anhydrous magnesium sulphate and evaporated in vacuo.

Ethyl 5-methyl-6-oxoheptanoate was obtained as a colourless oil (7.3 g) and was used without further purification.

The aqueous alkaline extracts obtained above were acidified with hydrochloric acid and the aqueous mixture was extracted with diethyl ether. The ethereal extracts were dried over anhydrous magnesium sulphate and the solvent was removed in vacuo.

5-Methyl-6-oxoheptanoic acid was obtained as a yellow oil (8.5 g).

(ii) A mixture of phosphorous pentachloride (3.0 g), dry pyridine (4.0 ml) and benzene (30 ml) was stirred at 25°, under nitrogen. Ethyl 5-methyl-6-oxoheptanoate (1.0 g) in benzene (3.0 ml) was added and the mixture was refluxed with stirring for 3 hours. The mixture was cooled and poured into ice and water. The aqueous mixture was extracted with diethyl ether. The ethereal extracts were washed with N hydrochloric acid, sodium hydrogen carbonate solution and finally water. The ethereal extracts were dried over anhydrous magnesium sulphate and evaporated in vacuo. The resulting oil (800 mg) consisted of ethyl 6-chloro-5-methylhept-6-enoate ( 70%) and ethyl 6-chloro-5-methylhept-5-enoate (30%) and was used without further purification.

Mass Spectrum (Chemical Ionisation):

In combination with Gas-liquid chromatography. Two components were observed (ratio 2:1)

M+1 for both components 205 .

(iii) A mixture of lithium aluminium hydride (1.2 g) in dry diethyl ether (100 ml) was stirred at 0°, under nitrogen. The mixture of ethyl 6-chloro-5-methylhept-6-enoate and ethyl 6-chloro-5-methylhept-5-enoate (4.0 g) in dry diethyl ether (20 ml) was added and the mixture was stirred under nitrogen for 2 hours. Aqueous sodium hydroxide solution (10 ml, 10%) was added carefully. The supernatant ether solution was removed by decantation and the residue was washed with diethyl ether (2×50 ml). The combined ethereal extracts were dried over anhydrous magnesium sulphate and evaporated in vacuo. The resulting oil (3.5 g) consisted of 6-chloro-5-methylhept-5-en-1-ol (50%) and the E and Z isomers of 6-chloro-5-methylhept-5-en-1-ol (50%) and was used without further purification.

(iv) The mixture of 6-chloro-5-methylhept-6-en-1-ol and E and Z isomers of 6-chloro-5-methylhept-5-en-1-ol (2.8 g) was stirred in dry tetrahydrofuran (50 ml) at 0° under nitrogen n-Butyllithium (43 ml of 1.6M solution in hexane) was added and the mixture was stirred at 20°, for 4 hours. Ice was added and the aqueous mixture was extracted with diethyl ether. The ethereal extracts were washed with water and dried over anhydrous magnesium sulphate. The solvent was removed in vacuo and the resulting oil was chromatographed on silica, eluting with 2:5 diethyl ether:hexane.

5-Methylhept-6-yn-1-ol was obtained as a colourless oil (1.2 g)

Gas-liquid chromatography (glc): OV17 at 120° produced one peak.

Mass spectrum (Chemical Ionisation)

Gaseous ammonia as ionising gas M+18 144

(v) A solution of 5-methylhept-6-yn-1-ol (1.0$_g$) in dry dimethylformamide (9.0 ml) was stirred at 20° and pyridinium dichromate (10.5 g) was added carefully. The mixture was stirred at 20° for 24 hours. Diethyl ether (50 ml) was added and the supernatant liquid was removed by decantation. The residue was washed with further portions of diethyl ether (10×50 ml). The ethereal extracts were washed with 0.5N hydrochloric acid solution and then water. The ethereal extracts were dried over anhydrous magnesium sulphate and the solvent removed in vacuo.

5-Methylhept-6-ynoic acid was obtained as a light brown oil (0.80 g) and was used without further purification.

(vi) 4-t-Butyl-1-(4-methylhex-5-ynyl)-2,6,7-trioxabicyclo[2.2.2]octane was prepared from 5-methylhept-6-ynoic acid and 3-t-butyl-3-hydroxymethyl oxetane as described in Example I.

1-(4-Methylhex-5-ynyl)-4-n-propyl-2,6,7-trioxabicyclo[2.2.2]octane-3-carbonitrile was prepared from 5-methylhept-6-ynoic acid and 3-formyl-3-n-propyloxetane using methodology described in Example IV.

EXAMPLE XIX

1-[2-(But-3-ynyloxy)ethyl]-4-propyl-2,6,7-trioxabicyclo[2.2.2]octane (i) Sodium hydride (4.6 g of 60% dispersion in mineral oil) was added to a stirred solution of but-3-yn-1-ol (16.2 g, 0.23 mol, Lancaster) in dry toluene (200 ml). After stirring for 2 hours at 25° C. a solution of ethyl 3-bromopropionate (20.8 g, 0.115 mol, Lancaster) was added. The reaction mixture was stirred and refluxed for 7 hours. Ethyl 3-(but-3-ynyloxy)propionate (17.8 g) was obtained by quenching the cooled reaction mixture in water, extracting with ether, washing with brine, drying over anhydrous magnesium sulphate followed by evaporation.

(ii) Ethyl 3-(but-3-ynyloxy)propionate (17.4 g) was stirred overnight with a solution of sodium hydroxide (150 ml, 2M). After extracting with ether the aqueous layer was acidified with concentrated hydrochloric acid. The required acid was obtained by ether extraction. The organic phase was washed with brine and dried over magnesium sulphate. Evaporation gave 3-(but-3-ynyloxy)propionic acid (8.8 g) as a colourless oil.

1-[2-(But-3-ynyloxy)ethyl]-4-n-propyl-2,6,7-trioxabicyclo[2.2.2]octane was prepared from 3-(but-3-ynyloxy)propionic acid and 3-hydroxymethyl-3-t-propyloxetane using the methodology outlined in Example I.

Using the above methodology and starting from ethyl 2-bromopropionate (supplied by Lancaster Synthesis) and but-3-yn-1-ol (supplied by Lancaster Synthesis), 1-[1-(But-3-ynyloxy)ethyl]-4-n-propyl-2,6,7-trioxabicyclo[2.2.2]octane was prepared.

EXAMPLE XX 1-(7-Methoxyhept-5-ynyl)-4-n-propyl-2,6,7-trioxabicyclo[2.2.2]octane (i) A mixture of 7-chloro-1-methoxyhept-2-yne (8.0 g) (J. Martell and E. Toromanoff Chem abs. 76: 24712d) and sodium cyanide (5.0 g) in dimethylformamide (20 ml) and water (20 ml) was stirred at 80° for 7 hours. The mixture was cooled and diluted with water. The aqueous mixture was extracted with diethyl ether. The ethereal extracts were washed with water, dried over anhydrous magnesium sulphate and evaporated in vacuo.

7-Cyano-1-methoxyhept-2-yne was obtained as a yellow oil (6.0 g). Mass spectrum (Chemical Ionisation):M+1 152

(ii) A mixture of 7-cyano-1-methoxyhept-2-yne (6.0 g) and aqueous sodium hydroxide solution (100 ml, 2N) was refluxed, with stirring for 16 hours. The mixture was cooled and extracted with diethyl ether. The aqueous alkaline solution was acidified with hydrochloric acid and the aqueous mixture was extracted with diethyl ether. The ethereal extracts were dried over anhydrous magnesium sulphate and evaporated in vacuo.

8-Methoxyoct-6-ynoic acid was obtained as colourless oil (6.0 g).

1-(7-Methoxyhept-5-ynyl)-4-n-propyl-2,6,7-trioxabicyclo[2.2.2]octane was prepared from 8-methoxyoct-6-ynoic acid and 3-hydroxymethyl-3-n-propyloxetane using the methodology described in Example 1.

EXAMPLE XXI 4-t-Butyl-(7-methoxyhept-5-ynyl)-2,6,7-trioxabicyclo[2.2.2]octane (i) Methyl 5-bromopentanimidate hydrochloride (m.p. 89°) was prepared from 5-bromovaleronitrile using methodology described in stage (i) of Example XI.

(ii) Trimethyl 5-bromoorthopentanoate (colourless liquid, b.p. 108°–110°, 16 mm Hg) was prepared from methyl 5-bromopentanimidate hydrochloride as described in stage (ii) of Example XI.

(iii) 1-(4-Bromobutyl)-4-t-butyl-2,6,7-trioxabicyclo[2.2.2]octane (m.p. 111°–5°) was prepared from trimethyl 5-bromoorthopentanoate and 2-t-butyl-2-hydroxymethyl-propan-1,3-diol using the methodology described in Method 2 of Example VI.

Mass spectrum (Chemical Ionisation) M+1 307 309

(iv) Sodium (0.1 g) was added to a stirred solution of anhydrous liquid ammonia (70 ml) and dry diethyl ether (20 ml), under nitrogen, at −70°. After 10 minutes a crystal of ferric nitrate (15 mg) was added to the dark blue solution. The reaction mixture, which had turned grey was allowed to warm up to −30° and a further quantity of sodium (0.75 g), in small pieces, was added. The mixture was stirred for 30 minutes at −30° and methyl propargyl ether (2.2 g) was added. The mixture was stirred for a further hour at −30° and 1-(4-bromobutyl)-4-t-butyl-2,6,7-trioxabicyclo[2.2.2]octane (1.0 g) in dry diethyl ether (50 ml) was added. The mixture was stirred at −30° for 1 hour. Solid ammonium chloride (1.7 g) and then methanol (5 ml) were added and the mixture was allowed to warm to room temperature. Water (20 ml) was added and the aqueous mixture was extracted with diethyl ether. The ethereal extracts were dried over anhydrous magnesium sulphate and evaporated in vacuo. The residue was chromatographed on alumina, eluting with 1:9 dichloromethane:hexane, saturated with ammonia.

4-t-Butyl-(7-methoxyhept-5-ynyl)-2,6,7-trioxabicyclo[2.2.2]octane was obtained as a colourless solid (m.p. 47°–49°, recrystallised from hexane).

EXAMPLE XXII

But-3-ynyl-4-n-propyl-2,6,7-trioxabicyclo[2,2,2]octane-1-carboxylate (i) Oxalyl chloride (4.3 ml) was added to a stirred solution of but-3-yn-1-ol (3.5 g) in dry dichloromethane (75 ml), at 0°. The solution was stirred at 0° for 30 minutes and was then added, dropwise to a stirred solution of 3-hydroxymethyl-3-t-propyloxetane (6.4 g) and dry pyridine (30 ml) in dry dichloromethane (75 ml). The mixture was stirred at 20° for 24 hours. Water was added and the aqueous mixture was extracted with diethyl ether. The ethereal extracts were washed with 5% hydrochloric acid solution, saturated sodium hydrogen carbonate solution and finally water. The ethereal extracts were dried over anhydrous magnesium sulphate and evaporated in vacuo. The resulting oil was chromatographed on silica (pre-eluted with 1% triethylamine in hexane), and eluting with 1:1 diethyl ether:hexane. But-3-ynyl (3-n-propyloxetan-3-yl)methyl oxalate was obtained as a colourless oil (7.0 g).

(ii) But-3-ynyl 4-n-propyl-2,6,7-trioxabicyclo[2.2.2]octane-1-carboxylate was prepared from but-3-ynyl (3-n-propyloxetan-3-yl)methyl oxalate using the methodology described in Example I.

EXAMPLE XXIII

N-(Prop-2-ynyl)-4-n-propyl-2,6,7-trioxabicyclo[2.2.2]octane-1-carboxamide (i) Ethyl 4-n-propyl-2,6,7-trioxabicyclo[2.2.2]octane-1-carboxylate was prepared from 3-hydroxymethyl-3-t-propyloxetane and ethyl oxalyl chloride (supplied by Aldrich) using methodology described in Example 1. (colourless solid m.p. 70°)

Mass spectrum (Chemical Ionisation) M+1 231

(ii) A solution of ethyl 4-n-propyl-2,6,7-trioxabicyclo[2,2,2]octane-1-carboxylate (0.12 g) and 2-propynylamine (0.5 ml) and methanol (20 ml) was allowed to stand at 20° for 4 days. The solution was evaporated in vacuo. The residue was chromatographed on alumina, eluting with 2:3 dichloromethane: hexane, saturated with ammonia.

N-(Prop-2-ynyl)-4-n-propyl-2,6,7-trioxabicyclo[2.2.2]octane-1-carboxamide was obtained as a pale yellow solid (0.12 g).

EXAMPLE XXIV

Prop-2-ynyl 2-{4-n-propyl-2,6,7-trioxabicyclo[2.2,2]oct-1-yl}acetate (i) Ethyl 2-{4-n-propyl-2,6,7-trioxabicyclo[2.2.21]oct-1-yl)acetate was prepared from ethyl malonyl chloride and 3-hydroxymethyl-3-n-propyloxetane using methodology as described in Example 1.

(ii) A mixture of ethyl 2-{4-n-propyl-2,6,7-trioxabicyclo[2.2.2]oct-1-yl} acetate (0.48 g) and sodium hydroxide (0.35 g) in methanol (10 ml) and water (2.0 ml) was stirred at 20° for 3 hours. Solid carbon dioxide pellets (10 g) were added and the mixture was evaporated to dryness. The crude sodium 2-{4-n-propyl-2,6,7-trioxabicyclo[2.2.2]oct-1-yl}acetate was used without further purification.

(iii) A mixture of sodium 2-{4-n-propyl-2,6,7-trioxabicyclo[2.2.2]oct-1-yl}acetate (1.0 g) and propargyl bromide (1.8 ml of 80% solution in toluene, supplied by Aldrich) in dry dimethylformamide (30 ml) was stirred at 20° for 24 hours. Water was added and the aqueous mixture was extracted with diethyl ether. The ethereal extracts were washed with water and dried over anhydrous magnesium sulphate. The solvent was removed in vacuo and the residue was chromatographed on silica (pre-eluted with 1:3 dichloromethane:hexane containing 3% triethylamine) and eluting with 1:3 dichloromethane:hexane containing 3% triethylamine.

Prop-2-ynyl 2-{4-n-propyl-2,6,7-trioxabicyclo[2.2.2oct-1-yl}acetate was obtained as a colourless solid (0.45 g).

EXAMPLE XXV 1-(But-3-ynylthiomethyl)4-n-propyl-2,6,7-trioxabicyclo[2.2.2]octane (i) But-3-ynyl methanesulphonate was prepared from but-3-yn-1-ol using the method described in stage (i) of Example 1

(ii) 2-(But-3-ynylthio)acetic acid: Method A

Thioglycollic acid (6.0 g) was added to a stirred solution of sodium hydroxide (8.0 g) in ethanol (50 ml). But-3-ynyl methanesulphonate (7.4 g) was added and the mixture was stirred at 20° for 24 hours. The reaction mixture was poured into water and the aqueous mixture was extracted with diethyl ether. The aqueous alkaline extracts were acidified with hydrochloric acid and the mixture was extracted with diethyl ether. The ethereal extracts were dried over anhydrous magnesium sulphate and evaporated in vacuo. The resulting oil was stirred in dry dimethylformamide (100 ml) and anhydrous sodium carbonate (15 g) was added. Methyl iodide (7.0 ml) was added and the reaction mixture was stirred at 20° for 3 days. Water was added and the aqueous mixture was extracted with diethyl ether. The ethereal extracts were washed with water and dried over anhydrous magnesium sulphate. The solvent was removed in vacuo and the residue was chromatographed on silica, eluting with 1:4 diethylether: hexane. Methyl 2-(but-3-ynylthio)acetate was obtained as a colourless oil (1.2 g) (a small amount of methyl 2-(but-3-yn-1-ylthio)propionate was present). A mixture of methyl 2-(but-3-ynylthio)acetate (0.6 g) and sodium hydroxide solution (20 ml, 2N, 1:1 methanol:water) was stirred for 24 hours at 20°. Water was added and the aqueous mixture was extracted with diethyl ether. The aqueous alkaline extracts were acidified with hydrochloric acid and the mixture was extracted with diethyl ether. The ethereal extracts were dried over anhydrous magnesium sulphate and the solvent was removed in vacuo. 2-(But-3-ynylthio)acetic acid was obtained as a colourless oil (0.5 g). (A small amount of 2-(but-3-ynylthio)propionic acid was present.

2-(But-3-ynylthio)acetic acid:- Method B 2-(But-3-ynylthio)acetic acid was prepared from thioglycollic acid and but-3-ynyl methanesulphonate using the methodology described in stage (i) of Example XIII.

(iii) 1-(But-3-ynylthiomethyl)-4-n-propyl-2,6,7-trioxabicyclo[2.2.2]octane was prepared from 2-(but-3-ynylthio)acetic acid and 3-hydroxymethyl-3-n-propyl-oxetane using the methodology described in Example I.

4-t-Butyl-1-(but-3-ynylthiomethyl)-2,6,7-trioxabicyclo [2.2.2]octane was prepared from 2-(but-3-ynylthio)acetic acid and 3-t-butyl- 3-hydroxymethyloxetane using the methodology described in Example I. A small amount of 4-butyl-1-[1-(but-3-yn-1-ylthio)ethyl]-2,6,7-trioxabicyclo[ 2.2.2] octane was also present.

EXAMPLE XXVI

N-(Prop-2-ynyl)-2-(4-n-propyl-2,6,7-trioxabicyclo[2.2.2] oct-1yl)acetamide

To a stirred solution of ethyl 2-(4-n-propyl-2,6,7-trioxabicyclo[2.2.2]-oct- 1-yl)acetate (300mg) (Example XXIV) in methanol (5 ml) was added 2-propynylamine (2.0 ml), followed by sodium cyanide (20mg). The mixture was stirred at 70°–80° for 12 hours. Water (10 ml) was added and the mixture extracted with ethyl acetate. The ethyl acetate extracts were dried over anhydrous magnesium sulphate and evaporated in vacuo. The residue was purified by chromatography on silica using gradient elution with ethyl acetate: hexane mixtures containing triethylamine (1%).

N-(Prop-2-ynyl)-2-(4-n-propyl-2,6,7-trioxabicyclo[2.2.2] oct-1-yl)acetamide was obtained as a yellowish oil (122 mg).

Gas liquid chromatography (g.l.c.): OV17 at 245° produced one peak. Example XXVII
1-(1-Methylhex -5-ynyl)-4-propyl -2,6,7-trioxabicyclo [2.2.2]octane i) Using exactly the same method as described in Example II stage (i), pent-4-ynyl methanesulphonate (37.8 g) was prepared from methanesulphonyl chloride (22 ml), triethylamine (44 ml) and pent-4-yn-1-ol (Lancaster synthesis, 20 g).

ii) A solution of diethyl methylmalonate (Aldrich Chemical Company, 35.6 ml) in dry tetrahydrofuran (200 ml) was added, dropwise, to a stirred suspension of sodium hydride (60% dispersion in mineral oil, 9.1 g) in tetrahydrofuran (50 ml) under nitrogen. After the addition was complete, the mixture was heated to gentle reflux for 1 hour and then allowed to cool before a solution of pent-4-ynyl methanesulphonate (35.2 g) in tetrahydrofuran (50 ml) was added. The resulting mixture was heated to gentle reflux for a further 2 hours. The bulk of the solvent was then removed in vacuo and the residue was partitioned between diethyl ether and water. The organic phase was separated and washed with water and brine before drying over anhydrous magnesium sulphate and evaporation under reduced pressure. Distillation gave diethyl 2-methyl-2-(pent-4-ynyl)malonate (45.8 g) as a colourless oil (b.p. 92°–97°, 0.5 mm Hg)

Gas liquid chromatography (g.l.c): OV-17 programmed from 120° to 210° produced one peak.

iii) A mixture of diethyl 2-methyl-2-(pent-4-ynyl)malonate (11 g) and potassium hydroxide (15 g) in 95% ethanol (150 ml) was heated to reflux for 4 hours and then stood at room temperature for 15 hours. The bulk of the solvent was removed in vacuo and the residue was taken up in water. The resulting aqueous phase was washed with dichloromethane before acidification to pH 1 with concentrated hydrochloric acid and further extraction with fresh dichloromethane. These organic extracts were washed with brine before drying over anhydrous magnesium sulphate and evaporation in vacuo. 2-Methyl-2-(pent-4-ynyl)malonic acid was obtained as a pale yellow solid (6.7 g).

iv) A mixture of 2-methyl-2-(pent-4-ynyl)malonic acid (5.7 g) and cuprous oxide (0.22 g) in acetonitrile (150 ml) was heated to reflux, under a nitrogen atmosphere, for 4.25 hours. The solvent was removed under reduced pressure and water (50 ml) was added to the residue followed by sufficient concentrated hydrochloric acid to hydrolyse the copper salts. The resulting aqueous phase was extracted with diethyl ether and the organic extracts were washed with water and brine before drying over anhydrous magnesium sulphate and evaporation in vacuo. 2-Methylhept-6-ynoic acid (3.6 g) was obtained as a colourless oil after distillation (b.p. 150°–165°, 0.5 mm Hg).

v) Using the methodology described in stages (v) and (vi) of Example 1, 1-(1-methylhex-5-ynyl)-4-propyl-2,6,7-trioxabicyclo[2.2.2]octane was prepared from 2-methylhept-6-ynoic acid and 3-hydroxymethyl-3-n-propyl oxetane.

Gas-liquid chromatography(g.l.c.): OV-17 at 200° produced one peak.

In an analogous manner the following compound was also prepared: 4-t-Butyl-1-(1-methylhex-5-ynyl)-2,6,7-trioxabicyclo[2.2.2]octane.

Using methodology outlined in Example IV 1-(1-methylhex-5-ynyl)-4-n-propyl- 2,6,7-trioxabicyclo[2.2.2]octane-3-carbonitrile was prepared.

EXAMPLE XXVIII

Methyl 7-(4-n-propyl-2,6,7-trioxabicyclo[2.2.2]oct-1-yl)hept-2-ynoate i) n-Butyllithium (5.2 ml, 1.6M solution in hexane) was added to a solution of hept-6-ynoic acid (0.5 g) in dry tetrahydrofuran (20 ml) stirred at −70° under nitrogen. The resulting mixture was maintained at −70° for 0.25 hour when methyl chloroformate (0.32 ml) was added neat. The solution was stirred at −70° for a further 0.5 hour and then allowed to warm to room temperature over 0.5 hour. After this time, water (5 ml) was added and the bulk of the solvent was removed under reduced pressure. The residue was diluted with water and extracted with diethyl ether. The aqueous phase was separated, acidified to pH 1 with concentrated hydrochloric acid and then re-extracted with dichloromethane. The combined dichloromethane extracts were washed with brine before drying over anhydrous magnesium sulphate and evaporation in vacuo. The residue was purified by distillation (bulb-to-bulb, 0.5 mm Hg). At oven temperature 220° 1-methyl hydrogen 1,8-oct-2-yndioate distilled as a brown oil (183 mg).

Mass spectrum (Probe) (Chemical Ionisation) M+1 185 ii) Using the methodology described in stages (v) and (vi) of Example 1, methyl 7-(4-propyl-2,6,7-trioxabicyclo[2.2.2] oct-1-yl)hept-2-ynoate was prepared from 1-methyl hydrogen 1,8-oct-2-yndioate and 3-hydroxy-methyl-3-n-propyloxetane.

EXAMPLE XXIX 1-(Hex-5-ynyl)-3-methyl-4-n-propyl-2-oxa-6,7-dithiabicyclo[2.2.2]octane i) A solution of 2,2-di-(benzylthiomethyl)pentan-1-ol (1.0 g Example XI) in dry dichloromethane (10 ml) was added to a stirred suspension of pyridinium chlorochromate (1.5 g) and anhydrous sodium acetate (0.11 g) in dry dichloromethane (25 ml) at 0° C., under a current of nitrogen. The reaction mixture was allowed to warm to 20° C. and then stirred for 2 hours. Dry diethyl ether was added and the mixture stirred for 30 minutes. The ethereal extracts were decanted off and the residue was washed with further portions of diethyl ether. The combined ethereal extracts were dried over anhydrous magnesium sulphate and the solvent was removed in vacuo. The residue was purified by chromatography on a mixture of silica and charcoal, eluting with diethyl ether. 2,2-Di(benzylthiomethyl)pentanal was obtained as a pale yellow oil (0.27 g).

Mass spectrum (Chemical Ionisation) M+1 359 ii) A solution of 2,2-di-(benzylthiomethyl)pentanal (3.54 g) in dry diethyl ether was added dropwise to a stirred solution of methyl magnesium iodide [prepared from methyl iodide (1.2 ml) and magnesium (0.48 g)] in dry diethyl ether (60 ml). The reaction mixture was refluxed for 2 hours and then cooled. Saturated aqueous ammonium chloride solution was added. The mixture was stirred for 30 minutes and extracted with diethyl ether. The ethereal extracts were dried over anhydrous magnesium sulphate and the solvent was removed in vacuo. 3,3-Di-(benzylthiomethyl)hexan-2-ol was obtained as a yellow oil (1.7 g)

Mass Spectrum (Chemical Ionisation) M+1 375

1-(Hex-5-ynyl)-3-methyl-4-n-propyl-2-oxa-6,7-dithiabicyclo[2.2.2]octane was prepared from 3,3-di-(benzylthiomethyl)hexan-2-ol using methodology described in Example XI.

EXAMPLE XXX 1-(2-Methylhex-5-ynyl)-4-n-propyl-2,6,7-trioxabicyclo[2.2.2]octane-3-carbonitrile i) 1,4-Dimethylcyclohex-1-ene (12 g) (ref. Bellstein 5, 74) was dissolved in dry dichloromethane (120 ml) and the solution stirred at −70°. A current of ozone was passed through the solution for 3 hours. The solution was allowed to warm slightly and poured into a solution of hydrogen peroxide in water (600 ml of 3% solution). The dichloromethane was removed in vacuo and the mixture was stirred vigorously at 20° for 48 hours. The mixture was basified with saturated sodium hydrogen carbonate solution and the aqueous mixture was extracted with diethyl ether. The aqueous solution was acidified with 10% hydrochloric acid solution and the mixture was extracted with diethyl ether. After drying over anhydrous magnesium sulphate both ethereal extracts were evaporated in vacuo. Both residues contained organic acid and aldehyde. The combined residues (3.5 g) were stirred in dry dimethylformamide (30 ml) and pyridinium dichromate (17.4 g) was added. The mixture was stirred at 20° for 24 hours and then diluted with diethyl ether (50 ml). The ethereal extracts were decanted off and the black residue was washed repeatedly with more diethyl ether. The combined ethereal extracts were washed with dilute hydrochloric acid solution, water, and dried over anhydrous magnesium sulphate. The solvent was removed in vacuo and 3-methyl-6-oxoheptanoic acid was obtained as a yellow oil (2.45 g).

Mass spectrum (Chemical Ionisation) M+1 159 ii) 3-Methyl-6-oxoheptanoic acid (2.45 g) was stirred in dry dimethylformamide (60 ml) at 20° C. and anhydrous sodium carbonate (1.64 g) was added. Ethyl iodide (5.4 ml) was added dropwise and the mixture was refluxed with stirring for 2 hours. The mixture was cooled, poured into water and the aqueous mixture was extracted with diethyl ether. The ethereal extracts were washed with saturated aqueous sodium thiosulphate solution, water, and dried over anhydrous magnesium sulphate. The solvent was removed in vacuo and the residue was purified by chromatography on silica, eluting with 1:4 diethyl ether: hexane. Ethyl 3-methyl-6-oxoheptanoate was obtained as an orange oil (2.0 g)

Mass spectrum (Chemical Ionisation) M+1 187 iii) Using methodology described in Example XVIII, 3-methylhept-6-ynoic acid was prepared from ethyl 3-methyl-6-oxoheptanoate.

(iv) 1-(2-Methylhex-5-ynyl)-4-n-propyl-2,6,7-trioxabicyclo[2.2.2]octane 3 -carbonitrile was prepared from 3-methylhept-6-ynoic acid using methodology described in Example IV.

Starting from 3-methylhept-6-ynoic acid and 3-formyl-3-(prop-2-enyl) oxetane (see Example XVII) and using methodology described in Example IV, 1-(2-methylhex-5-ynyl)-4-(prop-2-enyl)-2,6,7.trioxabicyclo[2.2.2]octane-3-carbonitrile was prepared.

EXAMPLE XXXI 1-(But-3-ynyloxymethyl)-4-n-propyl-2,6,7-trithiabicyclo[2.2.2]octane i) Methanesulphonyl chloride (74.0 g) was added dropwise over 30 minutes to a solution of 2-hydroxymethyl-2-n-propylpropan-1,3-diol (28.0 g) in dry pyridine (200 ml) under nitrogen at 0° C. The mixture was allowed to warm to room temperature. After stirring for 18 hours the mixture was poured into water (200 ml) and extracted with chloroform (2×200 ml). The chloroform extracts were washed with water (2×100 ml), dried over anhydrous magnesium sulphate and evaporated in vacuo to give a brown solid. This was stirred in dry diethyl ether (200 ml) to give 2-hydroxymethyl-2-n-propylpropan-1,3-diol trimethanesulphonate as a white solid. (70.0 g)(m.pt.103.6°).

ii) Sodium trithiocarbonate (18.0 g) [see J.Org.Chem. 1968,33, 1275] in water (25 ml) was added to a solution of 2-hydroxymethyl-2-n-propyl-propan- 1,3-diol trimethanesulphonate (12.0 g) in dimethylformamide (100 ml). The mixture was heated to reflux (130° C.) for 4 hours then allowed to cool to room temperature. After a further 18 hours stirring, dilute sulphuric acid solution (50 ml) was added slowly over 30 minutes. The mixture was extracted with chloroform. The extracts were dried over anhydrous magnesium sulphate and evaporated in vacuo to give a brown liquid. Hexane (200 ml) was added and the mixture washed with water (3×50 ml). Drying over anhydrous magnesium sulphate and evaporation gave an amber oil (6.8 g). The crude oil (6.4 g) in diethyl ether (10 ml) was added dropwise to a suspension of lithium aluminium hydride (3.0 g) in dry diethyl ether (100 ml) at a rate sufficient to maintain reflux. The mixture was stirred for a further hour after addition was complete, then water (3 ml) this was added carefully. Dilute sulphuric acid (3 ml) was added and was followed by water (3 ml). The mixture was filtered, the solid washed with diethyl ether (50 ml) and the combined filtrates dried over anhydrous magnesium sulphate and evaporated in vacuo to give 2-mercaptomethyl-2-n-propylpropan-1,3-dithiol as a pale yellow oil (5.3 g).

iii) Hydrogen chloride gas was bubbled through a suspension of paraformaldehyde (4.3 g) in but-3-yn-1-ol (10.0 g) (Aldrich) and dry dichloromethane (30 ml) at −20° C. for 30 minutes. The mixture was allowed to warm to room temperature then stirred for a further 18 hours. Cold water (30 ml) was added and the organic layer separated, dried over anhydrous calcium chloride and evaporated to give but-3-ynyl chloromethyl ether as an amber liquid (14.2 g).

iv) 2-Mercaptomethyl-2-n-propylpropan-1,3-dithiol (2.3 g) and triethyl orthoformate (1.74 g) were heated together in dry toluene (5 ml) containing p-toluenesulphonic acid (5 mg) and the ethanol produced distilled off. After cooling, toluene (15 ml) was added and the mixture washed with water (2×10 ml). Drying over anhydrous magnesium sulphate and evaporation in vacuo gave a pale yellow oil. This was extracted with diethyl ether (50 ml) and the extracts evaporated in vacuo to give a white solid. Purification by chromatography on alumina, eluting with 1:10 dichloromethane:hexane saturated with ammonia gave 4-n-propyl-2,6,7-trithiabicyclo[2.2.2]octane as a white solid (0.33 g, m.pt.139°). Mass spectrum (Chemical Ionisation) M+1 207.

v) n-Butyllithium (0.3 ml,1.6M solution in hexane) was added to a solution of 4-n-propyl-2,6,7-trithiabicyclo[2.2.2]octane (0.1 g) in dry tetrahydrofuran (5 ml) at −70°, under nitrogen. The solution was stirred for 30 minutes and but-3-ynyl chloromethyl ether (0.058 g) in dry tetrahydrofuran (2.0 ml) was added and the reaction mixture was allowed to warm to 20°. Water (10 ml) was added and the mixture was extracted with diethyl ether. The ethereal extracts were dried over anhydrous magnesium sulphate and the solvent was removed in vacuo. The residue was purified by chromatography on alumina, eluting with 1:10 dichloromethane:hexane saturated with ammonia. 1-(But-3-ynyloxy-methyl)- 4-n-propyl-2,6,7-trithiabicyclo[2.2.2]octane was obtained as a waxy solid (0.032 g).

EXAMPLE XXXIII

1-[(E/Z)-Hex-3-en-5-ynyl]-4-propyl-2,6,7-trioxabicyclo[2.2.2]octane-3-carbonitrile i) ((E/Z)-5-Bromopent-4-enoic acid was prepared from diethyl malonate and an 1,3-dibromopropene (mixture of isomers, ALDRICH Chemical Company) using methodology described in Example XVI, stages (i) and (ii).

ii) Using the procedure described in stages (ii) and (iii) of Example IV, 1-[(E/Z)-4-bromobut-3-enyl]-4-propyl-2,6,7-trioxabicyclo[2.2.2]octane-3-carbonitrile (an oil) was prepared form ((E/Z)-5-bromopent-4-enoic acid and 3-formyl-3-n-propyloxetane.

Gas liquid chromatography (glc):OV-17 at 230° produced one peak. Mass spectrum (Chemical Ionisation)M+1 316, 318 iii) A mixture of 1-[(E/Z)-4-bromobut-3-enyl]-4-propyl-2,6,7-trioxabicyclo[2.2.2]octane-3-carbonitrile (500mg), trimethylsilylacetylene( 0.45 ml), bis-triphenylphosphinepalladium dichloride (30 mg) and cuprous iodide (5mg) in dry diethylamine (10 ml) was stirred at room temperature under a nitrogen atmosphere for 4 hours. The solvent was then removed in vacuo. The residue was taken up in diethyl ether and washed with water and brine before drying over anhydrous magnesium sulphate and evaporation under reduced pressure. The residue was purified by column chromatography on alumina eluting with hexane containing 15% dichloromethane saturated with ammonia. 4-Propyl-1-[(E/Z)-6-(trimethylsilyl)hex-3-en-5-ynyl]-2,6,7-trioxabicyclo[2.2.2]octane-3-carbonitrile was obtained as a pale yellow oil (365mg).

Gas-liquid chromatography (glc):OV-17 at 250° produced two peaks (E/Z isomers).

iv) Tetrabutylammonium fluoride (1.1 ml of a 1M solution in tetrahydrofuran) was added to a stirred solution of 4-propyl-1-[(E/Z)- 6-(trimethylsilyl)hex-3-en-5-ynyl]-2,6,7-trioxabicyclo[2.2.2]octane-3-carbonitrile (293mg) in tetrahydrofuran (5 ml). The resulting mixture was stirred at room temperature for 1 hour when the solvent was removed under reduced pressure. The residue was partitioned between diethyl ether and water. The organic phase was separated, washed with water and brine, dried over anhydrous magnesium sulphate and then evaporated in vacuo. The residue was purified by column chromatrography on alumina eluting with hexane containing 15% dichloromethane saturated with ammonia. 1-[(E/Z)-Hex-3-en-5-ynyl]-4-propyl-2,6,7-trioxabicyclo[2.2.2]octane-3-carbonitrile was obtained as a colourless oil (143mg).

Gas-liquid chromatography (glc):OV-17 at 250° produced one peak.

In an analogous manner the following compounds were prepared from 1-[(E/Z)-4-bromobut-3-enyl]-4-propyl.2,6,7.trioxabicyclo[2.2.2]octane- 3-carbonitrile and the requisite terminal acetylene (given in parentheses):

1-[(E/Z)-7-Methoxyhept-3-en-5-ynyl]-4-propyl-2,6,7-trioxabicyclo[ 2.2.2]octane-3-carbonitrile. (Methyl propargyl ether). 1-[(E/Z)-7-Hydroxyhept-3-en-5-ynyl]-4-propyl-2,6, 7-trioxabicyclo-[2.2.2]octane-3-carbonitrile. (Propargyl alcohol).

EXAMPLE XXXIII 4-t-Butyl-1-[(E)-hex-1-en-5-ynyl]-2,6,7-trioxabicyclo[2.2.2]octane-3-carbonitrile i) Using the method described in Example IV, stage (i), pent-4-yn-1-ol (Aldrich Chemical Company) was converted to pent-4-ynyl. The crude product was purified by bulb-to-bulb distillation (oven temperature <65°, 15 mm Hg).

Gas-liquid chromatography (glc):OV-17 at 80° produced one peak.

ii) A mixture of pent-4-ynyl(1.2 g) and (carbethoxymethylene)triphenylphosphorane (5.1 g) in dichloromethane (20 ml) was stirred at room temperature for 2.5 hours. The solution was evaporated under reduced pressure and the residue was extracted with hexane. Insoluble material was removed by filtration before the solvent was evaporated to leave a yellow oil. Ethyl (E)-hept-2-en-6-ynoate was obtained as a colourless oil (1.8 g) after bulb-to-bulb distillation (oven temperature 155°, 15mm Hg).

Gas-liquid chromatography (glc):OV-17 at 120° produced two peaks (95:5).

iii) A solution of ethyl (E)-hept-2-en-6-ynoate (1.8 g) in 50% aqueous methanol containing 5% sodium hydroxide was stirred at ambient temperature overnight. The methanol was removed under reduced pressure and the resulting aqueous phase was extracted with dichloromethane. The aqueous phase was adjusted to pH 1 with concentrated hydrochloric acid and re-extracted with dichloromethane. These organic extracts were washed with brine, dried over anhydrous magnesium sulphate and then evaporated in vacuo to leave (E)-hept-2-en-6-ynoic acid as a white solid (1.3 g).

iv) Using the method described in Example IV, stages (ii) and (iii), 4-t-butyl-1-[(E)-hex-1-en-5-ynyl]-2,6,7-trioxabicyclo[2.2.2]octane-3-carbonitrile was prepared from 3-t-butyl-3-formyloxetane and (E)-hept-2-en-6-ynoic acid.

Gas-liquid chromatography (glc):OV-17 at 220° produced two peaks (95:5).

EXAMPLE XXXIV 4-n-Propyl-2,6,7-trioxabicyclo[2.2.2]octane-1-carboxaldehyde oxime prop-2-ynyl ether i) A solution of ethyl 4-propyl-2,6,7-trioxabicyclo[2.2.2]octane-1-carboxylate (5.0 g) (Example XXIII) in anhydrous tetrahydrofuran (10 ml) was added dropwise to a stirred suspension of lithium aluminium hydride (1.86 g) in dry diethyl ether (100 ml) at 0° C., under nitrogen. Stirring was maintained at 0° C. for 1.5 hours then at room temperature for 2.5 hours. An aqueous solution of sodium hydroxide (25 ml of 10% solution) was added dropwise with cooling. The aqueous mixture was extracted with diethyl ether. The ethereal extracts were washed with water, brine and dried over anhydrous magnesium sulphate and then evaporated in vacuo.

The residue, 1-hydroxymethyl-4-propyl-2,6,7-trioxabicyclo[2.2.2]octane, was obtained as a white crystalline solid (3.4 g, m.pt. 100°–101° C.). Mass spectrum (Chemical Ionisation) M+1 189 ii) 4-Propyl-2,6,7-trioxabicyclo[2.2.2]octane-1-carboxaldehyde was prepared from 1-hydroxymethyl-4-propyl-2,6,7-trioxabicyclo[2.2.2]octane by the method described in Example IV, stage (i).

4-Propyl-2,6,7-trioxabicyclo[2.2.2]octane 1-carboxaldehyde, was obtained as a white solid (1.7 g; m.pt. 117°–118° C.). Mass spectrum (Chemical Ionisation). M+1 187 iii) A solution of 4-propyl-2,6,7-trioxabicyclo[2.2.2]octane-1-carboxaldehyde (1.0 g) in 1,2-dimethoxyethane (15 ml) was added to a stirred mixture of hydroxylamine hydrochloride (1.51 g) and sodium carbonate (2.29 g) in water (10 ml), at 20°. Stirring was maintained for 12 hours.

The mixture was diluted with diethyl ether and the organic phase was washed with water and brine, and dried over anhydrous magnesium sulphate, then evaporated in vacuo. The residue, 4-propyl- 2,6,7-trioxabicyclo[2.2.2]octane-1-carboxaldehyde oxime, was obtained as a white gummy solid (0.8 g).

Gas-liquid chromatography (glc): OV-17 at 210° C. showed a single peak. Mass spectrum (Chemical Ionisation). M+1 202 iv) To a stirred solution of 4-propyl-2,6,7-trioxabicyclo[2.2.2]octane- 1-carboxaldehyde oxime (0.52 g) in dry methanol (10 ml) was added propargyl bromide (0.44 ml of an 80% solution in toluene), followed by sodium methoxide (0.141 g). The mixture was stirred at 20° C. for 12 hours. The mixture was poured into water and the aqueous mixture was extracted with diethyl ether. The ethereal extracts were washed with water, brine and dried over anhydrous magnesium sulphate and then evaporated in vacuo.

The residue, a yellow oil, was purified by chromatography on silica (pre-treated with hexane containing 1% triethylamine) eluting with 4:1 ethyl acetate:hexane containing 1% triethylamine.

4-Propyl-2,6,7-trioxabicyclo[2.2.2]octane-1-carboxaldehyde oxime prop-2-ynyl ether, was obtained as a white crystalline solid (0.085 g, m.pt. 73°–74° C.).

EXAMPLE XXXV 2-(4-n-Propyl-2,6,7-trioxabicyclo[2.2.2]oct-1-yl)ethyl but-2-ynoate i) A solution of ethyl 2-(4-propyl-2,6,7-trioxabicyclo[2.2.2]oct-1-yl) acetate (5.0 g) (Example XXIV) in dry tetrahydrofuran (10 ml) was added dropwise to a stirred suspension of lithium aluminium hydride (1.8 g) in dry diethyl ether (100 ml), at 0° C. under a nitrogen atmosphere. Stirring was maintained at 0° C. for 1.5 hours. An aqueous solution of sodium hydroxide (25 ml of 10% solution) was added dropwise with cooling. The mixture was extracted with diethyl ether and the ethereal extracts were washed with water, brine and dried over anhydrous magnesium sulphate and then evaporated in vacuo. The residue, 1-(2-hydroxyethyl)-4-propyl-2,6,7-trioxabicyclo[2.2.2]octane was obtained as a colourless oil (3.5 g) which crystallised on standing to give a low melting waxy solid.

Gas-liquid chromatography (glc):OV-17 at 210° C. produced a single peak.

ii) To a stirred solution of 1-(2-hydroxyethyl)-4-propyl-2,6,7-trioxabicyclo[2.2.2]octane (0.5 g) in dry dichloromethane (20 ml) at 0° C. was added 4-dimethylaminopyridine (55mg), followed by tetrolic acid (210 mg). The mixture was stirred for 5 minutes at 0° C., then dicyclohexylcarbodiimide (520 mg) was added in portions (100 mg) over 2 hours. Stirring was continued at 20° C. for 12 hours. Water was added and the aqueous mixture was extracted with dichloromethane. The organic extracts were washed with 10% sodium hydrogen carbonate solution, water and brine before drying over anhydrous magnesium sulphate, and evaporation in vacuo. The residue was obtained as a yellow gum and was purified by chromatography on silica, pro-treated with hexane containing 1% triethylamine, eluting with 2:3 ethyl acetate:hexane containing 1% triethylamine.

2-(4-Propyl-2,6,7-trioxabicyclo[2.2.2]oct-1-yl)ethyl but-2-ynoate was obtained as a white crystalline solid (0.266 mg, m.pt. 80°–81° C.).

XXXVI

1 -(Hex-5-ynyl)-4-n-propyl-2,6-dioxabicyclo[2.2.2]octane (i) A solution of trimethylsilylacetylene (12.0 g., Aldrich) in dry tetrahydrofuran (100 ml.) was stirred at 0°, under a current of nitrogen and n-butyllithium (76.5 ml. of 1.6M solution in hexane) was added dropwise. The solution was stirred for 30 minutes and a solution of 1-chloro-3-iodopropane (25.0 g.) in dry tetrahydrofuran (75 ml.) was added. The reaction mixture was allowed to warm to 20° and stirred for 18 hours. The mixture was poured into water and the aqueous mixture was extracted with diethyl ether. The ethereal extracts were washed with water and dried over anhydrous magnesium sulphate. The solvent was removed in vacuo and the residue distilled. 5-Chloro-1-trimethylsilylpent-1-yne was obtained as a colourless oil (12.7 g., b.p. 67°–72°, 15 mm. Hg.).

ii) A mixture of 5-chloro-1-trimethylsilylpent-1-yne (13.5 g) and sodium iodide (29 g) in butanone (100 ml) was heated at reflux for 10 hours. After this time the solvent was removed in vacuo and the residue partitioned between diethyl ether and water. The organic phase was separated, washed with water and brine before drying over anhydrous magnesium sulphate. The solvent was removed under reduced pressure to leave 5-iodo-1-trimethylsilylpent-1-yne as a colourless oil (19.3 g).

(iii) n-Butyllithium (19.0 ml., 1.6M solution in hexane) was added dropwise to a stirred solution of acetone N,N-dimethylhydrazone (2.6 g.) (ref. R. H. Wiley et al *J. Org. Chem.* 1957, 22, 204) in dry tetrahydrofuran (40 ml.) at –70°, under a current of nitrogen. The resulting solution was stirred for 30 minutes and a solution of 5-iodo-1-trimethylsilylpent-1-yne (8.1 g.) in dry tetrahydrofuran (30 ml.) was added dropwise and the reaction mixture was stirred at –70° for 1 hour, allowed to warm to 0° and stirred for 2 hours. The reaction mixture was cooled to –70° and a second portion of n-butyllithium (19 ml. 1.6M solution in hexane) was added dropwise. The mixture was stirred at –70° for 15 minutes, allowed to warm to 0° and stirred for 30 minutes. A solution of 5-iodomethyl-2,2-dimethyl-5-n-propyl-1,3-dioxane (9.0 g. European Patent 216625) in dry tetrahydrofuran (30 ml.) was added. The mixture was stirred at 0° for 30 minutes and 48 hours at 20°. The solvent was removed in vacuo and the residue was poured into water. The aqueous mixture was extracted with diethyl ether and the ethereal extracts were washed with water, dried over anhydrous magnesium sulphate and evaporated in vacuo. Chromatography of the residue on silica, eluting with diethyl ether: hexane 1:9 gave a yellow oil which consisted of 2,2-dimethyl-5-(3-oxo9-trimethylsilylnon-8-ynyl)-5-n-propyl-1,3-dioxane and 7-oxo-1-trimethylsilyloct-1-yne in the ratio of 3:1 (1.4 g.). The above mixture in tetrahydrofuran (25 ml.) and hydrochloric acid (50 ml., 1N solution) was stirred vigorously at 20° for 1 hour. The tetrahydro- furan was removed in vacuo and the residue was extracted into diethyl ether. The ethereal extracts were dried over magnesium sulphate and the solvent was removed in vacuo. 4-n-Propyl-1-(6-trimethylsilylhex-5-ynyl)-2,6-dioxabicyclo[2.2.2]octane was obtained as a colourless oil (1.06 g.) and was used without further purification.

Mass spectrum (Chemical Ionisation) M+1 309

(iv) Tetrabutylammonium fluoride solution (1.0M.,solution 4.0 ml.) was added to a stirred solution of 4-n-propyl-1-(6-trimethylsilylhex-5-ynyl)-2,6-dioxabicyclo[2.2.2]octane in dry tetrahydrofuran (40 ml.) at 20° and the mixture was stirred for 1 hour. The solvent was removed in vacuo and the residue was extracted with diethyl ether and water. The ethereal extracts were dried over anhydrous magnesium sulphate and evaporated in vacuo. The residue was chromatographed on alumina eluting with dichloromethane: hexane 1:9, saturated with ammonia. 1-(Hex-5-ynyl)-4-n-propyl-2,6-dioxabicyclo[2.2.2]octane was obtained as a colourless oil (0.45 g.)

EXAMPLE XXXVII

1-[(Z)-1-Fluoro-3.3-dimethylbut-1-enyl]-4-propyl-2,6,7-trioxabicyclo[2.2.2]octane-3-carbonitrile i) A mixture of ethyl bromofluoroacetate (25 g) (Fluorochem.) and triethylphosphite (30 ml) was heated at 150° in an apparatus set-up for fractional distillation, until production of bromoethane ceased. Distillation of the residue, under reduced pressure, then gave ethyl diethylphosphonofluoroacetate as a colourless oil (9.05 g, b.p. 80°–88°, 0.1 mm Hg).

ii) n-Butyllithium (4.8 ml of a 1.6M solution in hexane) was added to a stirred solution of diisopropylamine (1.1 ml) in tetrahydrofuran (15 ml) at 0° C. under nitrogen. The resulting mixture was maintained at 0° C. for 0.5 hour and then cooled to –70° when a solution of ethyl diethylphosphonofluoroacetate (1.7 g) in tetrahydrofuran (5 ml) was added. After a further 0.5 hour at –70° trimethylacetaldehyde (0.76 ml) was added neat and the resulting mixture was allowed to warm to room temperature over 5 hours. After this time, water (5 ml) was added and the bulk of the solvent was removed under reduced pressure. The residue was partitioned between diethyl ether and water. The organic phase was separated, washed with water, 10% hydrochloric acid solution and brine before drying over anhydrous magnesium sulphate. The solvent was removed in vacuo to leave ethyl (Z)-2-Fluoro-4,4-dimethylpent- 2-enoate as a pale green oil (1.0 g).

Gas-liquid chromatography (glc): OV-17 at 100° produced one peak.

iii). Using the method described in Example XXXIII, stage iii) (Z)-2-Fluoro-4,4-dimethylpent-2-enoic acid was prepared from ethyl (Z)-2-fluoro-4,4-dimethylpent-2-enoate.

iv) Using the method described in Example IV stages ii) and iii), 1-[(Z)-1-Fluoro-3,3-dimethylbut-1-enyl]-4-propyl-2,6,7-trioxabicyclo[2.2.2]octane-3-carbonitrile was prepared from 3-formyl-3-n-propyl-oxetane and (Z)-2-fluoro-4,4-dimethylpent-2-enoic acid.

Gas liquid chromatography (glc): OV-17 at 250° produced one peak.

EXAMPLE XXXVIII

4-Ethoxymethyl-1-(hex-5-ynyl)-2,6,7-trioxabicyclo[2.2.2] octane-3-carbonitrile i) To a stirred solution of 5,5-di-(hydroxymethyl)-2,2-dimethyl-1,3dioxane (5.09) (Bellstein 19, II, 93) in dry dimethylformamide (50 ml) under nitrogen, at 20°, was added sodium hydride (0.689g, 80% dispersion in oil). The mixture was stirred at 80° for 2 hours and cooled. Ethyl iodide (4.49g) in dry dimethylformamide (40 ml) was added and the mixture was heated at 110° for 3 hours. The mixture was cooled and poured into water. The aqueous mixture was extracted with diethyl ether. The ethereal extracts were washed with brine, dried over anhydrous magnesium sulphate and evaporated in vacuo. 2,2-Dimethyl-5-ethoxymethyl-5- hydroxymethyl-1,3-dioxane was obtained as a pale yellow oil (1.2 g) and was used without further purification.

ii) A mixture consisting of 2,2-dimethyl-5-ethoxymethyl-5-hydroxymethyl-1,3-dioxane (15.0 g) and Amberlyst "15" (3.0 g) in methanol (500 ml) containing water (10 ml) was refluxed with stirring for 4 hours. The mixture was filtered and the filtrate was evaporated in vacuo.

2-Ethoxymethyl-2-hydroxymethylpropan-1,3-diol was obtained as a viscous oil (10.5 g) and was used without further purification.

iii) 4-Ethoxymethyl-1-(hex-5-ynyl)-2,6,7-trioxabicyclo[2.2.2]octane-3-carbonitrile was prepared from 2-ethoxymethyl-2-hydroxymethylpropan-1,3-diol using methodology described in Example IV.

In an analogous manner 1-(hex-5-ynyl)-4-methoxymethyl-2,6,7-trioxabicyclo[ 2.2.2]octane-3-carbonitrile was prepared.

EXAMPLE XXXIX 4-t-Butyl-1-(hex-5-ynyl)-2,6,dioxa-7-thiabicyclo[2.2.2]octane 4-t-Butyl-1-(hex-5-ynyl)-2,6,-dioxa-7-thiabicyclo[2.2.2]octane was prepared from trimethyl orthohept-6-ynoate and 2,2-di-(hydroxymethyl)-3,3-dimethylbutan-1-thiol (European Patent 216625) using methodology described in European Patent 216625.

EXAMPLE XL 1-(3-Methylhex-5-ynyl)-4-n-propyl-2,6,7-trioxabicyclo[2.2.2]octane-3-carbonitrile i) 2-Methylpent-4-ynyl methanesulphonate was prepared from 2-methylpent-4-yn-1-ol (ref. E. Buchta and H. Schlesinger Chem. abs. 51: 1104i) using the methodology described in Example II, stage (i).

ii) A solution diethyl malonate (46 g) in dry toluene (500 ml) was stirred at 0°, under nitrogen. Sodium hydride (8.6 g of 80% dispersion in liquid paraffin) was added carefully and the mixture was stirred at 100° for 1 hour. The mixture was cooled and 2-methylpent-4-ynyl methanesulphonate (10.2 g) was added and the mixture was refluxed, with stirring for 3 hours. The mixture was cooled, poured into water and the aqueous mixture was extracted with diethyl ether. The ethereal extracts were washed with water, dried over anhydrous magnesium sulphate and evaporated in vacuo. The excess diethyl malonate was removed by distillation at reduced pressure and the residue was purified by chromatography on silica, eluting with 7.5% diethyl ether in hexane.

Diethyl (2-methylpent-4-ynyl)malonate was obtained as a colourless oil (6.5 g).

Gas liquid chromatography (g.l.c.) : OV 17 at 160° produced one peak.

Mass Spectrum (MS), Chemical Ionisation M+1 241

4-Methylhept-6-ynoic acid was prepared from diethyl (2-methylpent-4-ynyl)malonate using methodology described in stages (iii) and (iv) of Example XVII.

1-(3-Methylhex-5-ynyl)-4-n-propyl-2,6,7-trioxabicyclo[2.2.2]octane-3-carbonitrile was prepared from 4-methylhept-6-ynoic acid and 3-formyl-3-n-propyl-oxetane using methodology described in Example IV.

Using stages (II) and (iii) of Example XXX and starting from (S)-4-methyl-6-oxoheptanoic acid (J. Wolinsky and D. Chan *J. Amer. Chem. Soc.*, 1963 85,937), (S)-4-methylhept-6-ynoic caid was prepared 1-[(S)-3-Methylhex-5-ynyl]-4-n-propyl-2,6,7-trioxabicyclo[2.2.2]-octane- 3-carbonitrile was prepared from (S)-4-methylhept-6-ynoic acid using methodology described in Example IV.

Starting from 3-butyl-3-formyloxetane and 4-methylhept-6-ynoic acid, 4-i-butyl-1-(3-methylhex-5-ynyl)-2,6,7-trioxabicyclo[2.2.2]- octane-3-carbonitrile was prepared.

EXAMPLE XLI 1-(t-Butylthiomethyl)-4-n-propyl-2,6,7-trioxabicyclo[2.2.2]octane-3-carbonitrile Using stages (i) and (ii) of Example XIII and starting from t-butylthiol and ethyl bromoacetate, t-butylthioacetic acid was prepared.

1-(t-butylthiomethyl)-4-n-propyl-2,6,7-trioxabicyclo[2.2.2]octane-3-carbonitrile was prepared from t-butylthioacetic acid and 3-formyl-3-n-propyloxetane using methodology described in Example IV.

EXAMPLE XLII 1-(Hept-5-ynyl)-4-n-propyl-2,6,7-trioxabicyclo[2.2.2]octane n-Butyllithium (1.7 ml, 1.6M solution in hexane) was added dropwise to a stirred solution of 1-(hex-5-ynyl)-4-n-propyl-2,6,7-trioxabicyclo[2.2.2]octane (0.65 g) in dry tetrahydrofuran (25 ml) at 0°, under a current of nitrogen. The mixture was stirred at 0° for 15 minutes and then methyl iodide (0.18 ml) was added. The reaction mixture was stirred at 0° for 1 hour and then evaporated in vacuo. The residue was partitioned between diethyl ether and water. The ethereal extracts were dried over anhydrous magnesium sulphate and the solvent was removed in vacuo. The residue was purified by chromatography on alumina, eluting with 1:10 dichloromethane: hexane, saturated with ammonia. 1-(Hept-5-ynyl)-4-n-propyl-2,6,7trioxabicyclo[2.2.2]octane was obtained as a colourless crystalline solid (0.23 g) {contained 15% of 1-(hex-5-ynyl)-4-n-propyl-2,6,7-trioxabicyclo[2.2.2]octane).

EXAMPLE XLIII 4-(2,2-Dichlorocyclopropymethyl)-1-(hex-5-ynyl)-2,6,7-trioxabicyclo[2,2.2]octane i) 2-Hydroxymethyl-2-(prop-2-enyl)propan-1,3-diol triacetate (2.2 g) (Example XVII) was heated at 130°, with stirring. Sodium trichloroacetate (5.0 g) was added over 2 hours and the reaction mixture was heated at 155° for 24 hours. The mixture was cooled and partitioned between diethyl ether and water. The ethereal extracts were dried over anhydrous magnesium sulphate and evaporated in vacuo. The residue was purified by chromatography on silica, eluting with diethyl ether:hexane, 1:4.

2-(2,2-Dichlorocyclopropylmethyl)-2-hydroxymethyl-propan-1,3-diol triacetate was obtained as a colourless oil (1.4 g).

Mass Spectrum (Chemical Ionisation): Ammonia as Ionising Gas. M+18 372.

ii) Using methodology described in Example I, stage (i), 2-(2,2-dichlorocyclopropylmethyl)- 2-hydroxymethylpropan-1,3-diol was prepared from 2-(2,2-dichlorocyclopropylmethyl)-2-hydroxymethyl-propan-1,3-diol triacetate.

iii) Using methodology described in Example VI, Method 2, 4-(2,2-dichlorocyclopropylmethyl)- 1-(hex-5-ynyl)-2,6,7-trioxabicyclo[2.2.2]octane was prepared from 2-(2,2-dichlorocyclopropylmethyl)-2-hydroxymethylpropan-1,3-diol and trimethyl orthohept-6-ynoate.

| Formulations | |
|---|---|
| 1. Emulsifiable Concentrate | |
| Compound of formula (I) | 10.00 |
| Ethylan KEO | 20.00 |
| Xylene | 67.50 |
| Butylated Hydroxyanisole | 2.50 |

-continued

| | Formulations | |
|---|---|---|
| 2. | Wettable Powder | 100.00 |
| | Compound of formula (I) | 25.00 |
| | Attapulgite | 69.50 |
| | Sodium isopropylbenzene sulphonate | 0.50 |
| | Sodium salt of condensed naphthalene sulphonic acid | 2.50 |
| | Butylated hydroxytoluene | 2.50 |
| | | 100.00 |
| | Compound of formula (I) | 0.50 |
| | Butylated Hydroxyanisole | 0.10 |
| 3. | Talc | 99.40 |
| | | 100.00 |
| 4. | Bait | |
| | Compound of formula (I) | 40.25 |
| | Icing Sugar | 59.65 |
| | Butylated hydroxy toluene | 0.10 |
| | | 100.00 |
| 5. | Lacquer | |
| | Compound of formula (I) | 0.1 |
| | Piperonyl Butoxide | 0.5 |
| | Butylated Hydroxyanisole | 10.1 |
| | High aromatic white spirit | 92.0 |
| | | 100.00 |
| 6. | Aerosol | |
| | Compound of formula (I) | 0.30 |
| | Butylated Hydroxy anisole | 0.10 |
| | 1,1,1-Trichloroethane | 4.00 |
| | Odourless Kerosene | 15.60 |
| | Arcton 11/12. 50:50 mix | 80.00 |
| | | 100.00 |
| 7. | Spray | |
| | Compound of formula (I) | 0.1 |
| | Butylated Hydroxyanisole | 0.1 |
| | Xylene | 10.0 |
| | Odourless Kerosene | 89.8 |
| | | 100.00 |
| 8. | Potentiated Spray | |
| | Compound of formula (I) | 0.1 |
| | Piperonyl Butoxide | 0.5 |
| | Butylated Hydroxyanisole | 0.1 |
| | Xylene | 10.1 |
| | Odourless Kerosene | 89.2 |
| | | 100.00 |

BIOLOGICAL ACTIVITIES

The following examples illustrate, in a non-limiting manner, the pesticidal activity of compounds of formula (I).

Spray Tests

The activity of the compounds of the invention were tested by dissolving the compounds in acetone (5%) and then diluting in water: 'Synperonic' (94.5%: 0.5%) to give a water emulsion. The solution was then used to treat the following insects.

Musca domestica 20 female Musca were contained in a cardboard cylinder with gauze over both ends. Solution containing the compound was sprayed onto the insects so enclosed and mortality assessed after 48 hours at 25°.

The following compounds were active at <1000 p.p.m. 4, 5, 14, 20, 21, 22, 23, 24, 25, 26, 28, 32, 43, 44, 45, 50, 53, 54, 56, 69, 71, 72, 76, 77, 82, 88, 89.

The following compounds were active at <200 p.p.m. 6, 9, 10, 11, 12, 13, 15, 16, 17, 29, 30, 31, 33, 34, 46, 47, 48, 52, 57, 58, 59, 60, 61, 62, 63, 64, 65, 68, 74, 75, 78, 79, 80, 81, 83, 84, 85, 90

Sitophilus granarius and Tribolium castaneum 20 adult Sitophilus and Tribolium were added to 10 g wheat which had been previously treated with 2 ml of the solution containing the compounds. Mortality was assessed after 6 days at 25° C.

The following compounds were active against Sitophilus granarius at <1000 p.p.m.: 7, 10, 19, 22, 23, 25, 26, 27, 32, 43, 44, 50, 56, 69, 82, 85, 88, 89, 90.

The following compounds were active against Sitophilus granarius at <200 p.p.m.: 3, 4, 5, 6, 9, 12, 14, 15, 16, 17, 29, 30, 31, 33, 34, 45, 47, 48, 53, 54, 57, 58, 59, 60, 61, 62, 68, 72, 74, 75, 76, 77, 78, 79, 80, 81.

The following compounds were active against Tribolium castaneum at <1000 p.p.m.: 4, 6, 10, 14, 17, 33, 53, 57, 58, 65, 71, 76, 79, 82, 84

The following compounds were active against Tribolium castaneum at <200 p.p.m.: 9, 12, 15, 16, 34, 46, 63, 74, 75

Myzus persicae 10 adult Myzus were placed on a leaf disc of chinese cabbage. 24 hours later the disc was sprayed with a solution containing the compound. Mortality was assessed after 2 days at 25°.

The following compounds were active at <1000 p.p.m.: 4, 9, 17, 37, 46, 53, 56, 60, 71, 77, 78, 79, 80, 81, 84.

The following compounds were active at <200 p.p.m.: 6, 45, 47, 48, 57, 58, 59, 62, 63, 74, 75, 76.

Plutella xylostella

7 Plutella larvae were sprayed with the solution containing the compound and added to a chinese cabbage leaf which had been similarly sprayed and left to dry. Alternatively 8–10 Plutella larvae were put onto leaf discs and sprayed with the solution containing the compound. Mortality was assessed after 2 days at 25°.

The following compounds were active at <1000 p.p.m.: 15, 16, 25, 29, 31, 33, 34, 35, 48, 55, 56, 58, 59, 65, 68, 71, 75, 77, 78, 79, 80, 81, 83, 85, 87

The following compounds were active at <200 p.p.m.: 9, 12, 13, 46, 47, 57, 74

Tetranychus urticae

Leaf discs containing mixed population of Tetranychus urticae were sprayed with the solution of the compound. Mortality was assessed after 2 days at 25° C.

The following compounds were active at <1000 p.p.m.: 78, 81, 83, 90

The following compounds were active at <200 p.p.m.: 60, 80

Additional spray tests

The activities of the compounds were investigated further. The compounds were dissolved in acetone (75%) and water (25%) was added. The solution was then used to spray the following insects:

Aphis fabae

A mixed population of *Aphis fabae* was tested on Nasturtium leaf.

The following compounds were active at <1000 p.p.m.: 4, 6, 13, 16, 17, 25, 26, 29, 30, 31, 33, 46, 47, 50, 54, 63, 65

Macrosteles fascifrons

Adult Macrosteles fascifrons were tested on wheat seedlings.

The following compounds were active at <1000 p.p.m.: 6, 9, 13, 16, 17, 23, 25, 26, 29, 31, 33, 34, 46, 47, 63, 65, 68

Tetranychus urticae

A mixed population of *Tetranychus urticae* was tested on bean leaves. The following compounds were active at <1000 p.p.m.: 5, 9, 16, 30, 31, 33, 46, 47, 50, 65, 68

Diabrotica undecimpunctata

3rd Instar *Diabrotica undecimpunctata* were tested on filter paper.

The following compounds were active at <1000 p.p.m.: 3, 4, 5, 6, 13, 16, 17, 23, 25, 26, 29, 30, 31, 33, 34, 46, 47, 53, 63, 65, 68

Topical Application Tests

The activity of compounds of the invention against unanaesthatised female *Musca domestica* (WRL strain) was demonstrated by the topical application to the test insect of a solution of the compound under test with piperonyl butoxide in butanone. Mortality was assessed at 48 hours.

The following compounds were active at 1 μg: 9, 10, 11, 12, 13, 15, 17, 29, 30, 31, 33, 34, 47, 52, 63, 64, 68, 83, 84, 85.

The activity of compounds of the invention against anaesthetised male *Periplaneta americana* was demonstrated by the topical application to the test insect of a solution of the compound under test in butanone. Mortality was assessed after 6 days.

The following compounds were active at <50 μg: 2, 6, 16, 17, 25, 31, 39, 83

The activity of compounds of the invention against anaesthetised male *Blattella germanica* was demonstrated by topical application to the test insect of a solution of the compound under test in butanone. Mortality was assessed after 6 days.

The following compounds were active at <5 μg: 6, 9, 12, 14, 15, 16, 17, 20, 29, 30, 31, 33, 34, 45, 46, 48, 56, 57, 58, 59, 60, 61, 62, 63, 65, 66, 67, 71, 72, 74, 75, 83, 84, 90.

Nematucidal activity

Meloidogyne incognita

Selected compounds of the invention were assayed on freshly hatched J2 *Meloidogyne incognita*. The test solution comprised 1% acetone with 100 p.p.m. Triton X -100. Activities were assessed after 24 hours.

The following compounds were active at elss than 100 p.p.m.: 6, 16, 17, 26.

Mammalian toxicity

The toxicity of compounds of the invention was determined by oral intubation of Charles River CD1 mice, fasted for 3 hours. The compounds were administered as solutions in DMSO at 200 mg/10 ml/kg, 20 mg/10 ml/kg and 2 mg/10 ml/kg. Toxicity was assessed over a 14 day period after dosing.

The following compounds gave an $LD_{50} > 200$ mgkg$^{-1}$ 17, 60

The following compounds gave an LD50 in the region of 20–200 mgkg$^{-1}$ 16, 75

APPENDIX 1

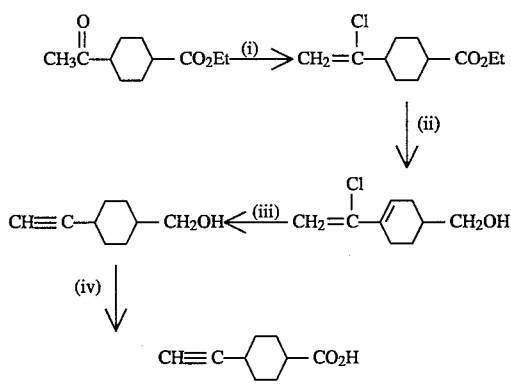

(i) PCl$_5$, pyridine
(ii) LiAlH$_4$, Et$_2$O
(iii) n-BuLi, Thf
(iv) Pyridinium dichromate, Dmf.

APPENDIX 2

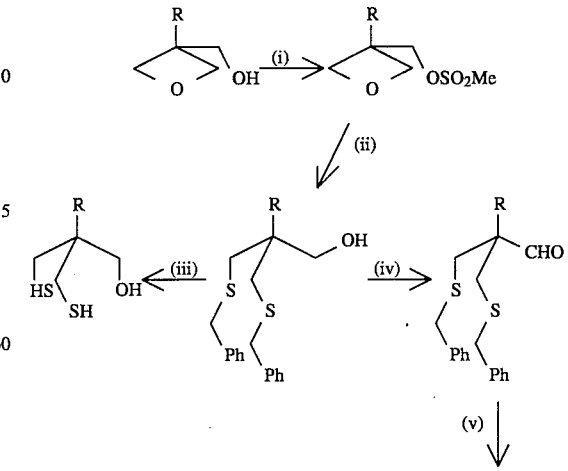

-continued
APPENDIX 2
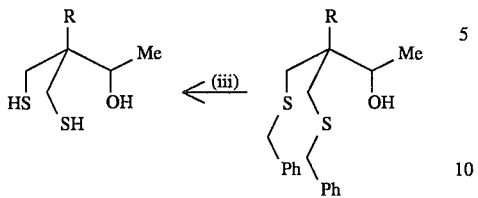
(i) MeSO$_2$Cl, pyridine
(ii) PhCH$_2$SH, NaH, Dimethylformamide
(iii) Na, liquid NH$_3$
(iv) Pyridinium chlorochromate, sodium acetate, CH$_2$Cl$_2$
(v) MeMgI, Et$_2$O
APPENDIX 3
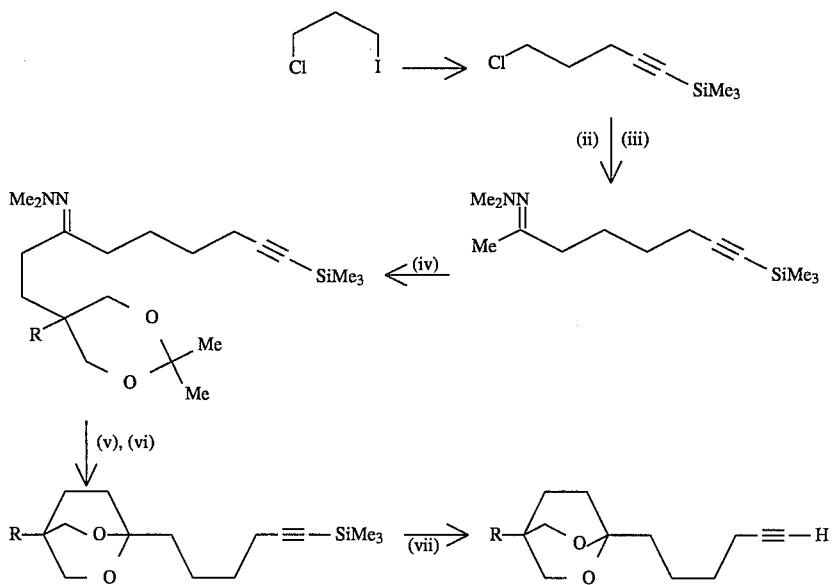
(i) Me$_3$SiC≡CH, n-BuLi, Thf
(ii) NaI, MeCOEt
(iii) , n-BuLi, Thf
(iv) , n-BuLi, Thf
(v) Silica gel
(vi) Thf, hydrochloric acid (1N solution)
(vii) (n-Bu)$_4$NI, Thf
APPENDIX 4
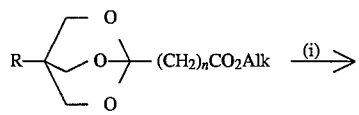
-continued
APPENDIX 4
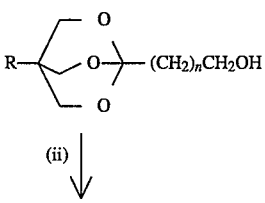
(ii) ↓

-continued
APPENDIX 4

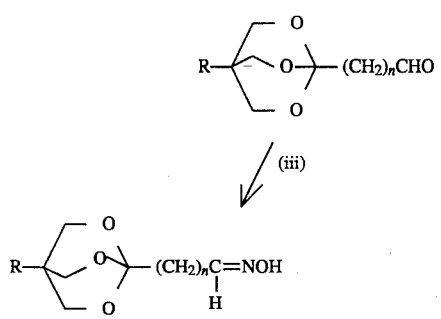

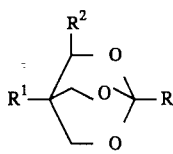

(i) LiAlH$_4$, Et$_2$O, 20°–30°
(ii) (COCl)$_2$, CH$_2$Cl$_2$, DMSO, NEt$_3$, –70° to 20°,
(iii) MeOCH$_2$CH$_2$OMe, NH$_2$OHHCl, Na$_2$CO$_3$, H$_2$O, 20°–30°

TABLE I

Trioxabicyclo-octanes

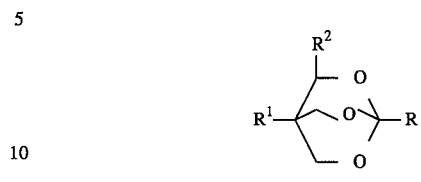

| Compound No. | R | R$^1$ | R$^2$ | Synthetic Method Example |
|---|---|---|---|---|
| 1 | Pent-4-ynyl | n-Pr | H | I |
| 2 | Hex-5-ynyl | n-Pr | H | II |
| 3 | Pent-4-ynyl | n-Pr | CF$_3$ | III |
| 4 | Hex-5-ynyl | n-Pr | CF$_3$ | III |
| 5 | Pent-4-ynyl | n-Pr | CN$^3$ | IV |
| 6 | Hex-5-ynyl | n-Pr | CN | IV |
| 7 | Pent-4-ynyl | Cyclohexyl | H | V |
| 8 | Hex-5-ynyl | Cyclohexyl | H | V |
| 9 | Hex-5-ynyl | t-Bu | H | VI |
| 10 | 6-Trimethyl-silylhex-5-ynyl | t-Bu | H | VII |
| 11 | 4-Ethynylcyclohexyl | n-Pr (isomer mixture) | H | VIII |
| 12 | 4-Ethynylcyclohexyl | t-Bu (isomer mixture) | H | IX |
| 13 | 3,3-Dimethylbut-1-ynyl | t-Bu | H | X |
| 14 | 3,3-Dimethylbut-1-ynyl | n-Pr | CN | X |
| 18 | 2-(Prop-2-ynyl-thio)ethyl | n-Pr | H | XIII |
| 19 | 2-(Prop-2-ynyl-thio)ethyl | t-Bu | H | XIII |
| 20 | 2-(Prop-2-ynyl-thio)ethyl | n-Pr | CN | XIII |
| 21 | 2-(Prop-2-ynyl-oxy)ethyl | n-Pr | H | XIV |
| 22 | 2-(Prop-2-ynyl-oxy)ethyl | t-Bu | H | XIV |
| 23 | 2-(Prop-2-ynyl-oxy)ethyl | n-Pr | CN | XIV |
| 24 | But-3-ynyloxy-methyl | n-Pr | H | XV |
| 25 | But-3-ynyloxy-methyl | t-Bu | H | XV |
| 26 | But-3-ynyloxy-methyl | n-Pr | CN | XV |
| 27 | Hept-6-ynyl | t-Bu | H | XVI |
| 28 | Hept-6-ynyl | n-Pr | H | XVI |
| 29 | Hex-5-ynyl | n-Bu | CN | IV |

TABLE I-continued

Trioxabicyclo-octanes

| Compound No. | R | R$^1$ | R$^2$ | Synthetic Method Example |
|---|---|---|---|---|
| 30 | Hex-5-ynyl | 2-Methyl-prop-2-enyl | CN | IV |
| 31 | Hex-5-ynyl | Prop-2-enyl | CN | XVII |
| 32 | But-3-ynyloxy-methyl | Prop-2-enyl | CN | XVII |
| 33 | Hex-5-ynyl | But-3-enyl | CN | XVII |
| 34 | 4-Methylhex-5-ynyl | t-Bu | H | XVIII |
| 35 | 2-(But-3-ynyloxy)ethyl | n-Pr | H | XIX |
| 36 | Oct-7-ynyl | n-Pr | H | II |
| 37 | 1-(But-3-ynyloxy)ethyl | n-Pr | H | XIX |
| 38 | 7-Methoxyhept-5-ynyl | n-Pr | H | XX |
| 39 | 7-Methoxyhept-5-ynyl | t-Bu | H | XXI |
| 40 | But-3-ynyloxy-carbonyl | n-Pr | H | XXII |
| 41 | N-(Prop-2-ynyl)carbamoyl | n-Pr | H | XXIII |
| 42 | Prop-2-ynyloxy-carbonylmethyl | n-Pr | H | XXIV |
| 43 | But-3-ynylthio-methyl | n-Pr | H | XXV |
| 44 | But-3-ynylthio-methyl | t-Bu | H | XXV |
| 47 | Hex-5-ynyl | t-Bu | CN | IV |
| 48 | Hex-5-ynyl | i-Bu | CN | IV |
| 49 | Hex-5-ynyl | MeOCH$_2$ | CN | XXXVIII |
| 50 | Hex-5-ynyl | EtOCH$_2$ | CN | XXXVIII |
| 51 | N-prop-2-ynyl-2-acetamido | n-Pr | H | XXVI |
| 52 | 1-Methylhex-5-ynyl | n-Pr | H | XXVII |
| 53 | 1-Methylhex-5-ynyl | t-Bu | H | XXVII |
| 54 | 1-Methylhex-5-ynyl | n-Pr | CN | XXVII |
| 55 | 6-Methoxycarbonyl-hex-5-ynyl | n-Pr | H | XXVIII |
| 56 | Hex-5-ynyl | Ph | H | VI |
| 59 | 3-Methylhex-5-ynyl | n-Pr | CN | XL |
| 60 | 2-Methylhex-5-ynyl | n-Pr | CN | XXX |
| 61 | 3,3-Dimethylbut-1-ynyl | i-Bu | CN | X |
| 63 | 4-Ethynylcyclohexyl | n-Pr | CN | IX |
| 64 | (E/Z)-6-(Trimethylsilyl)hex-3-en-5-ynyl | n-Pr | CN | XXXII |
| 65 | (E/Z)-Hex-3-en-5-ynyl | n-Pr | CN | XXXII |
| 66 | (E/Z)-7-Methoxyhept-3-en-5-ynyl | n-Pr | CN | XXXII |
| 67 | (E/Z)-7-Hydroxyhept-3-en-5-ynyl | n-Pr | CN | XXXII |
| 68 | (E)-Hex-1-en-5-ynyl | t-Bu | CN | XXXIII |
| 69 | Prop-2-ynyloxyimino-methyl | n-Pr | H | XXXIV |
| 70 | 2-(But-2-ynoyloxy)ethyl | n-Pr | H | XXXV |
| 74 | trans-4-Ethylnyl-cyclohexyl | t-Bu | H | IX |
| 75 | cis-4-Ethynylcyclo-hexyl | t-Bu | H | IX |
| 77 | 4-Methylhex-5-ynyl | n-Pr | CN | XVIII |

TABLE I-continued

Trioxabicyclo-octanes

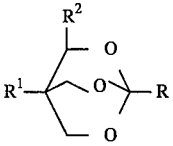

| Compound No. | R | $R^1$ | $R^2$ | Synthetic Method Example |
|---|---|---|---|---|
| 78 | Hex-5-ynyl | Phenyl | CN | IV |
| 79 | Hex-5-ynyl | Cyclopropyl-methyl | CN | IV |
| 80 | 3-Methylhex-5-ynyl | i-Bu | CN | XL |
| 81 | (S)-3-Methylhex-5-ynyl | n-Pr | CN | XL |
| 82 | 2-Methylhex-5-ynyl | Prop-2-enyl | CN | XXX |
| 83 | 3,3-Dimethylbutyl | t-Bu | H | X |
| 84 | 3,3-Dimethylbutyl | n-Pr | CN | X |
| 85 | E-3,3-Dimethylbut-1-enyl | n-Pr | CN | X |
| 86 | trans-2-t-Butyl-cyclopropyl | n-Pr | CN | X |
| 87 | t-Butylthiomethyl | n-Pr | CN | XLI |
| 88 | Z-3,3-Dimethyl-1-fluoro-but-1-enyl | n-Pr | CN | XXXVII |
| 90 | Hept-5-ynyl | n-Pr | H | XLII |
| 91 | Hex-5-ynyl | 2,2-Dichloro-cyclopropyl-methyl | H | XLIII |

TABLE II

Other Bicyclo-octanes

| Compound No. | R | $R^1$ | $R^2$ | X | Y | Z | Synthetic Method Example |
|---|---|---|---|---|---|---|---|
| 15 | Hex-5-ynyl | t-Bu | H | S | O | O | XXXIX |
| 16 | Hex-5-ynyl | n-Pr | H | S | S | O | XI |
| 17 | Hex-5-ynyl | n-Pr | H | S | S | S | XII |
| 45 | Hex-5-ynyl | n-Bu | H | S | S | O | XI |
| 46 | Hex-5-ynyl | t-Bu | H | S | S | O | XI |
| 57 | Hex-5-ynyl | i-Bu | H | S | S | O | XI |
| 58 | Hex-5-ynyl | n-Pr | Me | S | S | O | XXIX |
| 62 | But-3-ynyl-oxymethyl | n-Pr | H | S | S | S | XXXI |
| 71 | Hex-5-ynyl | i-Bu | H | S | S | S | XII |
| 72 | Hex-5-ynyl | Ph | H | S | S | O | XI |
| 73 | Hex-5-ynyl | n-Pr | H | $CH_2$ | O | O | XXXVI |
| 76 | Hex-5-ynyl | Et | H | S | S | S | XII |
| 89 | Hex-5-ynyl | Cyclo-propyl-methyl | H | S | S | O | XI |

TABLE III

Characterising Data for Trioxabicyclo-octanes

| Compound No. | m.p. | Mass Spectrum Chemical Ionisation M + 1 | Nuclear Magnetic Resonance Spectrum $^1$H(ppm from TMS in $CDCl_3$, integral, multiplicity, $J_{Hz}$) |
|---|---|---|---|
| 1 | Solid | 225 | 3.90, 6H, s; 2.4–1.6, 7H, m; 1.3–0.7, 7H, m. |
| 2 | Oil | 239 | 3.90, 6H, s; 2.17, 2H, 2; 1.95, 1H, t; 1.75–1.45, 6H, m; 1.35–1.05, 4H, m; 0.95, 3H, t. |
| 3 | 76° | 293 | 4.35, 1H, qd; 4.15, 1H, dd; 4.0–3.75, 3H, m; 2.25, 2H, td; 2.0–1.1, 9H, m; 0.9, 3H, t. |
| 4 | 57° | 307 | 4.35, 1H, qd; 4.15, 1H, dd; 4.0–3.75, 3H, m; 2.15, 2H, m; 1.95, 1H, t; 1.8–1.1, 10H, m; 0.9, 3H, t. |
| 5 | Oil | 250 | 4.8, 1H, d; 4.2, 1H, dd; 4.05–3.85, 3H, m; 2.2, 2H, td; 1.95, 1H, t; 1.9–1.55, 4H, m; 1.45–1.15, 4H, m; 0.95, 3H, t. |
| 6 | Oil | 264 | 4.8, 1H, d; 4.2, 1H, dd; 4.05–3.8, 3H, m; 2.15, 2H, m; 1.9, 1H, t; 1.85–1.1, 10H, m; 0.95, 3H, t |
| 7 | 82° | 265 | 3.95, 6H, s; 2.25, 2H, td; 1.9, 1H, t; 1.85–0.8, 15H, m. |
| 8 | Oil | 279 | 3.95, 6H, s; 2.2, 2H, m; 1.95, 1H, t; 1.85–0.8, 17H, m. |
| 9 | 75 | 253 | 4.00, 6H, s; 2.20, 2H, m; 1.95, 1H, t, 1.70–1.50, 6H, m; 0.85, 9H, s. |
| 10 | 87–90.5° | 325 | 4.00, 6H, s; 2.20, 2H, 2; 1.70–1.50, 6H, m; 0.85, 9H, s; 0.15, 9H, s. |
| 11 | Oil | 265 | 3.92, 6H, s; 2.25–1.10, 15H, m; 0.85, 3H, t, $J_{Hz}$5. |
| 12 | 126–132 | 2 components trans and cis in ratio 4:1 279 | trans isomer:- 4.01, 6H, s; 2.1–1.1, 11H, m, 0.90, 9H, s cis isomer:- 4.00, 6H, s; 2.2–1.1, 11H, m; 0.90, 9H, s. |
| 13 | 204–206° | 253 | 4.10, 6H, s; 1.25, 9H, s; 0.90, 9H, s. |
| 14 | 123–124° | 264 | 4.85, 1H, d; 4.20, 1H, m; 4.00, 3H, m; 1.30, 4H, N; 1.25, |

TABLE III-continued

Characterising Data for Trioxabicyclo-octanes

| Compound No. | m.p. | Mass Spectrum Chemical Ionisation M + 1 | Nuclear Magnetic Resonance Spectrum $^1$H(ppm from TMS in CDCl$_3$, integral, multiplicity, J$_{Hz}$) |
|---|---|---|---|
| 18 | Oil | 257 | 9H, s; 0.95, 3H, t, 7. 3.95, 6H, s; 3.25, 2H, d, 1.5; 2.85, 2H, m; 2.20, 1H, t, 1.5; 2.05, 2H, m; 1.20, 4H, m; 0.90, 3H, t, 7. |
| 19 | 76–82° | 271 | 4.00, 6H, s; 3.25, 2H, d, 1.5; 2.80, 2H, m; 2.20, 1H, t, 1.5; 2.00, 2H, m; 0.90, 9H, s. |
| 20 | Oil | 282 | 4.80, 1H, d; 4.20, 1H, m; 4.00, 3H, m; 3.25, 2H, d, 1.5; 2.80, 2H, m; 2.25, 1H, t, 1.5; 2.05, 2H, m; 1.30, 4H, m; 0.95, 3H, t, 7. |
| 21 | Solid <35° | 241 | 4.15, 2H, d; 3.90, 6H, s; 3.65, 2H, t, 6; 2.40, 1H, t; 2.00, 2H, t, 6; 1.20, 4H, m; 0.90, 3H, t, 6. |
| 22 | Oil | 255 | 4.15, 2H, d; 4.00, 6H, s; 3.65, 2H, t; 2.4, 1H, t; 2.05, 2H, t; 1.90, 9H, s. |
| 23 | Oil | 266 | 4.80, 1H, d, 2.7; 4.2–3.9, 6H, m; 3.65, 2H, t, 5; 2.45, 1H, t; 2.2, 2H, t, 5; 1.4–1.15, 4H, m; 0.9, 3H, t. |
| 24 | 64° | 241 | 4.00, 6H, s; 3.70, 2H, t, 6; 3.55, 2H, s; 2.55, 2H, td; 1.95, 1H, t; 1.25, 4H, m; 0.90, 3H, t, 7. |
| 25 | Oil | 255 | 4.05, 6H, s; 3.7, 2H, t; 3.55, 2H, s; 2.5, 2H, td, 1.95, 1H, t; 0.85, 9H, s. |
| 26 | 67.4° | 266 | 4.8, 1H, d, 2.65; 4.25, 1H, m; 4.10–3.95, 3H, m; 3.70, 2H, t; 3.60, 2H, s; 2.50, 2H, td; 2.00, 1H, t; 1.45–1.20, 4H, m; 1.00, 3H, t, 7. |
| 27 | 66.2° | 267 | 3.95, 6H, s; 2.18, 2H, td; 1.94, 1H, t; 1.7–1.35, 8H, m; 0.85, 9H, s. |
| 28 | Oil | 253 | 3.95, 6H, s; 2.17, 2H, td; 1.92, 1H, t; 1.7–1.05, 12H, m; 0.88, 3H, t. |
| 29 | Oil | 278 | 4.8, 1H, d, 2.6; 4.2, 1H, 2; 4.05–3.85, 3H, m; 2.2, 2H, m; 1.95, 1H, t, 2.6; 1.75–1.15, 12H, m; 0.9, 3H, t, 7. |
| 30 | Oil | 276 | 5.05, 1H, d; 4.8, 2H, 2; 4.23, 1H, 2; 4.1–3.9, 3H, m; 2.25–2.10, 4H, m; 1.95, 1H, t; 1.75, 3H, s; 1.70–1.65, 2H, m; 1.60–1.45, 4H, m. |
| 31 | Oil | 262 | 5.75–5.5, 1H, m; 5.20, 2H, m; 4.75, 1H, d; 4.20, 1H, dd; 4.02–3.88, 3H, 2; 2.20–2.12, 4H, 2; 1.95, 1H, t; 1.75–1.65, 2H, m; 1.60–1.50, 4H, m. |
| 32 | Oil | 264 | 5.55, 1H, m; 5.22, 2H, m; 4.82, 1H, d; 4.25, 1H, dd; 4.00, 3H, m; 3.75, 2H, t; 3.60, 2H, s; 2.50, 2H, td; 2.20, 2H, d; 1.97, 1H, t. |
| 33 | Oil | 276 | 5.8–5.65, 1H, m; 5.06, 2H, m; 4.80, 1H, d; 4.20, 1H, dd; 4.05–3.90, 3H, m; 2.25–2.15, 2H, m; 2.07–1.97, 2H, m; 1.95, 1H, t; 1.75–1.65, 2H, m; 1.6–1.45, 6H, m. |
| 34 | 47–51° | 267 | 4.00, 6H, s; 2.38, 1H, m; 2.03, 1H, d; 1.75–1.35, 6H, m; 1.17, 3H, d; 0.85, 9H, s. |
| 35 | Oil | 255 | 3.90, 6H, s; 3.60, 2H, m; 3.55, 2H, t, 7; 2.45, 2H, td, 7 and 2.6; 2.00, 2H, m; 1.95, 1H, t, 2.6; 1.15, 4H, m; 0.90, 3H, t, 6.8. |
| 36 | Oil | 267 | 3.90, 6H, s; 2.15, 2H, td, 7 and 2.6; 1.95, 1H, t, 2.6; 1.7–1.2, 10H, 2; 1.15, 4H, m; 0.90, 3H, t, 6.8. |
| 37 | Oil | 255 | 3.95, 6H, s; 3.83, 1H, m; 3.65, 1H, m; 346, 1H, m; 2.45, 2H, m; 3.46, 1.95, 1H, t, 2.6; 1.20–1.15, 7H, m; 0.90, 3H, t. |
| 38 | Solid m.p. <40° | 283 | 4.10, 2H, t; 3.90, 6H, s; 3.35, 3H, s; 2.20, 2H, m; 1.65, 2H, m; 1.50, 4H, m; 1.25, 4H, m; 0.90, 3H, t, 7. |
| 39 | 47–49° | 297 | 4.19, 2H, m; 4.00, 6H, s; 3.40, 3H, s; 2.20, 2H, m; 1.60, 6H, m; 0.90, 9H, s. |
| 40 | 62.1° | 255 | 4.35, 2H, t; 4.10, 6H, s; 2.60, 2H, 2; 2.00, 1H, t; 1.22, 4H, m; 0.90, 3H, t. |
| 41 | 117° | 240 | 6.70, 1H, m; 4.10, 2H, d; 4.05, 6H, s; 2.25, 1H, t; 1.20, 4H, m; 0.90, 3H, t, 7. |
| 42 | 47° | 255 | 4.73, 2H, d; 3.95, 6H, s; 2.80, 2H, 8; 2.45, 1H, t, ; 1.15, 4H, m; 0.90, 3H, t. |
| 43 | 62° | 257 | 3.95, 6H, s; 2.85, 2H, t, 7; 2.80, 2H, s; 2.50, 2H, td; 2.00, 1H, t; 1.40, 4H, 2; 0.90, 3H, t. |
| 44 | Oil | 271 | 4.05, 6H, 9; 2.83, 2H, t, 7; 2.80, 2H, s; 2.50, 2H, td; 2.00, 1H, t; 0.85, 9H, s. |
| 47 | 59° | 278 | 4.80.1H, d; 4.35, 1H, m; 4.00, 2H, m; 3.85, 1H, m; 2.20, 2H, m; 1.95, 1H, t; 1.75, 2H, m; 1.45, 4H, m; 1.00, 9H, s. |
| 48 | oil | 278 | 4.80, 1H, 4.2–4.9, 4H, m; 2.2, 2H, m; 1.9, 1H, t; 1.8–1.5, 6H, m; 1.3, 3H, m; 1.0, 6H, m. |
| 49 | Oil | 266 | 5.00, 1H, d; 4.30–3.80, 6H, m; 3.32, 3H, s; 2.20, 2H, m; 1.95, 1H, t; 1.75, 2H, m; 1.50, 4H, m. |
| 50 | Oil | 280 | 5.02, 1H, d; 4.20–3.90, 4H, m; 3.60–3.20, 4H, m; 2.20, 2H, m; 1.95, 1H, t; 1.70, 2H, m; 1.53, 4H, m; 1.17, 3H, t, |

TABLE III-continued

Characterising Data for Trioxabicyclo-octanes

| Compound No. | m.p. | Mass Spectrum Chemical Ionisation M + 1 | Nuclear Magnetic Resonance Spectrum $^1$H(ppm from TMS in CDCl$_3$, integral, multiplicity, J$_{Hz}$) |
|---|---|---|---|
| 51 | Oil | 254 | 6.7, 1H, s; 4.1, 2H, d; 4.0, 6H, s; 2.7, 2H, s; 2.25, 1H, t; 1.20, 4H, m; 0.90, 3H, t. |
| 52 | Oil | 253 | 3.9, 6H, s; 2.2, 2H, m; 1.95, 1H, t; 1.85–1.10, 9H, m; 0.95, 3H, d, 7; 0.90, 3H, t, . |
| 53 | Oil | 267 | 3.95, 6H, s; 2.17, 2H, m; 1.95, 1H, t; 1.8–1.35, 4H, m; 1.25, 1H, m; 0.95, 3H, d, 7; 0.85, 9H, s. |
| 54 | Oil | 278 | 4.75, 1H, d, 2.6; 4.2, 1H, dd; 4.0–3.85, 3H, m; 2.2, 2H, m; 1.95, 1H, t; 1.8–1.20, 9H, m; 0.9, 6H, m. |
| 55 | 40–45° | 297 | 3.92, 6H, s; 3.75, 3H, s; 2.33, 2H, t, 7; 1.75–1.45, 6H, m; 1.3–1.05, 4H, m; 0.90, 3H, t. |
| 56 | 68° | 273 | 7.30, 3H, m; 7.15, 2H, B; 4.30, 6H, s; 2.20, 2H, m; 1.95, 1H, t; 1.80, 2H, m; 1.60, 4H, m. |
| 59 | Oil | 278 | 4.75, 1H, d; 4.15, 1H, m; 4.00–3.85, 3H, m; 2.25–2.00, 2H, m; 1.95, 1H, t; 1.80–1.15, 9H, m; 1.00, 6H, m. |
| 60 | Oil | 278 | 4.80, 1H, d; 4.15, 1H, m; 3.90, 3H, m; 2.15, 2H, m; 1.95, 1H, m; 1.80–1.10, 9H, m; 0.95, 6H, m. |
| 61 | 96° | 278 | 4.87, 1H, d; 4.25, 1H, m; 4.20–4.00, 3H, m; 1.68, 1H, heptet; 1.30, 2H, d; 1.25, 9H, s; 0.95, 6H, dd. |
| 63 | 96–97 | 290 | 4.76, 1H, d; 4.18, 1H, dd; 4.01–3.80, 3H, m; 2.25–1.03, 15H, m; 0.93, 3H, t. |
| 64 | Oil | E and Z components ratio 1:2 334 | 6.25–5.85, 1H, m; 5.50, 1H, m; 4.78, 1H, m; 4.20, 1H, m; 3.90, 3H, m; 2.50–2.15, 2H, m; 1.80, 2H, m; 1.30, 4H, m; 0.95, 3H, t; 0.22 and 0.19, 9H, s. |
| 65 | Oil | 262 | 6.35–5.90, 1H, m; 5.45, 1H, m; 4.78, 1H, m; 4.20, 1H, m; 3.95, 3H, m; 3.10 and 2.80, 1H, 2xt; 2.60–2.20, 2H, m; 1.80, 2H, m; 1.30, 4H, m; 0.95, 3H, t. |
| 66 | Oil | E and Z components ratio 1:2 306 | 6.22–5.80, 1H, m; 5.53, 1H, m; 4.80, 1H, m; 4.30–3.80, 6H, m; 3.42 and 3.38, 3H, s; 2.52–2.18, 2H, m; 1.80, 2H, m; 1.30, 4H, m; 0.90, 3H, t. |
| 67 | Oil | E and Z components in ratio 1:2 292 | 6.22–5.80, 1H, m; 5.50, 1H, m; 4.75, 1H, m; 4.40, 2H, m; 4.20, 1H, m; 3.95, 3H, m; 2.50–2.18, 2H, m; 1.80, 2H, m; 1.60, 1H, broad signal; 1.30, 4H, m; 0.95, 3H, t. |
| 68 | 75–80° | 276 | 6.20, 1H, m; 5.52, 1H, d, J15.6, Hz; 4.85, 1H, d; 4.40, 1H, dd; 4.08, 2H, m; 3.92, 1H, dd; 2.30, 4H, m; 1.98, 1H, t; 1.00, 9H, s. |
| 69 | 73–4° | 240 | 7.35, 1H, s; 4.75, 2H, d; 4.05, 6H, s; 2.46, 1H, t; 1.25, 4H, m; 0.95, 3H, t. |
| 70 | 80–1° | 269 | 4.30, 2H, t; 3.90, 6H, s; 2.10, 2H, t; 1.96, 3H, s; 1.20, 4H, m; 0.90, 3H, t. |
| 74 | 184–6° | 279 | 3.95, 6H, s; 2.22–0.95, 11H, m; 0.85, 9H, s. |
| 75 | 139–1° | 279 | 3.95, 6H, s; 2.00, 1H, m; 1.95–1.05, 10H, m; 0.85, 9H, s. |
| 77 | Oil | 278 | 4.78, 1H, d; 4.20, 1H, dd; 4.10–3.85, 3H, m; 2.45, 1H, m; 2.05, 1H, d; 1.85–1.10, 13H, m; 0.95, 3H, t. |
| 78 | Oil | 298 | 7.50–7.10, 5H, m; 5.15, 1H, d; 4.75, 1H, m; 4.35, 2H, m; 4.20, 1H, d; 2.20, 2H, m; 2.00, 1H, t; 1.85, 2H, m; 1.60, 4H, m. |
| 79 | Oil | 276 | 4.90, 1H, d; 4.20–3.90, 4H, 2; 2.20, 2H, m; 2.00, 1H, t; 1.90–1.20, 8H, m; 0.55, 3H, m; 0.15, 2H, m. |
| 80 | Oil | 292 | 4.80, 1H, d; 4.30–3.90, 4H, m; 2.15, 2H, m; 2.00, 1H, t; 1.80–1.50, 5H, m; 1.35, 3H, m; 0.95, 9H, m. |
| 81 | Oil | 278 | 4.78, 1H, d; 4.20, 1H, 2; 4.05–3.85, 3H, m; 2.13, 2H, m; 1.95, 1H, t; 1.80–1.10, 9H, m; 0.95, 6H, m. |
| 82 | Oil | 276 | 5.60, 1H, m; 5.20, 2H, m; 4.75, 1H, d; 4.15, 1H., m, 4.00, 3H, m; 2.15, 4H, m; 2.00–1.20, 6H, m; 0.95, 3H, d. |
| 83 | 169° | 257 | 4.00, 6H, s; 1.62, 2H, m; 1.32, 2H, m; 0.87, 9H, s; 0.85, 9H, s. |
| 84 | 54° | 268 | 4.77, 1H, d; 4.20, 1H, m; 3.95, 3H, m; 1.70, 2H, m; 1.35, 6H, m; 0.95, 3H, t; 0.85, 9H, s. |
| 85 | 77.5° | 266 | 6.15, 1H, d; 5.35, 1H, d; 4.82, 1H, d; 4.23, 1H, m; 4.05, 3H, m; 1.30, 4H, m; 1.00, 9H, s; 0.95, 3H, t. |
| 86 | 67.1° | 280 | 4.78, 1H, d; 4.15, 1H, m; 4.00–3.80, 3H, m; 1.40–1.20, 4H, m; 1.10–0.90, 5H, m; 0.82, 9H, s; 0.60, 1H, m; 0.42, 1H, m |
| 87 | Oil | 286 | 4.8, 1H, m; 4.3–4.0, 4H, m; 2.8, 2H, s; 1.5–1.2, 13H, m; 0.95, 3H, m. |
| 88 | Oil | 284 | 5.50, 1H, d J$_{Hz}$33; 4.88, 1H, d, J$_{Hz}$3; 4.30, 1H, dd, J$_{Hz}$9 and 3; 4.06, 3H, m; 1.5–1.2, 4H, m; 1.15, 9H, s; 0.95, 3H, t, J$_{Hz}$7. |
| 90 | 51.2° | 253 | 3.90, 6H, s; 2.15, 2H, m; 1.75, 3H, t; 1.65, 2H, m; 1.50, 4H, m; 1.20, 4H, m; 0.90, 3H, t. |

TABLE III-continued

Characterising Data for Trioxabicyclo-octanes

| Compound No. | m.p. | Mass Spectrum Chemical Ionisation M + 1 | Nuclear Magnetic Resonance Spectrum $^1$H(ppm from TMS in CDCl$_3$, integral, multiplicity, J$_{Hz}$) |
|---|---|---|---|
| 91 | 80° | 319 | 4.00, 6H, s; 2.20, 2H, m; 1.95, 1H, t; 1.80–1.30, 11H, m. |

TABLE IV

Characterising Data for other Bicyclo-octanes

| Compound No. | m.pt. | Mass Spectrum Chemical Ionisation M + 1 | Nuclear Magnetic Resonance Spectrum $^1$H(ppm from TMS in CDCl$_3$, integral, multiplicity, J$_{Hz}$) |
|---|---|---|---|
| 15 | 68° | 269 | 4.05, 4H, s; 3.00, 2H, s; 2.20, 2H, m; 1.95, 1H, t, 1.0; 1.75, 2H, m; 1.55, 4H, m; 0.90, 9H, s. |
| 16 | 62° | 271 | 4.00, 2H, m; 3.00, 4H, m; 2.20, 2H, m; 2.00, 3H, m; 1.55, 4H, m; 1.30, 4H, m; 0.95, 3H, t, 7. |
| 17 | 89–92° | 287 | 3.00, 6H, s; 2.20, 2H, m; 2.00, 3H, m; 1.90–1.10, 8H, m; 0.95, 3H, t, 7. |
| 45 | Oil | 285 | 4.00, 2H, s; 3.05, 2H, d; 2.95, 2H, d; 2.20, 2H, m; 1.92, 3H, m; 1.60, 4H, m; 1.30, 6H, m; 0.90, 3H, t, 7. |
| 46 | 53° | 285 | 4.10, 2H, s; 3.05, 4H, dd; 2.18, 2H, m; 1.95, 3H, m; 1.60, 4H, m; 0.95, 9H, s. |
| 57 | <300 | 285 | 4.05, 2H, s; 3.05, 4H, dd; 2.20, 2H, m; 2.00, 3H, m; 1.75, 1H, heptet; 1.55, 4H, m; 1.20, 2H, d; 1.00, 6H, d. |
| 58 | 44° | 285 | 4.25, 1H, q; 3.00, 4H, m; 2.20, 2H, m; 1.95, 3H, m; 1.50, 4H, m; .1.75, 7H, m; 1.00, 3H, t. |
| 62 | Oil | 299 | 3.85, 2H, s; 3.75, 2H, t; 3.00, 6H, s; 2.50, 2H, m; 1.97, 1H, t; 1.40, 4H, m; 0.97, 3H, t. |
| 71 | 37.1° | 301 | 3.10, 6H, s; 2.20, 2H, m; 2.00, 3H, m; 1.60, 5H, m; 1.40, 2H, d; 1.00, 6H, d. |
| 72 | 70.2° | 305 | 7.35, 5H, m; 4.40, 2H, s; 3.40, 4H, m; 2.20, 2H, m; 1.95, 3H, m; 1.45, 4H, m. |
| 73 | Oil | 237 | 3.8, 4H, m; 2.2, 2H, m; 2.0–1.9, 3H, m; 1.7–1.4, 8H, m; 1.3-1.0, 4H, 2; 0.9, 3H, t. |
| 76 | Oil | 273 | 3.00, 6H, s; 2.20, 2H, 2; 2.00, 3H, m; 1.90–1.50, 6H, m; 1.00, 3H, t. |
| 89 | Oil | 283 | 4.05, 2H, s; 3.10, 4H, m; 2.20, 2H, m; 2.00, 3H, m; 1.60, 4H, m; 1.25, 2H, m; 0.60, 3H, m; 0.10, 2H, m. |

We claim:

1. A compound of the formula:

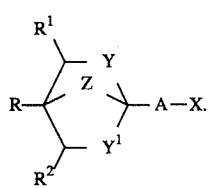

wherein R is a $C_{2-10}$ non-aromatic hydrocarbyl group or a $C_{2-10}$ non-aromatic hydrocarbyl group substituted by cyano, halo, $C_{1-4}$ alkoxy, $C_{1-4}$ haloalkoxy, or a group $S(O)_m R^3$ where $R^3$ is $C_{1-4}$ alkyl or $C_{1-4}$ haloalkyl, and m is 0, 1 or 2; $R^1$ and $R^2$ are the same or different, and each is hydrogen, halo, or a $C_{1-3}$ aliphatic group or a $C_3$ aliphatic group substituted by halo, cyano, $C_{1-5}$ alkoxycarbonyl, $C_{1-4}$ alkoxy or a group $S(O)_{m'}$, $R^4$ wherein m' is 0 1 or 2 and $R^4$ is $C_{1-4}$ alkyl, cyano, gem dimethyl or $C_{1-5}$ alkoxycarbonyl, or $R^1$ and $R^2$ and the carbon atoms to which they are attached form a $C_{5-7}$ carbocyclic ring or a $C_{5-7}$ carbocyclic ring substituted by halo, or a $C_{1-3}$ aliphatic or alkoxy group;

A-X is a group:

(i) A' C≡CX in which A' is a $C_{3-6}$ alkyl, alkenyl or alkynyl group or $C_{3-6}$ alkyl, alkenyl or alkynyl group which contains one to three hetero atoms selected from oxygen, sulphur, nitrogen, fluoro, or chloro, or A' is a $C_{3-10}$ cycloalkyl or cycloalkenyl group or a $C_{3-10}$ cycloalkyl or cycloalkenyl group which contains an oxygen, sulphur, nitrogen, fluoro or chloro atom;

(ii) BX in which B is a group $(CH_2)_2O$ or $(CH_2)_2S(O)_n$ wherein Z is 1 or 2 and n is 0, 1 or 2 or a $C_{2-6}$ alkyl, alkenyl or alkynyl group or a $C_{2-6}$ alkyl, alkenyl or alkynyl group which contains one or two oxygen and sulfur hetero atoms or double bonds but not triple bonds or both hereto atoms and double bonds interspersed in the chain or a $C_{2-6}$ aliphatic chain substituted by one to four substituents which may be the same or different and are each independently selected from hydroxy, oxo, halo, $C_{1-4}$ alkyl, $C_{1-4}$ alkoxy, an acyl group derived from a $C_{1-4}$ carboxylic acid, epoxy, a $C_{1-4}$ alkylidene group, a $C_{1-6}$ alkoxycarbonyl group, $C_{1-4}$ haloalkyl or cyano; X is hydrogen, halo, a group $SiR^5R^6R^7$ or $SnR^5R^6R^7$ wherein $R^5$ $R^6$ $R^7$ are the same or different and are each a hydrocarbyl group containing up to 8 atoms or a hydrocarbyl group containing up to 8 atoms and substituted by one to three halo, $C_{1-6}$ alkoxy, $C_{1-6}$ alkylthio, $C_{1-6}$ alkyl sulphinyl, $C_{1-6}$ alkylsulphonyl, cyano, $C_{1-6}$ acyloxy or a $C_{1-6}$ alkoxycarbonyl group or, when one or more of $R^5$ to $R^7$ is alkynyl, the alkynyl group is unsubstituted or substituted by silyl or silyl substituted by three $C_{1-4}$ alkyl groups, or X is a group $CR^8R^9R^{10}$ wherein $R^8$ and $R^9$ are the same or different and are each independently selected from hydrogen, halo, cyano, $C_{1-5}$ alkoxycarbonyl, $C_{1-4}$, alkyl, $C_{1-4}$ alkyl substituted by one to three halo atoms, cyano, $C_{1-4}$ alkoxycarbonyl, $C_{1-4}$ alkoxy or a group $S(O)_{m''}R^{11}$ wherein M" is 0, 1 or 2 and $R^{11}$ is $C_{1-4}$ alkyl, $C_{1-4}$ alkoxy or $S(O)_{m'''}R^{12}$ wherein m''' is 0, 1 or 2 and $R^{12}$ is $C_{1-4}$ alkyl or $C_{1-4}$ alkyl substituted by one to three fluoro atoms, or $R^8$ and $R^9$ and the carbon atom to which they are attached form a $C_{3-6}$ cycloalkyl ring, and $R^{10}$ is hydrogen, halo, hydroxy, cyano, $C_{1-4}$ alkoxy, $C_{1-4}$ acyloxy, $C_{1-5}$ alkoxycarbonyl, a $C_{1-9}$ hydrocarbyl group or a $C_{1-9}$ hydrocarbyl group substituted by hydroxy, cyano, $C_{1-4}$ alkoxy, $C_{1-4}$ acyloxy, $C_{1-4}$ alkoxycarbonyl, one to three halo atoms or a group $S(O)_{m''''}R^{13}$ wherein m'''' is 0, 1 or 2 and $R^{13}$ is $C_{1-4}$ alkyl or $R^{10}$ is a group $S(O)_{m'''''}R^{13}$ wherein m''''' is 0, 1 or 2 and $R^{14}$ is $C^{1-4}$ alkyl or a $C_{1-4}$alkyl substituted by one to three fluoro atoms;

Y and Y' are both $S(O)_{n''}$ wherein n' is 0, 1 or 2; and Z is $CH_2S(O)_{n''}$; wherein n" is 0, 1 or 2;

provided that when A does not contain a C≡ fragment, X is a group $CR^8R^9R^{10}$ wherein $R^8$, $R^9$, $R^{10}$ are as defined except that $R^8$ and $R^9$ are not hydrogen.

2. A compound of the formula (I) according to claim 1 wherein R is n-propyl, n-butyl, i-butyl, t-butyl or phenyl.

3. A compound of the formula (I) according to claim 1 wherein $R^1$ and $R^2$ are independently selected from hydrogen, methyl, cyano or trifluoromethyl.

4. A compound of the formula (I) according to claim 1 wherein A is a —$(CH_2)_4$ C≡C— group,

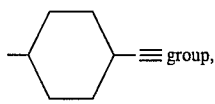

a —CH=CH$(CH_2)_2$C≡C— group, a $CH_2O(CH_2)_2$C≡C— group, a —$(CH_2)_3CH(CH_3)$C≡C— group, a —$(CH_2)_2CH(CH_3)$ $CH_2$C≡C— group, a —$CH_2CH(CH_3)(CH_2)_2$C≡C— group, a —$(CH_2)_2$CH=CHC≡C group or a —$(CH_2)_3$ C≡C— group and X is hydrogen or $C_{1-4}$ alkyl unsubstituted or substituted by an hydroxy, $C_{1-4}$ alkoxy or $C_{1-4}$ acyloxy group or one to three halo atoms.

5. A compound of the formula (I) according to claim 1 wherein A is a —$CH_2CH_2$—, —CH=CH— or a —C≡C— group and X is a group

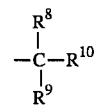

wherein $R^8$, $R^9$ and $R^{10}$ are each selected from chloro, bromo or methoxy or methyl unsubstituted or substituted by methoxy or fluoro.

6. A compound of the formula (IA):

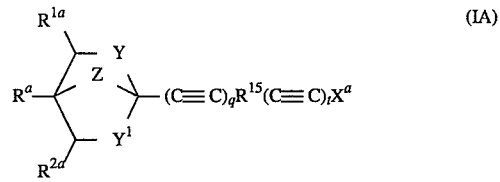

wherein $R^a$ is $C_{2-10}$ alkyl, alkenyl or alkynyl, each unsubstituted or substituted by, or methyl substituted by, cyano, halo, $C_{3-4}$ cycloalkyl, $C_{3-4}$ cycloalkyl substituted by halo, $C_{1-4}$ alkoxy unsubstituted or substituted by halo, or a group $S(O)_m$ $R^3$ as defined in claim 1 or $R^a$ is $C_{3-10}$ cycloalkyl, $C_{4-10}$ cycloalkenyl or phenyl, each unsubstituted or substituted by $C_{1-4}$ alkoxy, $C_{1-3}$ alkyl unsubstituted or substituted by up to 3 halo atoms, $C_{2-4}$ alkynyl, halo, cyano or a group $S(O)_mR^3$;

$R^{1a}$ and $R^{2a}$ are the same or different, and each is hydrogen, halo, or an aliphatic group containing up to 3 carbon atoms unsubstituted or substituted by halo, cyano, $C_{1-4}$ alkoxy or a group $S(O)_mR^4$; alkyl carbalkoxy containing up to 6 carbon atoms, or alkynyl substituted by tri-$C_{1-4}$ alkylsilyl, or $R^{1a}$ is $COO-C_4$-alkyl, cyano, gem dimethyl, or $R^{1a}$ and $R^a$ and the carbon atoms to which they are attached form a $C_{5-7}$ carbocyclic ring are unsubstituted or substituted by halo, $C_{1-3}$ alkyl or alkoxy or $C_{2-3}$ alkenyl;

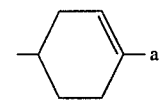

or $R^{15}$ is a single bond a group $R^{15'}$ wherein $R^{15'}$ is a group

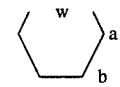

unsubstituted or substituted by one to five methyl groups or halo atoms wherein w is oxygen, a group $S(O)_p$ wherein p is 0, 1 or 2 or $(CH_2)_r$ wherein r is 1, 2 or 3 and the fragment (C≡C)$_t X^a$ is attached to the a or b position of the ring or $R^{15'}$ is an aliphatic chain containing between 1 and 8 carbon atoms in which one or two heteroatoms may be interspersed, the chain and $R^{15'}$ being unsubstituted or substituted by one to four substituents which are the same or different and are each independently selected from hydroxy, oxo, halo, $C_{1-4}$ alkyl or $C_{1-4}$ alkoxy, each unsubstituted or substituted by up to 3 halo atoms, $C_{1-4}$ acyloxy, epoxy, a $C_{1-4}$ alkylidene group, a $C_{1-6}$ carbalkoxy group, cayano, or a group $S(O)_{p'}$ $R^{4a}$ wherein p' is 0, 1 or 2 and $R^{4a}$ is $C_{1-4}$ alkyl, $X^a$ is selected from hydrogen, halo, $C_{1-10}$ hydrocarbyl unsubstituted or substituted by an hydroxy, $C_{1-4}$ alkoxy or $C_{1-4}$ acyloxy group or one to three halo atoms, or $X^a$ is a group $SiR^{5a} R^{6a} R^{7a}$ or $Sn R^{5a} R^{6a} R^{7a}$ wherein $R^{5a}$, $R^{6a}$ and $R^{7a}$ are the same or different and are each a hydrocarbyl group containing up to 6 carbon atoms unsubstituted or substituted by one to three halo, cyano, alkoxy, alkylthio, acyloxy or carbalkoxy groups containing up to 6 carbon atoms or $X^a$ is a group $R^{16}OCO$ wherein $R^{16}$ is $C_{1-4}$ alkyl;

q is 0 or 1 and t is 1 or 2; provided that the sum of q and t is not greater than 2; Y and $Y^1$ are the same or different and are each selected from oxygen and $S(O)_{n'}$ where n' is 0, 1 or 2; Z is $CH_2O$ or $CH_2S(O)_{n''}$ wherein n" is 0, 1 or 2, except that $X^a$ cannot be hydrogen when q is 0, t is 1 and $R^{15}$ is a single bond.

7. A compound of the formula (IB):

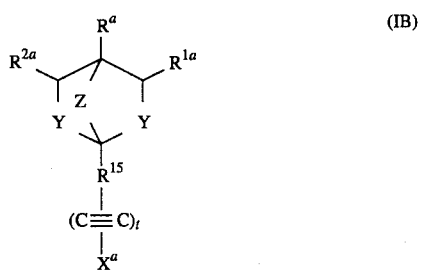

wherein $R^a$, $R^{1a}$, $R^{2a}$, $X^a$, Y, $Y^1$, Z and t are as hereinbefore defined in claim 6 and $R^{15a}$ is a single bond or a group $R^{15'}$ as hereinbefore defined in claim 6.

8. A compound of the formula (IC):

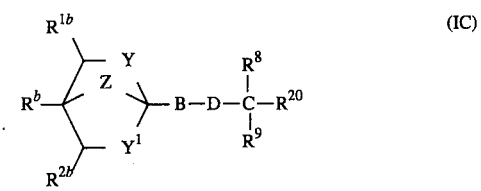

wherein $R^b$ is a $C_{2-10}$ non-aromatic hydrocarbyl group unsubstituted or substituted by cyano, halo, $C_{1-4}$ alkoxy, or a group $S(O)_{m^b}bR^{3b}$ where $R^{3b}$ is $C_{1-4}$ alkyl and $m^b$ is 0, 1 or 2 or $R^b$ is phenyl unsubstituted or substituted by $C_{1-4}$ alkoxy, $C_{1-3}$ alkyl, $C_{2-4}$ alkynyl, halo, $C_{1-4}$ haloalkyl, cyano or a group $S(O)_m bR^{3b}$ as defined in claim 1;

$R^{1b}$ and $R^{2b}$ are the same or different, and each is hydrogen, halo, or a $C_{1-3}$ aliphatic group unsubstituted or substituted by halo, cyano, $C_{1-5}$ carbalkoxy, or $C_{1-4}$ alkoxy; a group $S(O)_{m'}R^4$ wherein m' is 0, 1 or 2 and $R^4$ is $C_{1-4}$ alkyl; $C_{2-3}$ alkynyl, cyano, gem dimethyl, or $C_{1-5}$ carbalkoxy, or $R^{1b}$ and $R^b$ and the carbon atoms to which they are attached form a $C_{5-7}$ carbocyclic ring unsubstituted or substituted by halo, $C_{1-3}$ alkyl or alkoxy or $C_{2-3}$ alkenyl;

$R^8$, $R^9$ are as defined in claim 1 and $R^{20}$ is a group $R^8$ as defined in claim 1;

B is a single bond, methylene or a $C_{2-6}$ aliphatic chain which contains zero, one or two heteroatoms and single or double bonds but not triple bonds interspersed in the chain and which may be substituted by one to four substituents which are the same or different and are each independently selected from hydroxy, oxo, halo, $C_{1-4}$ alkyl, $C_{1-4}$ alkoxy, $C_{1-4}$ acyloxy, epoxy, a $C_{1-4}$ alkylidene group, a $C_{1-6}$ carbalkoxy group, $C_{1-4}$ haloalkyl or cyano;

D is a single bond or a group $CH_2O$, $CH_2S(O)_n$ wherein m is 0,1 or 2, or D is a 1,2 cyclopropyl group; Y and $Y^1$ and Z are as defined in claim 1, provided that B cannot be a single bond or methylene group when D is a single bond.

9. A compound selected from:
1-(Hex-5-ynyl)-4-propyl-2,6,7-trioxabicyclo[2.2.2]octane
1-(Pent-4-ynyl)-4-propyl-3-trifluoromethyl-2,6,7-trioxabicyclo[2.2.2]octane
1-(Hex-5-ynyl)-4-propyl-3-trifluoromethyl-2,6,7-trioxabicyclo[2.2.2]octane
1-(Pent-4-ynyl)-4-propyl-2,6,7-trioxabicyclo[2.2.2]octane-3-carbonitrile
1-(Hex-5-ynyl)-4-propyl-2,6,7-trioxabicyclo[2.2.2]octane-3-carbonitrile
4-(Cyclohexyl)-1-(pent-4-ynyl)-2,6,7-trioxabicyclo[2.2.2]octane
4-(Cyclohexyl)-1-(hex-5-ynyl)-2,6,7-trioxabicyclo[2.2.2]octane
4-t-Butyl-1-(hex-5-ynyl)-2,6,7-trioxabicyclo[2.2.2]octane
4-t-Butyl-1-(6-trimethylsilylhex-5-ynyl)-2,6,7-trioxabicyclo[2.2.2]octane
1-(4-Ethynylcyclohexyl)-4-propyl-2,6,7-trioxabicyclo[2.2.2]octane
4-t-Butyl-1-(4-ethynylcyclohexyl)-2,6,7-trioxabicyclo[2.2.2]octane (cis and trans isomers)
4-t-Butyl-1-(3,3-dimethylbut-1-ynyl)-2,6,7-trioxabicyclo[2.2.2]octane
1-(3,3-Dimethylbut-1-ynyl)-4-propyl-2,6,7-trioxabicyclo[2.2.2]octane-3-carbonitrile
4-t-Butyl-1-(hex-5-ynyl)-2,6-dioxa-7-thiabicyclo[2.2.2]octane
1-(Hex-5-ynyl)-4-propyl-2-oxa-6,7-dithiabicyclo[2.2.2]octane
1-(Hex-5-ynyl)-4-propyl-2,6,7-trithiabicyclo[2.2.2]octane
4-t-Butyl-1-[2-(prop-2-ynylthio)ethyl]-2,6,7-trioxabicyclo[2.2.2]octane
4-Propyl-1-[2-(prop-2-ynylthio)ethyl]-2,6,7-trioxabicyclo[2.2.2]octane
4-t-Butyl-1-[2-(prop-2-ynyloxy)ethyl]-2,6,7-trioxabicyclo[2.2.2]octane
4-Propyl-1-[2-(prop-2-ynyloxy)ethyl]-2,6,7-trioxabicyclo[2.2.2]octane-3-carbonitrile
1-(But-3-ynyloxymethyl)-4-propyl-2,6,7-trioxabicyclo[2.2.2]octane
4-t-Butyl-1-(but-3-ynyloxymethyl)-2,6,7-trioxabicyclo[2.2.2]octane
1-(But-3-ynyloxymethyl)-4-propyl-2,6,7-trioxabicyclo[2.2.2]octane-3-carbonitrile
4-t-Butyl-1-(hept-6-ynyl)-2,6,7-trioxabicyclo[2.2.2]octane
1-(Hept-6-ynyl)-4-propyl-2,6,7-trioxabicyclo[2.2.2]octane
4-Butyl-1-(hex-5-ynyl)-2,6,7-trioxabicyclo[2.2.2]octane-3-carbonitrile
1-(Hex-5-ynyl)-4-(2-methylprop-2-enyl)-2,6,7-trioxabicyclo[2.2.2]octane-3-carbonitrile
1-(Hex-5-ynyl)-4-(prop-2-enyl)-2,6,7-trioxabicyclo[2.2.2]octane-3-carbonitrile
1(But-3-ynyloxymethyl)-4-(prop-2-enyl)-2,6,7-trioxabicyclo[2.2.2]-octane-3-carbonitrile
4-(But-3-enyl)-1-(hex-5-ynyl)-2,6,7 -trioxabicyclo[2.2.2]octane -3-carbonitrile
4-t-Butyl-1 -(4-methylhex-5-ynyl)-2,6,7 -trioxabicyclo[2.2.2]octane
1-[2-(But-3-ynyloxy)ethyl]-4-propyl-2,6,7-trioxabicyclo[2.2.2]octane
1-[1-(But-3-ynyloxy)ethyl]-4-propyl-2,6,7-trioxabicyclo[2.2.2]octane
1-(But-3-ynylthiomethyl)-4-propyl-2,6,7-trioxabicyclo[2.2.2]octane 4-t-Butyl-1-(but-3-ynylthiomethyl)-2,6,7-trioxabicyclo[2.2.2]octane
4-Butyl-1-(hex-5-ynyl)-2-oxa-6,7-dithiabicyclo[2.2.2]octane
4-t-Butyl-1-(hex-5-ynyl)-2-oxa-6,7-dithiabicyclo[2.2.2]octane
4-t-Butyl-1-(hex-5-ynyl)-2,6,7-trioxabicyclo[2.2.2]octane-3-carbonitrile
1-(Hex-5-ynyl)-4-isobutyl-2,6,7-trioxabicyclo[2.2.2]octane-3-carbonitrile
4-Ethoxymethyl-1-(hex-5-ynyl)-2,6,7-trioxabicyclo[2.2.2]octane-3-carbonitrile
1-(1-Methylhex-5-ynyl)-4-propyl-2,6,7-trioxabicyclo[2.2.2]octane
4-t-Butyl-1-(1-methylhex-5-ynyl)-2,6,7-trioxabicyclo[2.2.2]octane
1-(1-Methylhex-5-ynyl)-4-propyl-2,6,7-trioxabicyclo[2.2.2]octane-3-carbonitrile
Methyl7-(4-propyl-2,6,7-trioxabicyclo[2.2.2]oct-1-yl)hept-2-ynoate
1-(Hex-5-ynyl)-4-phenyl-2,6,7-trioxabicyclo[2.2.2]octane
1-(Hex-5-ynyl)-4-isobutyl-2-oxa-6,7-dithiabicyclo[2.2.2]octane
1-(Hex-5-ynyl)-3-methyl-4-propyl-2-oxa-6,7-dithiabicyclo[2.2.2]octane
1-(3-Methylhex-5-ynyl)-4-propyl-2,6,7-trioxabicyclo[2.2.2]octane-3-carbonitrile
1-(2-Methylhex-5-ynyl)-4-propyl-2,6,7-trioxabicyclo[2.2.2]octane-3-carbonitrile
1-(3,3-Dimethylbut-1-ynyl)-4-isobutyl-2,6,7-trioxabicyclo[2.2.2]octane-3-carbonitrile
1-(But-3-ynyloxymethyl)-4-propyl-2,6,7-trithiabicyclo[2.2.2]octane
1-(trans-4(e)-ethynylcyclohexyl)-4-propyl-2,6,7-trioxabicyclo[2.2.2]octane-3-carbonitrile
4-Propyl-1-[(E/Z)-6-(trimethylsilyl)hex-3-en-5ynyl]-2,6,7-trioxabicyclo[2.2.2]octane-3-carbonitrile
1-[(E/Z)-Hex-3-en-5-ynyl]-4-propyl-2,6,7-trioxabicyclo[2.2.2]octane-3-carbonitrile (E:Z-1:2)
1-[(E/Z)-7-Methoxyhept-3-en-5-ynyl]-4-propyl-2,6,7-trioxabicyclo[2.2.2]octane-3-carbonitrile (E:Z-1:2)
1-[(E/Z)-7-Hydroxyhept-3-en-5-ynyl]-4-propyl-2,6,7-trioxabicyclo[2.2.2]octane-3-carbonitrile
4-t-Butyl-1-[(E)-hex-1-en-5-ynyl[-2,6,7-trioxabicyclo[2.2.2]octane-3-carbonitrile
4-Propyl-2,6,7-trioxabicyclo[2.2.2]octane-1-carboxaldehyde oxime O-(prop-2-ynyl)ether
1-(Hex-5-ynyl)-4-isobutyl-2,6,7-trithiabicyclo[2.2.2]octane
1-(Hex-5-ynyl)-4-phenyl-2-oxa-6,7-dithiabicyclo[2.2.2]octane
4-Propyl-1-(4-methylhex-5-ynyl)-2,6,7-trioxabicyclo[2.2.2]octane-3-carbonitrile
4-Ethyl-1-(hex-5-ynyl)-2,6,7-trithiabicyclo[2.2.2]octane
1-(Hex-5-ynyl)-4-phenyl-2,6,7-trioxabicyclo[2.2.2]octane-3-carbonitrile
4-Cyclopropylmethyl-1-(hex-5-ynyl)-2,6.7-trioxabicyclo[2.2.2]octane-3-carbonitrile
4-Isobutyl-1-(3-methylhex-5-ynyl)2,6,7-trioxabicyclo[2.2.2]octane-3-carbonitrile
1-[(s)-3-Methylhex-5-ynyl]-4-propyl-2,6,7-trioxabicyclo[2.2.2]octane-3-carbonitrile
1-(2-Methylhex-5-ynyl)-4-(prop-2-enyl)-2,6,7-trioxabicyclo[2.2.2]octane-3-carbonitrile
4-t-Butyl-1-(3,3-dimethylbutyl)-2,6,7-trioxabicyclo[2.2.2]octane
1-(3,3-Dimethylbutyl)-4-propyl-2,6,7-trioxabicyclo[2.2.2]octane-3-carbonitrile
1-[(E)-3,3-Dimethylbut-1-enyl]-4-propyl-2,6,7-trioxabicyclo[2.2.2]-octane-3-carbonitrile
1-(1-Butylthiomethyl)-4-propyl2,6,7-trioxabicyclo[2.2.2]octane-3-carbonitrile
1-[(z)-1-Fluoro-3,3-dimethylbut-1-enyl]-4-propyl2,6,7-trioxabicyclo[2.2.2]octane-3-carbonitrile
1-(Hept-5-ynyl)-4-propyl-2,6,7-trioxabicyclo[2.2.2)octane.

10. A pesticidal composition comprising a pesticidally effective amount of a compound according to claim 1 in admixture with a carrier or diluent.

11. The pesticidal composition according to claim 10 which additionally contains a synergist or a potentiator.

12. The pesticidal composition according to claim 10 which additionally contains a further active ingredient selected from a pesticidally active ingredient, an attractant, repellent, bacteriocide, fungicide, anthelmintics or combinations thereof.

13. A method for the control of an arthropod pest or a helminth pest which comprises administering to the arthropod or helminth or their environment an effective amount of a compound of claim 1.

14. A method for the control of a pesticidal infestation on an environment selected from animals, plants, stored products or the atmosphere which method comprises administering an effective amount of a compound of claim 1 to an environment susceptible to pest infestation.

* * * * *